United States Patent
Dellinger et al.

(10) Patent No.: US 11,548,876 B2
(45) Date of Patent: *Jan. 10, 2023

(54) ORTHOESTER COMPOSITIONS FOR AFFINITY PURIFICATION OF OLIGONUCLEOTIDES

(71) Applicant: Agilent Technologies, Inc., Santa Clara, CA (US)

(72) Inventors: Douglas J. Dellinger, Boulder, CO (US); Joel Myerson, Berkeley, CA (US); Brian Smart, Santa Clara, CA (US)

(73) Assignee: Agilent Technologies, Inc., Santa Clara, CA (US)

( * ) Notice: Subject to any disclaimer, the term of this patent is extended or adjusted under 35 U.S.C. 154(b) by 225 days.

This patent is subject to a terminal disclaimer.

(21) Appl. No.: 16/793,808

(22) Filed: Feb. 18, 2020

(65) Prior Publication Data

US 2020/0181124 A1  Jun. 11, 2020

Related U.S. Application Data

(63) Continuation of application No. PCT/US2018/000316, filed on Aug. 17, 2018.

(60) Provisional application No. 62/547,687, filed on Aug. 18, 2017.

(51) Int. Cl.
| | |
|---|---|
| *C07D 405/12* | (2006.01) |
| *C07D 317/34* | (2006.01) |
| *C07D 403/06* | (2006.01) |
| *C07H 21/02* | (2006.01) |
| *C07H 1/06* | (2006.01) |

(52) U.S. Cl.
CPC ......... *C07D 405/12* (2013.01); *C07D 317/34* (2013.01); *C07D 403/06* (2013.01); *C07H 21/02* (2013.01); *C07H 1/06* (2013.01)

(58) Field of Classification Search
CPC ............ A61K 31/7088; A61K 31/7105; A61K 31/711; A61K 31/7115; A61K 31/712; A61K 31/7125; C07H 21/02; C07H 21/04; C07H 1/06; C07D 405/12; C07D 317/34; C07D 403/06
See application file for complete search history.

(56) References Cited

U.S. PATENT DOCUMENTS

| | | | | |
|---|---|---|---|---|
| 3,658,787 A * | 4/1972 | Russell et al. | ......... | C07H 19/16 536/27.61 |
| 6,111,086 A * | 8/2000 | Scaringe | ................ | C07H 15/08 536/26.72 |
| 8,344,118 B2 * | 1/2013 | Kore | ...................... | C07H 21/02 536/26.6 |
| 10,988,501 B2 * | 4/2021 | Li | ......................... | C12Q 1/6869 |
| 11,299,483 B2 * | 4/2022 | Dellinger | ............. | C07D 403/06 |
| 2020/0190129 A1 * | 6/2020 | Dellinger | ............. | C07D 405/12 |

FOREIGN PATENT DOCUMENTS

| | | | | |
|---|---|---|---|---|
| CN | 101547928 A | 9/2009 | | |
| CN | 103492405 A | 1/2014 | | |
| EP | 529741 A1 * | 3/1993 | ............. | B01D 71/44 |
| EP | 0529741 A1 | 3/1993 | | |
| EP | 2508530 A1 | 10/2012 | | |
| JP | H05194655 A | 8/1993 | | |
| WO | 2006081035 A2 | 8/2006 | | |
| WO | 2008077600 A1 | 7/2008 | | |
| WO | 2013137922 A2 | 9/2013 | | |

OTHER PUBLICATIONS

M. Sekine et al., 105 Journal of the American Chemical Society, 2044-2049 (1983) (Year: 1983).*
B. Karwowski et al., 24 Nucleosides, Nucleotides, and Nucleic Acids, 1111-1114 (2005) (Year: 2005).*
W. Pearson et al., 70 Journal of Organic Chemistry, 7114-7122 (2005) (Year: 2005).*
W. Meylan et al., 19 Perspectives In Drug Discovery and Design, 67-84 (2000) (Year: 2000).*
B. Karwowski et al., 44 Journal of Heterocyclic Chemistry, 329-336 (2007) (Year: 2007).*
Tech Tip # 56, Calculate reagent log P values to determine solubility characteristics (Thermo Scientific, 2007) (Year: 2007).*
E. Souza et al., 12 International Journal of Molecular Sciences, 7250-7264 (2011) (Year: 2011).*
S. Obika, 9 Bioorganic & Medicinal Chemistry Letters, 515-518 (1999) (Year: 1999).*
Hawley's Condensed Chemical Dictionary, p. 996, 1009, 1286 (16th ed., 2016, R.J. Larrañaga ed.) (Year: 2016).*
Marshall, et al., "Recent Advances In The High-Speed Solid Phase Synthesis Of Rna", Current Opinion in Chemical Biology, vol. 8, May 6, 2004, 222-229.
Sekine, et al., "Cyclic Orthoester Functions as New Protecting Groups in Nucleosides", J. American Chemical Society, vol. 105, No. 7, 1983, 2044-2049.
Chiang, et al., "Catalysis by Undissociated H3P04 in Aqueous H2P04-/HP04= Buffer Solutions: Dependence on the Magnitude of the Broensted Exponent", Journal of Organic Chemistry, vol. 51 No. 21, Oct. 1, 1986, 4035-4037.
Kurbanov, et al., "Preparation and Biological Activity of 2 Alkoxy 5 5 Bischloromethyl 1 3 Dioxanes and their Nitrous Analogs", Doklady Akademii Nauk SSSR, vol. 314 No. 3, Mar. 1, 1990, 640-644.
International Search Report & Written Opinion dated Dec. 17, 2018, Application No. PCT/US2018/000316, 18 pages.

(Continued)

*Primary Examiner* — Alexander R Pagano

(57) ABSTRACT

Compounds and methods for purifying oligonucleotides such as RNA and DNA. A target oligonucleotide is reacted with an orthoester linker comprising an affinity tag to form an orthoester oligonucleotide-orthoester linker conjugate which is subjected to a purification technique to separate the target oligonucleotide from impurities such as truncated oligonucleotides. The orthoester linker can be then removed under mild conditions to generate the target oligonucleotide in high purity.

9 Claims, 9 Drawing Sheets

Specification includes a Sequence Listing.

(56) References Cited

OTHER PUBLICATIONS

Pearson, et al., "Fluorous Affinity Purification of Oligonucleotides", Journal of Organic Chemistry, vol. 70, No. 18, Jan. 1, 2005, 7114-7122.
Kurbanov, D et al., "Synthesis And Biological Activity Of 2-Alkoxy-5,5-Bis(Chloromethyl)-1,3-Dioxanes and Their Amino Analogs," Doklady Akademii Nauk Sss, vol. 314, No. 3,1990, 3 pages.
Özgener, H et al., "2-Dichloromethyl-1,3-Dioxolan-2-YI Orthoesters. A Potential Protecting Group For Sugar Derivatives," Journal Of Carbohydrate Chemistry, vol. 21, No. 6, 2002, 2002, 10 pages.

* cited by examiner

ORTHOESTER COMPOSITIONS FOR AFFINITY PURIFICATION OF OLIGONUCLEOTIDES

CROSS-REFERENCE TO RELATED APPLICATION

This application is a continuation of International Application No. PCT/US2018/000316, filed on Aug. 17, 2018, which claims the benefit of U.S. Provisional Application No. 62/547,687, filed Aug. 18, 2017, the contents of which are incorporated by reference in their entirety.

FIELD OF THE INVENTION

The present disclosure relates to compounds and methods for purification of biopolymers, such as RNA and DNA.

BACKGROUND

Solid-phase synthesis is an invaluable tool which can be used to prepare custom oligonucleotide sequences (e.g., custom RNA and DNA), custom peptides, custom oligosaccharides, and various metabolites. The chemical synthesis of oligonucleotides generally occurs in a sequential fashion in which one end of the growing chain is attached to a solid surface, and reactive nucleotide monomers are condensed sequentially using a repetitive synthesis cycle. These nucleotide monomers contain a reactive phosphorus group such as phosphoramidite, H-phosphonate, or other reactive phosphorus or modified groups well known in the art, and the building blocks are derived from protected, 2'-deoxynucleosides (dA, dC, dG, and T), protected ribonucleosides (A, C, G, and U), or protected chemically modified nucleosides. The typical desired oligonucleotide product contains an internucleotide bond between the 5'-hydroxyl and 3'-hydroxyl of adjacent nucleotides. However, it may also be desirable to form unnatural internucleotide linkages between any of the hydroxyl groups on adjacent nucleotides. To accomplish the synthesis, the first step of the synthesis cycle is generally the reaction of a protected monomer with a nucleoside attached to the surface or reaction of a protected monomer with a hydroxyl group on the surface. The hydroxyl group on the surface can either be part of a cleavable universal linker or non-cleavable surface attachment. After initial coupling of the reactive phosphorus group with a hydroxyl on the surface, the steps that follow typically include capping of unreacted hydroxyl groups and then oxidation of the reactive phosphorus intermediate. Under certain conditions where certain modified phosphorus groups are being used, it may be necessary to oxidize prior to capping, especially in the case where the oxidation reagent produces a modified phosphorus group such as a phosphorothioate, boranophosphonate, or phosphoramidate. The final step is usually the deblocking of the hydroxyl group that will couple to the next protected nucleotide monomer. The protecting group removed in this final step is generally a dimethoxytrityl group (DMT). However, many other protective groups are well known in the art such as, for example, the 9-phenylxanthyl group (Pixyl), benzhydryloxy-bis(trimethylsilyloxy)silyl (BZH). Upon the completion of the chain assembly, the desired product is released from the solid phase, deprotected, and utilized in further biological applications.

The oligonucleotide product should be free of shorter, truncated sequences and of sequences having a different sequence than the desired product since the presence of side-products may cause undesired effects when used in in vitro or in vivo experiments. A desirable oligonucleotide synthesis would provide the chosen oligonucleotide in quantitative yield, such that the completed synthetic composition contains only the target oligonucleotide product. However, chemical methods generally provide less than quantitative yield and are usually in the range of 95% to 99% yield. The crude reaction mixture often comprises a mixture of desired oligonucleotide and truncated or failure sequences and requires purification to obtain a clean oligonucleotide target product.

The most common method of purifying the desired oligonucleotide product out of the crude synthesis products is high performance liquid chromatography (HPLC). However, isolation of the target full-length oligonucleotide from shorter oligonucleotide sequences often requires chromatographic conditions that are laborious and time consuming. For longer oligonucleotides such as oligonucleotides having 100 or more nucleotides, HPLC elution gradients can take two to three hours for each run, and the process requires precise collection and fraction analysis to obtain acceptable levels of purity. Moreover, such chromatographic methods often require stationary phases having very small particle sizes and abundant theoretical plates.

In standard oligonucleotide synthesis methods, the failure sequences are capped with an acetyl group or other acid-stable reactive functional groups and the full-length oligonucleotide comprises a dimethoxytrityl group, 9-phenylxanthyl group (Pixyl), benzhydryloxy-bis(trimethylsilyloxy)silyl (BZH) or other well-known groups at the 5'-hydroxyl position. Researchers have proposed that the full-length oligonucleotide product may be distinguished from the failure sequences by the chemical group on the 5'-hydroxyl of the oligonucleotide molecule at the completion of the synthesis cycle. Since groups like the dimethoxytrityl group are significantly more hydrophobic than the acetyl group, this difference can theoretically be used to separate the full-length oligonucleotide products from the capped failure products using a chromatographic method such as reverse-phase HPLC (J. Chrom. 326, 293-299; 1985). However, the use of DMT for HPLC purification has several drawbacks. While the DMT group is easily removed while the nucleotide is on a solid support due to favorable equilibrium conditions, the DMT group is significantly harder to remove after removal of the oligonucleotide from the solid support and requires strong acid conditions and long reaction times. Unfortunately, the conditions required to remove the DMT group in solution can degrade the purified oligonucleotide ultimately resulting in a significant loss of purity. For DNA, such conditions are especially harsh on purine bases, resulting in cleavage of the glycosidic bond. For RNA, exposure to acid is even more problematic since such exposure can directly cleave the internucleotide bond and catalyze isomerization of the internucleotide bond resulting in a mixture of 5'-3' and 5'-2' linked RNA products.

Accordingly, there is a need for methods and compounds for mild and effective purification of oligonucleotides to produce oligonucleotides of high purity. The present disclosure provides methods and compounds for purifying oligonucleotides using an affinity tag which is cleavable under mild conditions and has little or no overall effect on the purity or integrity of the oligonucleotide product. These compounds can also be reacted with nascently synthesized biopolymers and biologically active metabolites which contain an accessible hydroxyl group. The affinity tag can be used to purify the biopolymer or metabolite.

SUMMARY

These and other features and advantages of the present methods and compounds will be apparent from the following detailed description, in conjunction with the appended claims.

In one aspect, this disclosure provides a method of purifying a target oligonucleotide. The method comprises the following steps:
1. synthesizing the target oligonucleotide on a solid support and obtaining a mixture comprising the target oligonucleotide and truncated oligonucleotides;
2. reacting the target oligonucleotide with an orthoester linker, and thereby forming an oligonucleotide-orthoester linker conjugate, wherein the orthoester linker either comprises an affinity tag at the time of conjugation or the affinity tag is reacted with the oligonucleotide-orthoester linker conjugate in a second reaction after the conjugation reaction;
3. cleaving the oligonucleotide-orthoester linker conjugate and the truncated oligonucleotides from the solid support;
4. loading the oligonucleotide-orthoester linker conjugate and the truncated oligonucleotides onto a chromatographic column or an affinity capture support and binding the oligonucleotide-orthoester linker conjugate by the affinity tag to the affinity capture support;
5. washing off the truncated oligonucleotides form the column or the affinity capture support; and
6. cleaving the orthoester linker from the target oligonucleotide and eluting the target oligonucleotide from the chromatographic column or the affinity capture support, and thereby releasing the purified target oligonucleotide.

In the method, the affinity tag may be one or more groups in the orthoester linker or the affinity tag is linked with a linker to the orthoester linker.

In any of these methods, the second reaction is conducted before or after the oligonucleotide-orthoester linker conjugate is cleaved from the solid support.

In any of these methods, the orthoester linker may be attached at the 5'-hydroxyl of the target oligonucleotide or the orthoester linker is attached at the 3'-hydroxyl of the target oligonucleotide.

In any of the methods provided in this disclosure, the affinity tag may comprise one or more of the following: a fluorous tag, a hydrophobic tag, a biotin tag, a glutathione tag, a maltose tag, an arylboronic acid tag, a poly-histidine peptide tag, a poly-sulfhydryl tag, a cyclodextrin tag, an adamantane tag, a polyamine tag, a maleimide tag, an alkyne tag, an azido tag, a hydrazide tag, an amino tag, a diol tag, a thiol tag, or any combination thereof.

The present methods can be performed with the target oligonucleotide comprising an oligoribonucleotide (RNA). This RNA may comprise a 2'-hydroxyl protecting group selected from a thionocarbamate (TC) protecting group, bis(2-acetoxyethoxy)methyl (ACE) protecting group, t-butyldimethylsilyl (TBDMS) protecting group, triisopropylsilyloxymethyl (TOM) protecting group, pivaloyloxymethyl (PivOM) protecting group and 2-cyanoethoxymethyl (CEM) protecting group. The RNA may further comprise a phosphorous protecting group, a nucleobase protecting group, or a combination thereof. In the RNA, the phosphorous protecting group may be deprotected before reacting the oligonucleotide with the orthoester linker. In the RNA, the nucleobase protecting group and optionally the phosphorous protecting group may be deprotected after reacting the target oligonucleotide with the orthoester linker. In these methods, the cleavage of the oligonucleotide-orthoester linker conjugate from the solid support and the deprotection of the nucleobase protecting group and optionally of the phosphorus protecting group may be performed in a single reaction. The RNA may comprise at least 70 nucleotides.

In any of the purification methods provided in this disclosure, the orthoester linker may be a compound of formula (Ia):

wherein each of R, R', R", and R'" is independently a $C_1$-$C_{24}$ alkyl, a $C_2$-$C_{24}$ alkenyl, a $C_2$-$C_{24}$ alkynyl, a halosubstituted $C_1$-$C_{24}$ alkyl, a halosubstituted $C_2$-$C_{24}$ alkenyl, a halosubstituted $C_2$-$C_{24}$ alkynyl, a carbocyclyl, a heteroalkyl, an aryl, a heteroaryl, a heterocycle or any substituted equivalents, with a proviso that R may be a hydrogen.

In the compound of formula (Ia), R may be H or $C_1$-$C_3$ alkyl and R', R", R'" are each independently may be an aryl or a substituted aryl. In the compound of formula (Ia), R may be wherein R is H or $CH_3$ and R', R", R'" may be phenyl or a substituted phenyl. In the compound of formula (Ia), at least one of R, R', R", and R'" may be a hydrophobic tag, partial hydrophobic tag, fluorous tag, or partial fluorous tag.

In any of the purification methods provided in this disclosure, the orthoester linker may be a compound of formula (Ib):

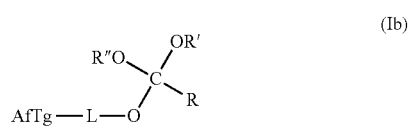

wherein AfTg is an affinity tag and R, R', R" are each independently AfTg-L or a $C_1$-$C_{24}$ alkyl, a $C_2$-$C_{24}$ alkenyl, a $C_2$-$C_{24}$ alkynyl, a halosubstituted $C_1$-$C_{24}$ alkyl, a halosubstituted $C_2$-$C_{24}$ alkenyl, a halosubstituted $C_2$-$C_{24}$ alkynyl, a carbocyclyl, a heteroalkyl, an aryl, a heteroaryl, a heterocycle, any substituted equivalents or a combination thereof provided that the total number of carbons doesn't exceed 24; and wherein L is a covalent bond or a straight, branched, mono- or poly-cyclic, saturated, partially unsaturated or unsaturated $C_1$-$C_{12}$ hydrocarbon chain that is optionally substituted with F, Cl, Br, I or $C_1$-$C_3$ alkyls and optionally interspersed with heteroatoms independently selected from: O, S, N, or with groups independently selected from S—S, $NR^a$, $NR^a$—CO, —CO—$NR^a$—, $NR^a$—CO—$NR^b$, CO wherein $R^a$, $R^b$ are each independently H or $C_1$-$C_6$ alkyl.

In any of the purification methods provided in this disclosure, the orthoester linker may be a compound of formula (I)

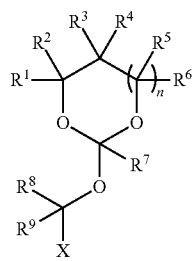

wherein each of $R^1$, $R^2$, $R^3$, $R^4$, $R^5$, $R^6$ and $R^7$ is independently H, $C_1$-$C_{24}$ alkyl, $C_1$-$C_{24}$ heteroalkyl, $C_2$-$C_{24}$ alkenyl, $C_2$-$C_{24}$ heteroalkenyl, $C_2$-$C_{24}$ alkynyl, $C_2$-$C_{24}$ heteroalkynyl, halogen, aryl, heteroaryl, heterocyclyl, carbocyclyl, or any substituted equivalents or combination thereof provided that the total number of carbons doesn't exceed 24; $R^8$ and $R^9$ are H; X is H, methyl or an electron withdrawing group; and n is 0, 1, or 2, wherein at least one of $R^1$, $R^2$, $R^3$, $R^4$, $R^5$, $R^6$ or $R^7$ comprises an affinity tag. In some embodiments, at least one of $R^1$, $R^2$, $R^3$, $R^4$, $R^5$, $R^6$ or $R^7$ in the compound of the formula (I) is a fluorosubstituted alkyl, a fluorosubstituted alkenyl, a fluorosubstituted alkynyl, a fluorosubstituted carbocyclyl, a fluorosubstituted heteroalkyl, a fluorosubstituted heteroalkenyl, a fluorosubstituted heteroalkynyl, or a fluorosubstituted heterocyclyl.

In the purification methods provided in this disclosure, the affinity tag may be a fluorous or a hydrophobic tag with a cLog P value of at least 3. In the purification methods according to this disclosure, the affinity tag may be a fluorosubstituted alkyl, a fluorosubstituted alkenyl, a fluorosubstituted alkynyl, or a fluorosubstituted carbocyclyl.

In some embodiments, the purification methods are conducted with the following orthoester linker:

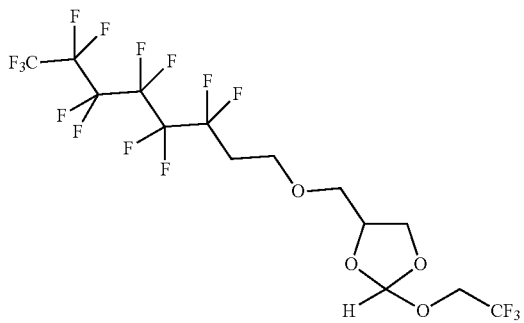 [SMILES: FC(F)(F)COC1OCC(COCCC(F)(F)C(F)(F)C(F)(F)C(F)(F)C(F)(F)C(F)(F)F)O1]

In further aspects, the present disclosure provides an oligonucleotide orthoester linker conjugate comprising an oligonucleotide which comprises at its 5' or 3'end a moiety of formula (IV).

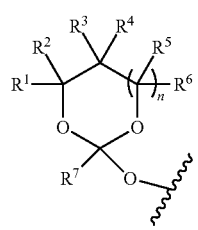

wherein the oxygen linked to the squiggly line is the oxygen of the 5'end or the 3'end of the oligonucleotide;
wherein at least one of $R^1$, $R^2$, $R^3$, $R^4$, $R^5$, $R^6$ and $R^7$ is $C_1$-$C_{24}$ alkyl, $C_1$-$C_{24}$ heteroalkyl, $C_2$-$C_{24}$ alkenyl, $C_2$-$C_{24}$ heteroalkenyl, $C_2$-$C_{24}$ alkynyl, $C_2$-$C_{24}$ heteroalkynyl, halogen, aryl, heteroaryl, heterocyclyl, carbocyclyl, any substituted equivalent or a combination thereof and the remaining $R^1$, $R^2$, $R^3$, $R^4$, $R^5$, $R^6$ and $R^7$ are H, $C_1$-$C_6$ alkyl, $C_2$-$C_6$ alkenyl, $C_2$-$C_6$ alkynyl, $C_6$-$C_{12}$ arylalkyl, carbocyclyl, heterocyclyl, any substituted equivalent or combination thereof; and n is 0, 1, or 2, wherein at least one of $R^1$, $R^2$, $R^3$, $R^4$, $R^5$, $R^6$ or $R^7$ comprises an affinity tag; and with the proviso that said moiety is not

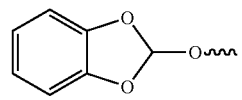

The oligonucleotide orthoester linker conjugates of with the moiety of the formula (IV) include compounds, wherein at least one of $R^1$, $R^2$, $R^3$, $R^4$, $R^5$ or $R^6$ is a fluorosubstituted alkyl, a fluorosubstituted alkenyl, a fluorosubstituted alkynyl, or a fluorosubstituted aryl, a fluorosubstituted heteroalkyl, a fluorosubstituted heteroalkenyl, a fluorosubstituted heteroalkynyl, or a fluorosubstituted heterocyclyl. In further embodiments, the oligonucleotide orthoester linker conjugates with the moiety of the formula (IV) include compounds, wherein at least one of $R^1$, $R^2$, $R^3$, $R^4$, $R^5$ or $R^6$ is a fluorous tag and the remaining R groups including $R^7$ are H. In further embodiments, the oligonucleotide orthoester linker conjugates of the formula (IV) include compounds, wherein at least two of $R^1$, $R^2$, $R^3$, $R^4$, $R^5$ or $R^6$ are a fluorous tag.

The oligonucleotide orthoester linker conjugates with the moiety of the formula (IV) include compounds, wherein n=0 and the affinity tag is a fluorous or a hydrophobic tag with a cLog P value of at least 3.

In some embodiments, the oligonucleotide in the oligonucleotide orthoester linker conjugate with the moiety of the formula (IV) comprises an oligoribonucleic acid (RNA).

In some embodiments of the oligonucleotide orthoester linker conjugates, the moiety of the formula (IV) is selected from the group consisting of:

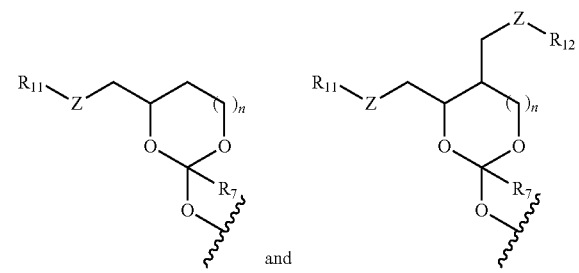

wherein $R^{11}$ and $R^{12}$ are each independently H, $C_1$-$C_{23}$ alkyl, $C_1$-$C_{23}$ heteroalkyl, $C_1$-$C_{23}$ substituted alkyl, $C_2$-$C_{23}$ alkenyl, $C_2$-$C_{23}$ heteroalkenyl, $C_2$-$C_{23}$ substituted alkenyl, $C_2$-$C_{23}$ alkynyl, $C_2$-$C_{23}$ heteroalkynyl, $C_2$-$C_{23}$ substituted alkynyl, aryl, substituted aryl, heteroaryl, substituted heteroaryl, heterocyclyl or substituted heterocyclyl provided that at least one of $R^{11}$ and $R^{12}$ comprises an affinity tag; $R^7$ is H, methyl, ethyl, n-propyl, phenyl or benzyl; Z are each independently $CR^aR^b$, O, S or $NR^a$ wherein $R^a$ and $R^b$ are each independently H, $C_1$-$C_6$ alkyl, or $R^a$ and $R^{11}$ or $R^a$ and $R^{12}$ together form a heterocycle with N; n is 0, 1, or 2.

In some embodiments of the oligonucleotide orthoester linker conjugates with the moiety of the formula (IV), the moiety is:

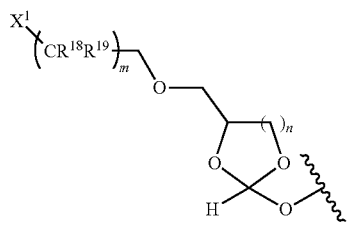

wherein $X^1$ is H, F, an azido, a protected sulfhydryl, a protected poly-sulfhydryl, a poly-histidine, a protected amino group, a protected hydrazide group, a protected oxyamine group, a maleimide, a cyclooctyne, a conjugated diene, a $C_2$ alkenyl group, a $C_2$ substituted alkenyl group, a $C_2$ alkynyl group or a $C_2$ substituted alkynyl group; $R^{18}$ and $R^{19}$ are each independently H, F, $C_{1-3}$ heteroalkyl or $C_{1-3}$ substituted alkyl; n is 1 or 2; and m is an integer ranging from 0 to 12.

In some embodiments of the oligonucleotide orthoester linker conjugates with the moiety the formula (IV), said moiety is selected from the group consisting of:

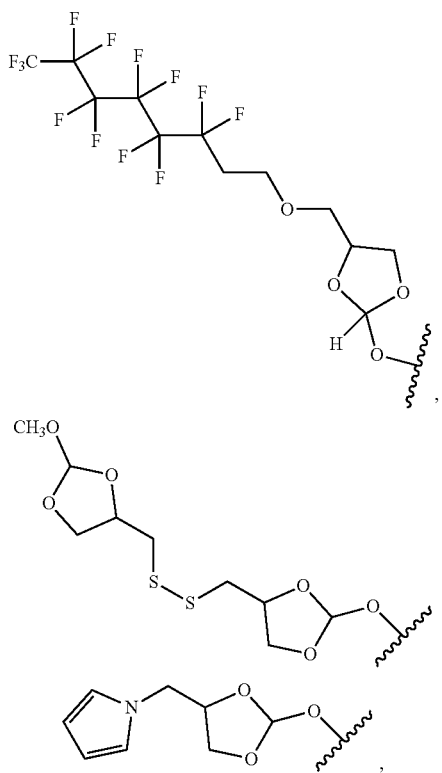

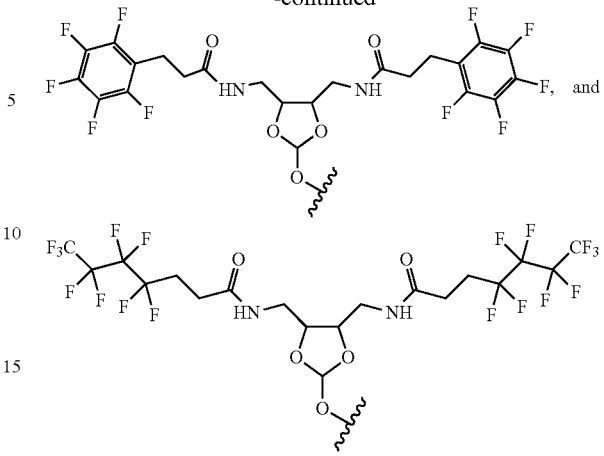

Further aspects of this disclosure relate to an orthoester linker of formula (Id)

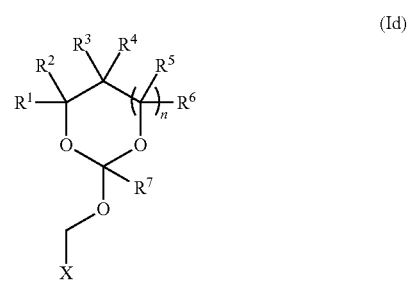

wherein at least one of $R^1$, $R^2$, $R^3$, $R^4$, $R^5$, $R^6$ and $R^7$ is $C_1$-$C_{24}$ alkyl, $C_1$-$C_{24}$ heteroalkyl, $C_2$-$C_{24}$ alkenyl, $C_2$-$C_{24}$ heteroalkenyl, $C_2$-$C_{24}$ alkynyl, $C_2$-$C_{24}$ heteroalkynyl, halogen, aryl, heteroaryl, heterocyclyl, carbocyclyl, any substituted equivalent or any combination thereof provided that the total number of carbons doesn't exceed 24 and the remaining $R^1$, $R^2$, $R^3$, $R^4$, $R^5$, $R^6$ and $R^7$ are H, $C_1$-$C_6$ alkyl, $C_2$-$C_6$ alkenyl, $C_2$-$C_6$ alkynyl, halo- or hetero-substituted equivalents, $C_3$-$C_{12}$ carbocyclyl or heterocyclyl and substituted equivalents with the proviso that two R groups of $R^1$ to $R^7$ groups do not form a fused ring with the cyclic orthoester as shown below:

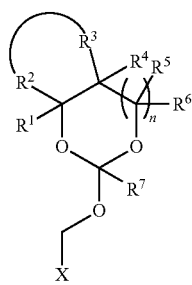

X is F, Cl, Br, or a mono-, bis or tris-halosubstituted methyl; and n is 0 or 1, wherein at least one of $R^1$, $R^2$, $R^3$, $R^4$, $R^5$, $R^6$ or $R^7$ comprises an affinity tag.

The orthoester linker of the formula (Id) may have the following structure:

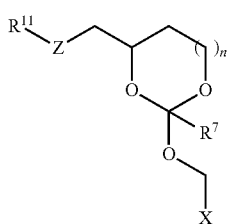

wherein $R^{11}$ is H, $C_1$-$C_{23}$ alkyl, $C_1$-$C_{23}$ heteroalkyl, $C_1$-$C_{23}$ substituted alkyl, $C_2$-$C_{23}$ alkenyl, $C_2$-$C_{23}$ heteroalkenyl, $C_2$-$C_{23}$ substituted alkenyl, $C_2$-$C_{23}$ alkynyl, $C_2$-$C_{23}$ heteroalkynyl, $C_2$-$C_{23}$ substituted alkynyl, aryl, substituted aryl, heteroaryl, substituted heteroaryl, heterocyclyl or substituted heterocyclyl; $R^7$ is H or $CH_3$. Z is $CR^aR^b$, O, S, $NR^a$, $NR^aCO$, $CONR^a$, wherein $R^a$ and $R^b$ are each independently H, $C_1$-$C_6$ alkyl, or $R^a$ and $R^{11}$ together form a heterocycle with N; X is F, Cl, Br, or a mono-, bis or tris-halosubstituted methyl; and n is 0 or 1, $R^{11}$ comprises an affinity tag.

The orthoester linker of the formula (Id) may have the structure:

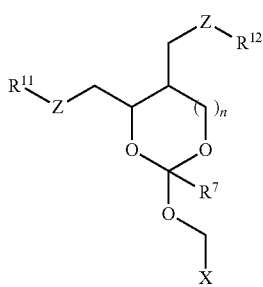

wherein $R^{11}$ and $R^{12}$ are each independently H, $C_1$-$C_{23}$ alkyl, $C_1$-$C_{23}$ heteroalkyl, $C_1$-$C_{23}$ substituted alkyl, $C_2$-$C_{23}$ alkenyl, $C_2$-$C_{23}$ heteroalkenyl, $C_2$-$C_{23}$ substituted alkenyl, $C_2$-$C_{23}$ alkynyl, $C_2$-$C_{23}$ heteroalkynyl, $C_2$-$C_{23}$ substituted alkynyl, aryl, substituted aryl, heteroaryl, substituted heteroaryl, heterocyclyl or substituted heterocyclyl provided that at least one of $R^{11}$ and $R^{12}$ comprises an affinity tag; $R^7$ is H or $CH_3$. Z are each independently $CR^aR^b$, O, S, $NR^aCO$, $CONR^a$ or $NR^a$ wherein $R^a$ and $R^b$ are each independently H, $C_1$-$C_6$ alkyl, or $R^a$ and $R^{11}$ or $R^a$ and $R^{12}$ together form a heterocycle with N; X is F, Cl, Br, or a mono-, bis or tris-halosubstituted methyl; and n is 0 or 1.

Any of the orthoester linkers of the formula (Id), may have the affinity tag wherein the affinity tag is a fluorous tag or a hydrophobic tag with a cLog P value of at least 3.

Some of the orthoester linkers of the formula (Id) include compounds, wherein n is 0 and at least two of $R^1$, $R^2$, $R^3$, $R^4$, $R^5$, and $R^6$ are each independently $C_1$-$C_{24}$ alkyl, $C_1$-$C_{24}$ heteroalkyl, $C_2$-$C_{24}$ alkenyl, $C_2$-$C_{24}$ heteroalkenyl, $C_2$-$C_{24}$ alkynyl, $C_2$-$C_{24}$ heteroalkynyl, halogen, aryl, heteroaryl, heterocyclyl, carbocyclyl or any substituted equivalent, and all the remaining R groups of $R^1$, $R^2$, $R^3$, $R^4$, $R^5$, and $R^6$ are H, provided that the two R groups that are not H are not linked together to form a fused ring with the cyclic orthoester. Some of the orthoester linkers of the formula (Id) include compounds, wherein one of $R^1$, $R^2$, $R^3$, $R^4$, $R^5$ or $R^6$ is a fluorosubstituted alkyl, a fluorosubstituted alkenyl, a fluorosubstituted alkynyl, or a fluorosubstituted aryl.

Further aspects of this disclosure include a fluorous orthoester linker having the structure:

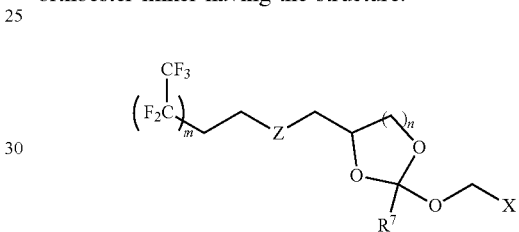

wherein Z is $CH_2$. O, S, $NR^a$, or $NR^aCO$ wherein $R^a$ is H or $C_1$-$C_6$ alkyl; $R^7$ is H, methyl, ethyl. n-propyl, phenyl or benzyl; X is H, F, Cl, Br, or a mono-, bis or tris-halosubstituted methyl or cyano; m is an integer from 0 to 12; n is 1 or 2.

Further aspects of this disclosure include an orthoester linker having the structure selected from:

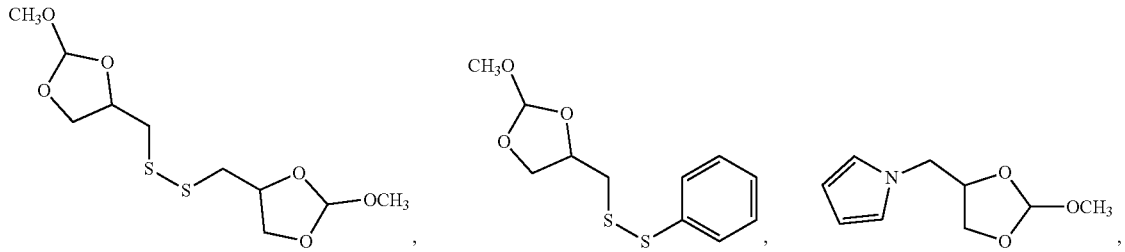

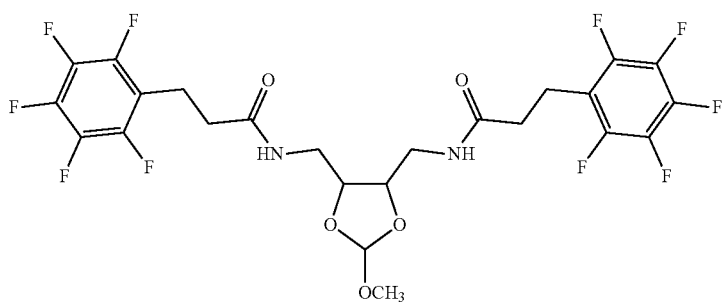

and

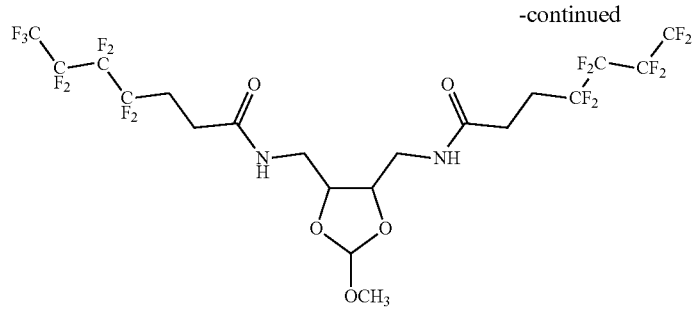

Further aspects of this disclosure include an orthoester linker of formula (IIIa):

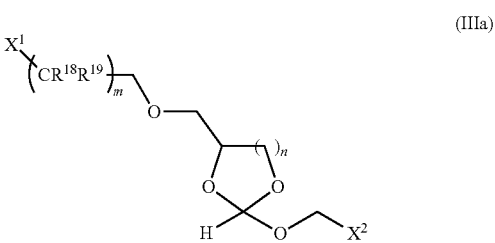

(IIIa)

wherein $X^1$ is H, F, an azido, a protected sulfhydryl, a protected poly-sulfhydryl, a poly-histidine, a protected amino group, a protected hydrazide group, a protected oxyamine group, a cyclooctyne, a conjugated diene, a $C_2$ alkenyl group, a $C_2$ substituted alkenyl group, a $C_2$ alkynyl group or a $C_2$ substituted alkynyl group; $R^{18}$ and $R^{19}$ are each independently H, F, $C_{1-3}$ heteroalkyl or $C_{1-3}$ substituted alkyl; $X^2$ is H, $CH_3$, F, Cl, Br, or a mono-, bis or tris-halosubstituted methyl or cyano; n is 1 or 2; and m is an integer ranging from 0 to 12.

The orthoester linker of the formula (IIIa) may be the following compound:

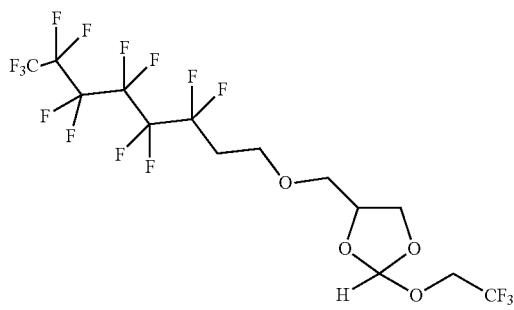 [SMILES: FC(F)(F)COC1OCC(COCCC(F)(F)C(F)(F)C(F)(F)C(F)(F)C(F)(F)C(F)(F)F)O1]

These and other features and advantages of the present methods and compounds will be apparent from the following detailed description, in conjunction with the appended claims.

DEFINED TERMINOLOGY

Figure 1:
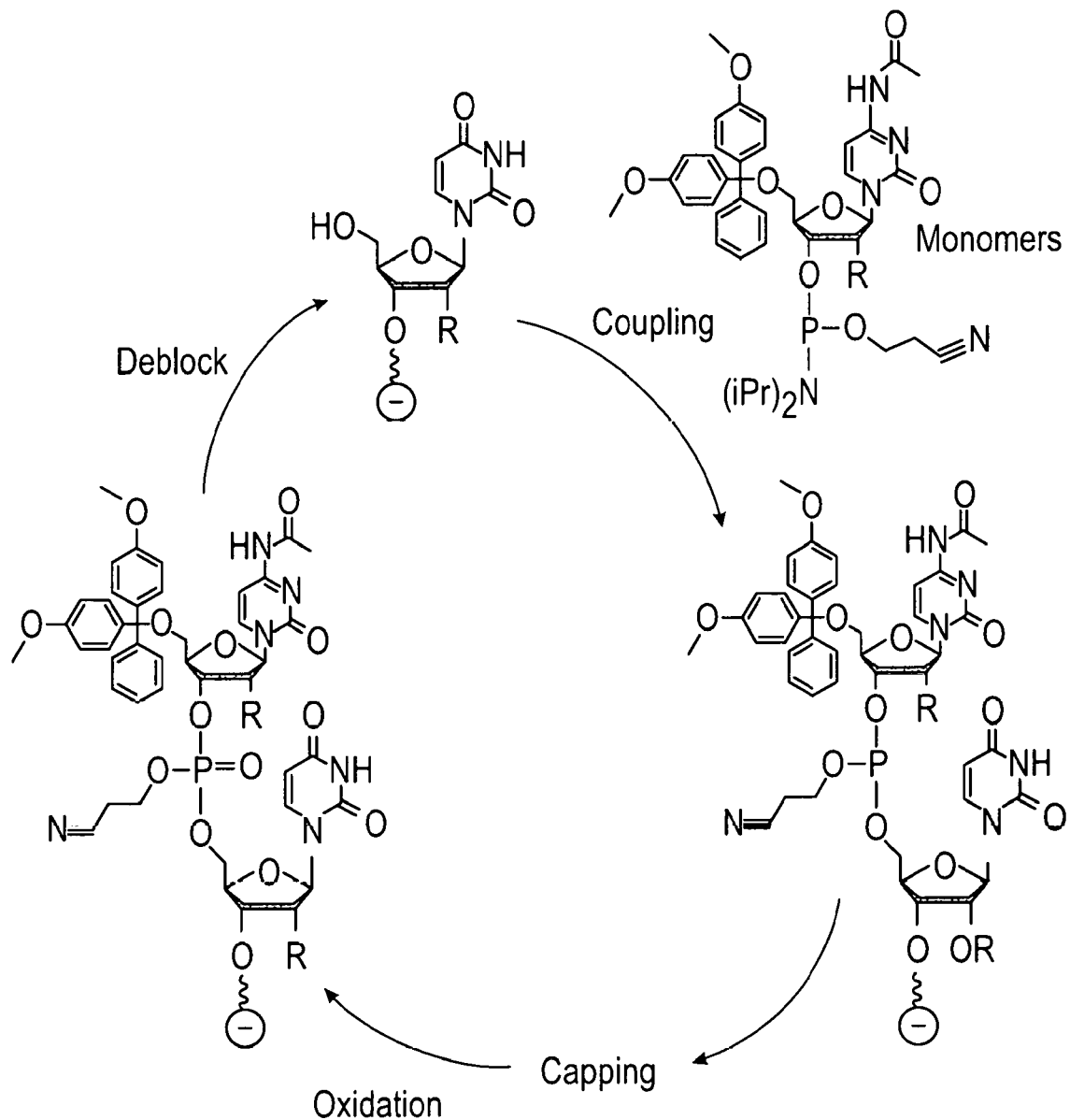
FIG. 1 shows a typical chemical synthesis of oligonucleotides on a solid support.

It is to be understood that the terminology used herein is for purposes of describing particular embodiments only and is not intended to be limiting. The defined terms are in addition to the technical and scientific meanings of the defined terms as commonly understood and accepted in the technical field of the present teachings.

The term "substituted" in reference to alkyl, heteroalkyl, alkenyl, heteroalkenyl, alkynyl, heteroalkynyl, aryl, heteroaryl, heterocycle etc., and termed "substituted equivalent" for example, "substituted alkyl", "substituted heteroalkyl", "substituted alkenyl", substituted heteroalkenyl", "substituted alkynyl", "substituted heteroalkynyl", "substituted aryl", "substituted heteroaryl", and "substituted heterocycle" means alkyl, heteroalkyl, alkenyl, heteroalkenyl, alkynyl, heteroalkynyl, aryl, heteroaryl, heterocycle, respectively, in which one or more hydrogen atoms are each independently replaced with a non-hydrogen substituent. Typical substituents include, but are not limited to, —X, —R, —O—, =O, —OR, —SR, —S—, —NR$_2$, —N$^+$R$_3$, =NR, —CX$_3$, —CN, —OCN, —SCN, —N=C=O, —NCS, —NO, —NO$_2$, =N$_2$, N$_3$, —NHC(=O)R, —NHS(=O)$_2$R, —C(=O)R, —C(=O)NRR—S(=O)$_2$O—, —S(=O)$_2$OH, S(=O)$_2$R, —OS(=O)$_2$OR, —S(=O)$_2$NR, —S(=O)R, —OP(=O)(OR)$_2$, —P(=O)(OR)$_2$, P(=O)(O—)$_2$, —P(=O)(OH)$_2$, —P(O)(OR)(O—), —C(=O)R, —C(=O)OR, —C(=O)X, —C(S)R, —C(O)OR, —C(O)O—, —C(S)OR, —C(O)SR, —C(S)SR, —C(O)NRR, —C(S)NRR, —C(=NR)NRR, where each X is independently a halogen: F, Cl, Br, or I; and each R is independently H, alkyl, aryl, arylalkyl, a heterocycle, or a protecting group. Alkylene, alkenylene, and alkynylene groups may also be similarly substituted. When the number of carbon atoms is designated for a substituted group, the number of carbon atoms refers to the group, not the substituent (unless otherwise indicated). For example, a C$_{1-4}$ substituted alkyl refers to a C$_{1-4}$ alkyl, which can be substituted with groups having more than, e.g., 4 carbon atoms.

The term "affinity pair", as used herein, refers to a pair of molecules or substances that associate with one another through a strong and/or specific biologic or chemical affinity interaction such as that between antigen and antibody, enzyme and substrate, or receptor and ligand or hydrophobic compound and hydrophobic resin and the like. Any of these substances, covalently linked to an insoluble support or immobilized in a gel, may serve as the sorbent allowing the interacting substance to be isolated from relatively impure samples. The technique of using this kind of associative interaction of the affinity pairs along with the use of insoluble support or gel, to separate, isolate or purify a substance is named affinity capture. This technique usually implies retaining the desired affinity-tagged biomolecule on the insoluble support or gel through the associative interaction with the other member of the affinity pair that is linked to the insoluble support and eluting the impurities or undesired byproducts that are not tagged in a liquid phase. The affinity capture may be performed by filtration of the insoluble material and separation from the filtrate followed by elution or cleavage of the desired purified biomolecule from the insoluble support, Non-limiting examples of affinity pairs include biotin/avidin, biotin/streptavidin, glutathione/GST, maltose/MBP (Maltose Binding Protein), diols/arylboronic acids, nickel or cobalt/histidines or thiols, cucurbiturils/adamantane, cyclodextrin/adamantane, fluoroalkyl/fluoroalkyl, and trityl/Cis resin.

The term "affinity tag", as used herein, may refer to one member of an affinity pair or to a moiety that has an intrinsic property (such as hydrophobicity, hydrophilicity, polarity, charges, fluorophilicity, etc.) that allows isolation or separation of a target molecule (e.g., an oligonucleotide) linked to the affinity tag using the intrinsic property. An affinity pair comprises an affinity tag and a recognition moiety that has a specific binding capability to the affinity tag. The affinity tag may be present in the target molecule (e.g., as a substituent) or attached to the target molecule via a linker (e.g., an orthoester linker). An affinity tag may also be covalently captured on a solid support. Non-limiting examples of an affinity tag include a fluorous affinity tag, a hydrophobic tag, a biotin tag, a cyclodextrin tag, an adamantane tag, a maltose, or a polyamine tag, charged tag etc. An affinity tag may also be a chemical functional group, optionally protected, which reacts selectively with a specific chemical functional group on a molecule which imparts an intrinsic property (such as hydrophobicity, hydrophilicity, polarity, charges, fluorophilicity, etc.) that allows isolation or separation of the newly linked target molecule, or which reacts selectively with a specific chemical functional group attached to a solid phase or affinity capture medium. Non-limiting examples of functional chemical tags include maleimide tag, alkyne tag, azido tag, hydrazide tag, amino tag, a diol tag and a thiol tag.

The term "recognition moiety" as used herein, refers to the second member of an affinity pair, which interacts specifically with the affinity tag.

The term "hydrophobic tag", as used herein, refers to a hydrophobic substituent or a combination of hydrophobic substituents that are carbon rich. The hydrophobicity of a substituent can be determined, measured or calculated through the value of its partition coefficient (log P). The partition coefficient (log P) of a substance defines the ratio of its solubility in two immiscible solvents, normally octanol:water. When this value is calculated rather than measured, it is called cLog P. A hydrophobic tag has a cLog P of at least 3 or a combination of two, three or four "partial hydrophobic tags" has a collective value of cLog P of at least 3. Non-limiting examples of hydrophobic tags include C$_6$-C$_{24}$ alkyl, C$_4$-C$_{24}$ alkenyl, C$_4$-C$_{24}$ alkynyl, carbocycles and aryls, trityls, lipids, steroids, adamantane. Fluoro substituents or fluorosubstituted groups can be used to increase the hydrophobicity of a hydrophobic tag. A hydrophobic tag comprises a least six carbon atoms. An orthoester linker that comprises a hydrophobic tag, includes an orthoester linker with one, two, three or four hydrophobic tags, each located on one of its four radical R groups. A hydrophobic orthoester linker also includes an orthoester linker with "partial hydrophobic tags" (i.e. with less than six carbons each) but when combined together comprise at least six carbons.

The term "fluorous tag", as used herein, refers to a perfluorinated or fluorinated substituent or to a combination of perfluorinated or fluorinated substituents for example a fluorosubstituted C$_1$-C$_{24}$ alkyl, a fluorosubstituted C$_2$-C$_{24}$ alkenyl, a fluorosubstituted C$_2$-C$_{24}$ alkynyl, a fluorosubstituted carbocyclyl and a fluorosubstituted aryl. A fluorous tag comprises a least seven fluorine atoms and three carbon atoms. An orthoester linker that comprises a fluorous tag, includes an orthoester linker with one, two, three or four fluorous tags, each located on one of its four radical R groups. A fluorous orthoester linker also includes an orthoester linker with "partial fluorous tags" i.e. with less than seven fluorous atoms and less than three carbons, but which when combined together comprise at least seven fluorine atoms and at least three carbons, and when combined all together don't exceed fifty-two fluorine atoms. A "fluorous tag" can act as a "hydrophobic tag" and can be isolated using a hydrophobic medium rather than a fluorous medium.

The term "chromatographic method" refers to a method of separating one or more compounds involving the use of a stationary phase and a mobile phase or eluent that moves through or across the stationary phase. Non-limiting examples of chromatographic methods include fluorous affinity purification, high performance liquid chromatography, and gas chromatography.

The term "fluorous affinity purification" refers to an affinity-based method for purifying a target molecule having a fluorous affinity tag utilizing a fluorinated material (e.g., a fluorinated or perfluorinated adsorbent or fluorinated or perfluorinated resin) as a separation medium. The method is based on the strong affinity between fluorous tags and fluorinated materials such as fluorinated adsorbents.

The term "alkyl" refers to a straight-chain or branched alkyl, preferably having 1, 2, 3, 4, 5, 6, 7, 8, 9, 10, 11, 12, 13, 14, 15, 16, 17, 18, 19, 20, 21, 22, 23 or 24 carbons. Examples of such alkyl groups include methyl, ethyl, propyl, isopropyl, n-butyl, sec-butyl, isobutyl, tert-butyl, pentyl, isoamyl, hexyl, and the like. In some embodiments, an alkyl group may be a cycloalkyl group.

Alkyl groups may be unsubstituted or substituted, as defined above. The term "halosubstituted alkyl" refers to an alkyl group substituted with one or more halogen atoms. Nonlimiting examples include trifluoromethyl, trifluoroethyl, pentafluoroethyl, 2,2,2-trichloroethyl, chloromethyl, and the like. Halosubstituted alkyl groups may be unsubstituted or substituted, as defined above. The term "fluorosubstituted alkyl" refers to an alkyl group substituted with one or more fluorine atoms.

The term "alkenyl" refers to a straight or branched hydrocarbon, preferably having 2, 3, 4, 5, 6, 7, 8, 9, 10, 11, 12, 13, 14, 15, 16, 17, 18, 19, 20, 21, 22, 23 or 24 carbons, and having one or more carbon-carbon double bonds. Nonlimiting examples of alkenyl groups include ethenyl, 1-propenyl, 2-propenyl (allyl), iso-propenyl, 2-methyl-1-propenyl, 1-butenyl, and 2-butenyl. Alkenyl groups may be unsubstituted or substituted by one or more suitable substituents, as defined above. The term "halosubstituted alkenyl" refers to an alkenyl group substituted with one or more halogen atoms. The term "fluorosubstituted alkenyl" refers to an alkenyl group substituted with one or more fluorine atoms.

The term "alkynyl" refers to a straight or branched hydrocarbon, preferably having 2, 3, 4, 5, 6, 7, 8, 9, 10, 11, 12, 13, 14, 15, 16, 17, 18, 19, 20, 21, 22, 23 or 24 carbons, and having one or more carbon-carbon triple bonds. Alkynyl groups include, but are not limited to, ethynyl, propynyl, and butynyl. Alkynyl groups may be unsubstituted or substituted by one or more suitable substituents, as defined above. The term "halosubstituted alkynyl" refers to an alkynyl group substituted with one or more halogen atoms. The term "fluorosubstituted alkynyl" refers to an alkynyl group substituted with one or more fluorine atoms.

"Carbocycle" or "carbocyclyl" refers to a saturated (i.e., cycloalkyl), partially unsaturated (e.g., cycloakenyl, cycloalkadienyl, etc.) or aromatic ring having 3 to 7 carbon atoms as a monocycle, 7 to 12 carbon atoms as a bicycle, and up to about 20 carbon atoms as a polycycle. Monocyclic carbocycles have 3 to 6 ring atoms, still more typically 5 or 6 ring atoms. Bicyclic carbocycles have 7 to 12 ring atoms, e.g., arranged as a bicyclo[4,5], [5,5], [5,6] or [6,6] system, or 9 or 10 ring atoms arranged as a bicyclo[5,6] or [6,6] system, or spiro-fused rings. Non-limiting examples of monocyclic carbocycles include cyclopropyl, cyclobutyl, cyclopentyl, 1-cyclopent-1-enyl, 1-cyclopent-2-enyl, 1-cyclopent-3-enyl, cyclohexyl, 1-cyclohex-1-enyl, 1-cyclohex-2-enyl, 1-cyclohex-3-enyl, and phenyl. Non-limiting examples of bicyclo-carbocycles includes naphthyl.

"Heteroalkyl", "heteroalkenyl" and "heteroalkynyl" refers respectively to an alkyl group, an alkenyl group and an alkynyl group, in which one or more carbon atoms have been replaced with a heteroatom, such as, O, N, or S. Any carbons within the alkyl group, the alkenyl group or the alkynyl group can be replaced independently with a heteroatom (O, N, or S), meaning the first carbon, the terminal carbon or an internal carbon. For example, if the carbon atom of an alkyl group which is attached to the parent molecule is replaced with a heteroatom (e.g., O, N, or S) the resulting heteroalkyl groups are, respectively, an alkoxy group (e.g., —OCH$_3$, etc.), an amine alkyl (e.g., —NHCH$_3$, —N(CH$_3$)$_2$, etc.), or a thioalkyl group (e.g., —SCH$_3$). If a non-terminal carbon atom of the alkyl group which is not attached to the parent molecule is replaced with a heteroatom (e.g., O, N, or S) the resulting heteroalkyl groups are, respectively, an alkyl ether (e.g., —CH$_2$CH$_2$—O—CH$_3$, etc.), an alkyl amine (e.g., —CH$_2$NHCH$_3$, —CH$_2$N(CH$_3$)$_2$, etc.), or a thioalkyl ether (e.g., —CH$_2$—S—CH$_3$). If a terminal carbon atom of the alkyl group is replaced with a heteroatom (e.g., O, N, or S), the resulting heteroalkyl groups are, respectively, a hydroxyalkyl group (e.g., —CH$_2$CH$_2$—OH), an aminoalkyl group (e.g., —CH$_2$NH$_2$), or an alkyl thiol group (e.g., —CH$_2$CH$_2$—SH). A heteroalkyl group, a heteroalkenyl group, or an heteroalkynyl group can have, for example, 1 to 24 carbon atoms. A $C_1$-$C_6$ heteroalkyl group means a heteroalkyl group having 1 to 6 carbon atoms. A "substituted heteroalkyl", a "substituted heteroalkenyl", or a "substituted heteroalkynyl" means a heteroalkyl, a heteroalkenyl or a heteroalkynyl as defined herein in which one or more hydrogen atom has been replaced with a non-hydrogen substituent as defined in the "substituted" definition.

The term "aryl" refers to an unsubstituted or substituted aromatic carbocyclic substituent, as commonly understood in the art, having 3 to 7 carbon atoms as a monocycle, 7 to 12 carbon atoms as a bicycle, and up to about 20 carbon atoms as polycycle such as phenyl, naphthyl, anthracyl, indanyl, and the like. It is understood that the term aryl applies to cyclic substituents that are planar and comprise 4n+2 electrons, according to Hückel's Rule. Aryl groups may be unsubstituted or substituted by one or more suitable substituents, as defined above. The term "halosubstituted aryl" refer to aryl substituted with one or more halogen atoms or halogen-containing substituents. The term "fluorosubstituted aryl" refer to aryl substituted with one or more fluorine atoms or fluorine-containing substituents.

"Arylalkyl" refers to an acyclic alkyl group in which one of the hydrogen atoms bonded to a carbon atom, typically a terminal carbon atom, is replaced with an aryl group. Typical arylalkyl groups include, but are not limited to, benzyl, 2-phenylethan-1-yl, naphthylmethyl, 2-naphthylethan-1-yl, naphthobenzyl, 2-naphthophenylethan-1-yl and the like. The arylalkyl group can comprise 6 to 24 carbon atoms, e.g., the alkyl carbon atoms and the aryl carbon atoms add up to 6 to 24 carbon atoms. Aryl groups may be unsubstituted or substituted by one or more suitable substituents, as defined above.

The term "carbonyl" refers to a substituent comprising a carbon double bonded to an oxygen. Examples of such substituents include aldehydes, ketones, carboxylic acids, esters, amides, carbonates, and carbamates. Carbonyl groups may be unsubstituted or substituted by one or more suitable substituents, as defined above.

The term "amino" refers to any nitrogen-containing moiety. Non-limiting examples of the amino group are NH$_2$— (primary), RHN— (secondary), and R$_2$N (tertiary) where R is alkyl, alkenyl, alkynyl, aryl, heterocyclic, or heteroaryl. RHN— and R$_2$N groups may be unsubstituted or substituted, as defined above.

The term "heteroaryl" refers to a monocyclic or bicyclic 5- or 6-membered ring system, wherein the heteroaryl group is unsaturated and satisfies Hückel's rule. Non-limiting examples of heteroaryl groups include furanyl, thiophenyl, pyrrolyl, pyrazolyl, imidazolyl, 1,2,3-triazolyl, 1,2,4-triazolyl, isoxazolyl, oxazolyl, isothiazolyl, thiazolyl, 1,3,4-oxadiazol-2-yl, 1,2,4-oxadiazol-2-yl, 5-methyl-1,3,4-oxadiazole, 3-methyl-1,2,4-oxadiazole, pyridinyl, pyrimidinyl, pyrazinyl, triazinyl, benzofuranyl, benzothiophenyl, indolyl, quinolinyl, isoquinolinyl, benzimidazolyl, benzoxazolinyl, benzothiazolinyl, quinazolinyl, and the like. Heteroaryl groups may be unsubstituted or substituted, as defined above.

The term "heterocycle" or "heterocyclyl" refers to a monocyclic, bicyclic, or tricyclic moiety containing 1 to 4 heteroatoms selected from O, N, and S. Heterocyclyl groups optionally contain one or more double bonds. Heterocyclyl groups include, but are not limited to, azetidinyl, tetrahydrofuranyl, imidazolidinyl, pyrrolidinyl, piperidinyl, piperazinyl, oxazolidinyl, thiazolidinyl, pyrazolidinyl, thiomorpholinyl, tetrahydrothiazinyl, tetrahydro-thiadiazinyl, morpholinyl, oxetanyl, tetrahydrodiazinyl, oxazinyl, oxathiazinyl, indolinyl, isoindolinyl, quinuclidinyl, chromanyl, isochromanyl, and benzoxazinyl. Nonlimiting examples of monocyclic saturated or partially saturated ring systems are tetrahydrofuran-2-yl, tetrahydrofuran-3-yl, imidazolidin-1-yl, imidazolidin-2-yl, imidazolidin-4-yl, pyrrolidin-1-yl, pyrrolidin-2-yl, pyrrolidin-3-yl, piperidin-1-yl, piperidin-2-yl, piperidin-3-yl, piperazin-1-yl, piperazin-2-yl, piperazin-3-yl, 1,3-oxazolidin-3-yl, isothiazolidine, 1,3-thiazolidin-3-yl, 1,2-pyrazolidin-2-yl, 1,3-pyrazolidin-1-yl, thiomorpholin-yl, 1,2-tetrahydrothiazin-2-yl, 1,3-tetrahydrothiazin-3-yl, tetrahydrothiadiazin-yl, morpholin-yl, 1,2-tetrahydrodiazin-2-yl, 1,3-tetrahydrodiazin-1-yl, 1,4-oxazin-2-yl, and 1,2,5-oxathiazin-4-yl. Heterocyclic groups may be unsubstituted or substituted by one or more suitable substituents, as defined above.

"Halogen" or "halo" refers to fluorine, chlorine, bromine, and iodine.

A "nucleotide" refers to a sub-unit of a nucleic acid (whether DNA or RNA or analogue thereof) which includes a phosphate group, a sugar group and a heterocyclic base, as well as analogs of such sub-units. Other groups (e.g., protecting groups) can be attached to any component(s) of a nucleotide. A "nucleoside" or "nucleoside moiety" referred to a nucleic acid subunit including a sugar group and a heterocyclic base, as well as analogs of such sub-units.

The terms "nucleoside" and "nucleotide" are intended to include those moieties that contain not only the known purine and pyrimidine bases, e.g. adenine (A), thymine (T), cytosine (C), guanine (G), or uracil (U), but also other heterocyclic bases that have been modified. The pyrimidine, purine, heterocyclic base and modified heterocyclic bases are termed herein "nucleobases". Such modifications include methylated purines or pyrimidines, acylated purines or pyrimidines, alkylated heterocycles or other heterocycles. Such modifications include, by way of examples, diaminopurine and its derivatives, inosine and its derivatives, alkylated purines or pyrimidines, acylated purines or pyrimidines, thiolated purines or pyrimidines, and the like, or the addition of a protecting group such as acetyl, difluoroacetyl, trifluoroacetyl, isobutyryl, benzoyl, 9-fluorenylmethoxycarbonyl, phenoxyacetyl, dimethylformamidine, dibutylformamidine, N,N-diphenyl carbamate, or the like. In addition, the terms "nucleoside" and "nucleotide" include those moieties that contain not only conventional ribose and deoxyribose sugars, but other sugars as well. Modified nucleosides or nucleotides also include modifications on the sugar moiety, e.g., wherein one or more of the hydroxyl groups are replaced with halogen atoms or aliphatic groups, or are functionalized as ethers, amines, or the like. Modified nucleosides or nucleotides also include modifications on the internucleotide linkage or backbone moiety. "Analogues" refer to molecules having structural features that are recognized in the literature as being mimetics, derivatives, having analogous structures, or other like terms, and include, for example, polynucleotides incorporating non-natural (not usually occurring in nature) nucleotides, unnatural nucleotide mimetics such as 2'-modified nucleosides, peptide nucleic acids, oligomeric nucleoside phosphonates, and any polynucleotide that has added substituent groups, such as protecting groups or linking groups.

An "oligonucleotide" refers to a compound containing a plurality of nucleoside moiety subunits that are linked by internucleotide bonds. As such, the term also refers to a compound containing a plurality of nucleotide moiety subunits or residues. An oligonucleotide might contain ribonucleosides, or deoxyribonucleosides or a mixture thereof. An oligonucleotide may comprise natural and/or non-natural nucleosides, nucleoside analogs and modified nucleosides.

The term "linker" as used herein refers to a hydrocarbyl chain (e.g., $(C_1-C_{12})$alkylene, $(C_2-C_{12})$alkenylene, $(C_2-C_{12})$alkynylene), optionally substituted with a substituent group, or interspersed with other atoms, as represented by —(CHR')a-Wb-(CHR')c-Vd-(CHR')e-, wherein W and V are independently —O—, —S—, or —NR'—; R' is H or $(C_1-C_6)$alkyl; a, b, c, d, and e are independently an integer from 0 to 10, preferably from 0 to 6, or preferably from 0 to 3, and the sum of a, b, c, d, and e is preferably an integer from 2 to 6. The hydrocarbyl chain may be interspersed with —O—R", —O—CO—R", —NR'—R", —NR'—CO—R", —CO—NR'—R", —CO—R", or a combination thereof, wherein R' and R" are independently H or $(C_1-C_6)$hydrocarbyl.

The term "orthoester linker" refers to an orthoester compound that is capable of attaching to a biopolymer such as an oligonucleotide. In some embodiments, the orthoester linker comprises an affinity tag.

The term "oligonucleotide-orthoester linker conjugate" refers to the product that results from reaction of an oligonucleotide oxygen with an orthoester linker.

The term "fluorous orthoester" refers to an orthoester comprising at least one fluorous tag.

A "thionocarbamate protecting group" refers to a protecting group that includes a thionocarbonyl with a nitrogen and an oxygen bonded to the thionocarbonyl carbon atom: —O—C(S)N—.

The term "electron withdrawing group" refers to a chemical group that draws electrons away from a reaction center. Nonlimiting examples of electron withdrawing groups (EWG) are halogens (e.g., fluorine and chlorine), haloalkyls (e.g. $CH_2Cl$, $CF_3$ and the like), nitriles (—RCN), carbonyls (—COR), sulfonyls (—$SO_3R$), ammonium ($N^+R_3$) and nitro groups (—$NO_2$).

The term "truncated sequence" or "truncated oligonucleotide" refers to an oligonucleotide sequence that is shorter in length than a target full length oligonucleotide.

As used in the specification and appended claims, and in addition to their ordinary meanings, the terms "substantial" or "substantially" mean to within acceptable limits or degree to one having ordinary skill in the art. For example, "substantially cancelled" means that one skilled in the art considers the cancellation to be acceptable.

As used in the specification and the appended claims and in addition to its ordinary meaning, the terms "approximately" and "about" mean to within an acceptable limit or amount to one having ordinary skill in the art. The term "about" generally refers to plus or minus 15% of the indicated number. For example, "about 10" may indicate a range of 8.5 to 11.5. For example, "approximately the same"

means that one of ordinary skill in the art considers the items being compared to be the same.

In the present disclosure, numeric ranges are inclusive of the numbers defining the range. It should be recognized that chemical structures and formula may be elongated or enlarged for illustrative purposes.

Whenever a range of the number of atoms in a structure is indicated (e.g., a $C_1$-$C_{24}$ alkyl, $C_2$-$C_{24}$ alkenyl, $C_2$-$C_{24}$ alkynyl, etc.), it is specifically contemplated that the substituent can be described by any of the carbon atoms in the sub-range or by any individual number of carbon atoms falling within the indicated range. By way of example, a description of the group such as an alkyl group using the recitation of a range of 1-24 carbon atoms (e.g., $C_1$-$C_{24}$), 1-6 carbon atoms (e.g., $C_1$-$C_6$), 1-4 carbon atoms (e.g., $C_1$-$C_4$), 1-3 carbon atoms (e.g., $C_1$-$C_3$), or 2-24 carbon atoms (e.g., $C_2$-$C_{24}$) encompasses and specifically describes an alkyl group having any of 1, 2, 3, 4, 5, 6, 7, 8, 9, 10, 11, 12, 13, 14, 15, 16, 17, 18, 19, 20, 21, 22, 23 and 24 carbon atoms, as appropriate, as well as any sub-range thereof (e.g., 1-2 carbon atoms, 1-3 carbon atoms, 1-4 carbon atoms, 1-5 carbon atoms, 1-6 carbon atoms, 1-7 carbon atoms, 1-8 carbon atoms, 1-9 carbon atoms, 1-10 carbon atoms, 1-11 carbon atoms, 1-12 carbon atoms, 1-13 carbon atoms, 1-14 carbon atoms, 1-15 carbon atoms, 1-24 carbon atoms, 2-3 carbon atoms, 2-4 carbon atoms, 2-5 carbon atoms, 2-6 carbon atoms, 2-7 carbon atoms, 2-8 carbon atoms, 2-9 carbon atoms, 2-10 carbon atoms, 2-11 carbon atoms, 2-12 carbon atoms, 2-13 carbon atoms, 2-14 carbon atoms, 2-15 carbon atoms, 2-16 carbon atoms, 3-4 carbon atoms, 3-5 carbon atoms, 3-6 carbon atoms, 3-7 carbon atoms, 3-8 carbon atoms, 3-9 carbon atoms, 3-10 carbon atoms, 3-11 carbon atoms, 3-12 carbon atoms, 3-13 carbon atoms, 3-14 carbon atoms 3-15 carbon atoms, 3-16 carbon atoms, 3-17 carbon atoms, 3-18 carbon atoms, 3-19 carbon atoms, 3-20 carbon atoms, 3-21 carbon atoms, 3-22 carbon atoms, 3-23 carbon atoms and/or 3-24 carbon atoms, as appropriate).

Unless defined otherwise, all technical and scientific terms used herein have the same meaning as commonly understood by those working in the fields to which this disclosure pertain.

DETAILED DESCRIPTION

Before the various embodiments are described, it is to be understood that the teachings of this disclosure are not limited to the particular embodiments described, and as such can, of course, vary. It is also to be understood that the terminology used herein is for the purpose of describing particular embodiments only, and is not intended to be limiting, since the scope of the present teachings will be limited only by the appended claims.

As disclosed herein, a number of ranges of values are provided. It is understood that each intervening value, to the tenth of the unit of the lower limit, unless the context clearly dictates otherwise, between the upper and lower limits of that range is also specifically disclosed. Each smaller range between any stated value or intervening value in a stated range and any other stated or intervening value in that stated range is encompassed within the invention. The upper and lower limits of these smaller ranges may independently be included or excluded in the range, and each range where either, neither, or both limits are included in the smaller ranges is also encompassed within the invention, subject to any specifically excluded limit in the stated range. Where the stated range includes one or both of the limits, ranges excluding either or both of those included limits are also included in the invention.

Unless defined otherwise, all technical and scientific terms used herein have the same meaning as commonly understood by one of ordinary skill in the art to which this disclosure pertains. Although any methods and materials similar or equivalent to those described herein can also be used in the practice or testing of the present teachings, some exemplary methods and materials are now described.

All patents and patent publications referred to herein are expressly incorporated by reference.

As used in the specification and appended claims, the terms "a," "an," and "the" include both singular and plural referents, unless the context clearly dictates otherwise. Thus, for example, "a moiety" includes one moiety and plural moieties.

Methods and compounds are provided that can be used to purify oligonucleotides such as RNA, DNA or chimera. The present methods involve the conjugation of oligonucleotides with an orthoester linker, and purification of the resulting oligonucleotide-orthoester linker conjugate using, e.g., chromatographic separation or affinity capture. The present methods and compounds are especially useful for separating full-length oligonucleotides from truncated or failure sequences. The present methods provide high resolution of oligonucleotides of similar size, allowing for rapid separation of oligonucleotides from undesired side-products. Another advantage of the present method is that oligonucleotide-orthoester linker conjugates are base-stable, allowing for synthetic manipulation of the oligonucleotide-orthoester linker conjugate under basic conditions without the risk of cleavage of the orthoester from the oligonucleotide. After performing an affinity purification of the oligonucleotide-orthoester linker conjugate on a separation medium (gel or resin), the oligonucleotide-orthoester linker conjugate may be cleaved under mildly acidic conditions, releasing the purified oligonucleotide in high yield. The present methods are effective for purifying oligonucleotides prepared by various synthetic methods, including oligonucleotides prepared in a solid-phase oligonucleotide synthesis.

An oligonucleotide to be purified may be obtained from a natural source or prepared using a synthetic method. Synthetic oligonucleotides may be prepared using any method known in the art. In some embodiments, an oligonucleotide is prepared via solid-phase oligonucleotide synthesis. In such embodiments, the synthesis is carried out on a solid support. The solid support is generally held between two filters in columns that enable reagents and solvents to pass through freely.

In some embodiments, the synthesis is carried out on a planar surface. In some embodiments, the synthesis is carried out on a non-planar surface. In such embodiments, the synthesis is carried out on a substantially solid, substantially smooth surface. The term "substantially solid," as used herein for a surface, means that the location(s) on the surface of the support where oligonucleotide synthesis is occurring is resistant to the diffusion, absorption, or permeation of the relevant reagents and chemicals of oligonucleotide synthesis beyond the surface and into the body of the support (in contrast to commercial polymeric oligo synthesizer supports, which permit such diffusion and permeation, such that oligo synthesis occurs in the body of the support). The term "substantially smooth," as used herein for a surface, means that the location(s) on the surface of the support where oligonucleotide synthesis is occurring is at most superficially irregular, such that irregularities, if any, are not of a scale which would substantially affect the rapidity with which reagents can be uniformly applied to, mixed on, or removed from the surface (in contrast to commercial "controlled pore glass" oligo synthesizer supports, which contain pores and irregularities that slow the application and removal of reagents). A substantially solid, substantially smooth surface need not be flat, and would include, for example, flat surfaces, tubes, cylinders, arrays of depressions or wells, and combinations of these elements, as well as other designs presenting surface portions with the above-described attributes. For example, substantially solid, substantially smooth surfaces are surfaces (or portions of surfaces) that can be addressed by an inkjet print head.

In some embodiments, an oligonucleotide is attached to a solid support such as a controlled-pore glass, or a polymeric support for example a polystyrene (PS) support. Suitable solid supports are in some cases polymeric, and may have a variety of forms and compositions and derive from naturally occurring materials, naturally occurring materials that have been synthetically modified, or synthetic materials. Examples of suitable support materials include, but are not limited to, polysaccharides such as agarose (e.g., that available commercially as Sepharose®, from Pharmacia) and dextran (e.g., those available commercially under the tradenames Sephadex® and Sephacryl®, also from Pharmacia), polyacrylamides, polystyrenes, polyvinyl alcohols, copolymers of hydroxyethyl methacrylate and methyl methacrylate, silicas, teflons, glasses, and the like.

In some embodiments, the oligonucleotide is prepared using the phosphoramidite method. In some embodiments, the oligonucleotide synthesis method comprises a support-bound nucleoside having a 5'-DMT protecting group.

In some embodiments, the oligonucleotide synthesis method comprises a support-bound nucleoside having a 3'-DMT protecting group. In some embodiments, the oligonucleotide synthesis method comprises a support-bound nucleoside having a 5'-silyl protecting group. In some embodiments, the oligonucleotide synthesis method comprises a support-bound nucleoside having an oxidation removable protecting group. In some embodiments, the oligonucleotide synthesis comprises the steps of detritylation, coupling of a support bound nucleoside with a nucleoside phosphoramidite monomer, capping unreacted 5'-hydroxyl groups, and phosphoramidite oxidation. In some embodiments, the oligonucleotide synthesis is automated. In some embodiments, the oligonucleotide is detritylated prior to performing a method of the present invention.

In an embodiment, the invention provides a method of purifying an oligonucleotide. The method comprises synthesizing an oligonucleotide on a solid support; reacting the oligonucleotide with an orthoester linker to form an oligonucleotide-orthoester linker conjugate, wherein the orthoester linker comprises an affinity tag; cleaving the oligonucleotide-orthoester linker conjugate from the solid support used for synthesis; isolating the oligonucleotide-orthoester linker conjugate using a chromatographic or affinity capture method; and cleaving the orthoester linker from the oligonucleotide orthoester linker conjugate, thereby releasing a purified oligonucleotide.

In some embodiments, the present methods comprise reacting an oligonucleotide with an orthoester linker comprising an affinity tag and an alkoxyl leaving group. The reaction produces an oligonucleotide-orthoester linker conjugate comprising the oligonucleotide attached to the orthoester linker, where the orthoester linker is attached to the affinity tag. The affinity tag desirably has structural and/or functional group properties that can be exploited in a purification method for separating the oligonucleotide-orthoester linker conjugate from one or more impurities. For example, in some embodiments, an oligonucleotide-orthoester linker conjugate can be separated from one or more impurities using fluorous affinity chromatography.

In some embodiments, the orthoester linker is a cyclic orthoester. In some embodiments, the cyclic orthoester is a five-membered cyclic orthoester. In some embodiments, the orthoester linker is a six-membered cyclic orthoester. In some embodiments, the orthoester linker is a seven-membered cyclic orthoester.

In some embodiments, the orthoester linker is a fluorous orthoester. In some embodiments, the orthoester linker comprises at least one fluorine atom, at least two fluorine atoms, at least three fluorine atoms, at least four fluorine atoms, at least five fluorine atoms, at least six fluorine atoms, at least seven fluorine atoms, at least eight fluorine atoms, at least nine fluorine atoms, at least ten fluorine atoms, at least eleven fluorine atoms, at least twelve fluorine atoms, at least thirteen fluorine atoms, at least fourteen fluorine atoms, at least fifteen fluorine atoms, at least seventeen fluorine atoms, at least nineteen fluorine atoms, at least twenty-one fluorine atoms, at least twenty-three fluorine atoms or at least twenty-five fluorine atoms or up to but not more than fifty-two fluorine atoms.

In some embodiments, the orthoester linker is a compound (Ia) of formula RC(OR')(OR'')(OR'''),

(Ia)

wherein each of R, R', R'', and R''' is independently a $C_1$-$C_{24}$ alkyl, a $C_2$-$C_{24}$ alkenyl, a $C_2$-$C_{24}$ alkynyl, a halosubstituted alkyl, a halosubstituted alkenyl, a halosubstituted alkynyl, an alkyl, an alkenyl, an alkynyl, a carbocyclyl, a heteroalkyl, an aryl, a heteroaryl, a heterocycle or any substituted equivalents. R may be a hydrogen.

In some embodiments, the orthoester linker is the compound of the formula (Ia), wherein each of R, R', R'', and R''' is independently a $C_1$-$C_{24}$ alkyl, a $C_2$-$C_{24}$ alkenyl, a $C_2$-$C_{24}$ alkynyl, a halosubstituted $C_1$-$C_{24}$ alkyl, a halosubstituted $C_2$-$C_{24}$ alkenyl, a halosubstituted $C_2$-$C_{24}$ alkynyl, a carbocyclyl, a heteroalkyl, an aryl, a heteroaryl, a heterocycle or any substituted equivalents, with a proviso that R may be a hydrogen.

In some embodiments, the orthoester linker is the compound of formula (La) wherein R is H or $C_1$-$C_3$ alkyl and R', R'', R''' are each independently an aryl or a substituted aryl.

In some embodiments, R is H or $CH_3$ and R', R'', R''' are all phenyl or a substituted phenyl.

In some embodiments, one of the R', R'' and R''' is a leaving group and may comprise an electron withdrawing group "EWG" for example a trifluoroalkyl, a halogen (e.g. a chlorine) or a cyanoethyl group. In some embodiments, R, R', R'', and R''' are methyl or ethyl.

In some embodiments, the orthoester linker is a compound of formula (Ia) wherein at least one of R, R', R'', and R''' is a hydrophobic tag or a partial hydrophobic tag and the remaining of the Rs groups is $C_1$-$C_6$ alkyl, $C_2$-$C_6$ alkenyl, $C_2$-$C_6$ alkynyl, halo- or hetero-substituted equivalents, $C_3$-$C_{12}$ carbocyclyl or heterocyclyl and substituted equivalents.

In some embodiments, at least two of R, R', R", and R'" are a hydrophobic tag or a partial hydrophobic tag and the remaining of the Rs groups is $C_1$-$C_6$ alkyl, $C_2$-$C_6$ alkenyl, $C_2$-$C_6$ alkynyl, halo- or hetero-substituted equivalents, $C_3$-$C_{12}$ carbocyclyl or heterocyclyl and substituted equivalents.

In the embodiments in which the orthoester linker is a compound of formula (Ia) wherein at least one or two of R, R', R", and R'" is a hydrophobic tag or a partial hydrophobic tag, the hydrophobic tag refers to a straight, branched, mono- or poly-cyclic, saturated, partially unsaturated or unsaturated $C_1$-$C_{24}$ hydrocarbon chain that is optionally substituted with F, Cl, Br, I or $C_1$-$C_3$ alkyls and optionally interspersed with heteroatoms independently selected from: O, S, and N, or interspersed with groups independently selected from $NR^a$—$R^b$, —$NR^a$—CO—$R^b$, —CO—$NR^a$—$R^b$, —CO—$R^a$ wherein $R^a$, $R^b$ are each independently H or $C_1$-$C_6$ alkyl. Taking alone or together, the hydrophobic tag or the sum of partial hydrophobic tags has a cLog P value of at least 3. In some embodiments the total number of carbon atoms shared between R, R', R" and R'" is not greater than 50. In some embodiment, R is a hydrogen. In some embodiments, R, is methyl or ethyl.

In some embodiments, the orthoester linker compound (Ia) is selected from the two structures below:

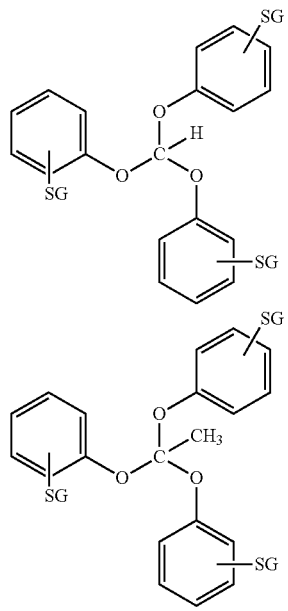

wherein SG is 0, 1, 2, 3, 4 or 5 substituent groups, independently present or absent on each phenyl group, and independently selected from halogen, $NO_2$, methyl and methoxy group. Preferably, at least two of the substituted phenyl groups are the same.

In a preferred embodiment, SG is absent on the three phenyl groups.

In some embodiments, the orthoester linker is a compound of formula (Ia) wherein at least one of R, R', R", and R'" is a fluorous tag or a partial fluorous tag and the remaining of the other Rs groups is $C_1$-$C_6$ alkyl, $C_2$-$C_6$ alkenyl, $C_2$-$C_6$ alkynyl, halo- or hetero-substituted equivalents, $C_3$-$C_{12}$ carbocyclyl or heterocyclyl and substituted equivalents.

A fluorous tag refers to a straight, branched, mono- or poly-cyclic, saturated, partially unsaturated or unsaturated $C_1$-$C_{24}$ hydrocarbon chain that is partially or fully (perfluoro) substituted with fluorine atoms, optionally substituted with Cl, Br, I or $C_1$-$C_3$ alkyls and optionally interspersed with heteroatoms independently selected from: O, S, N, or interspersed with groups independently selected from $NR^a$—$R^b$, —$NR^a$—CO—$R^b$, —CO—$NR^a$—$R^b$, —CO—$R^a$ wherein $R^a$, $R^b$ are each independently H or $C_1$-$C_6$ alkyl. In a fluorous tag, the total number of carbons shared between R, R', R" and R'" is at least 3 and the total number of fluorine atoms is at least 7.

In some embodiments, the orthoester linker is compound (Ia) wherein R is H or $C_1$-$C_3$ alkyl and R', R", R'" are each independently $C_2$-$C_{12}$ fluoroalkyl.

In some embodiments, the orthoester linker compound (Ia) has the structure of the compounds below:

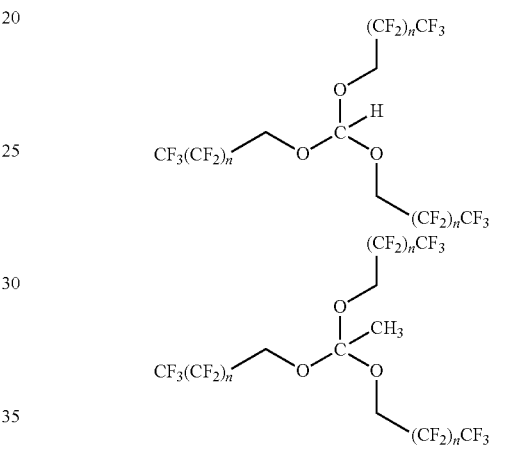

Wherein n is an integer selected from 1 to 5.

In some embodiments, the orthoester linker comprises at least one affinity tag (AfTg). In some embodiments, the affinity tag (AfTg) may be a part or the totality of the chemical structure of an R group of the orthoester linker as described above (e.g. hydrophobic or fluorous tags).

In some embodiments, the affinity tag (AfTg) is not a hydrophobic or a fluorous tag, and is for example a biotin tag, a maltose tag, an adamantane tag or a chemical functional tag and may be attached directly through a covalent bond or indirectly through a linker L to the orthoester linker. In these embodiments, the orthoester linker is a compound of formula (Ib)

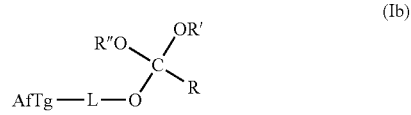

wherein R, R', R" are each independently AfTg-L or a straight, branched, mono- or poly-cyclic, saturated, partially unsaturated or unsaturated $C_1$-$C_{12}$ hydrocarbon chain that is optionally substituted and optionally interspersed with heteroatoms independently selected from: O, S, N, or with groups independently selected from $NR^a$—$R^b$, —$NR^a$—CO—$R^b$, —CO—$NR^a$—$R^b$, —CO—$R^a$ wherein $R^a$, $R^b$ are each independently H or $C_1$-$C_6$ alkyl; and wherein L is a covalent bond or a straight, branched, mono- or poly-cyclic, saturated, partially unsaturated or unsaturated $C_1$-$C_{12}$ hydrocarbon chain that is optionally substituted with F, Cl, Br, I or $C_1$-$C_3$ alkyls and optionally interspersed with heteroatoms independently selected from: O, S, N, or with groups independently selected from $NR^a$—$R^b$, —$NR^a$—CO—$R^b$, —CO—$NR^a$—$R^b$, —CO—$R^a$ wherein $R^a$, $R^b$ are each independently H or $C_1$-$C_6$ alkyl.

In some embodiments, L is a straight, branched, mono- or poly-cyclic, saturated, partially unsaturated or unsaturated $C_1$-$C_{12}$ hydrocarbon chain that is optionally substituted with F, Cl, Br, I or $C_1$-$C_3$ alkyls and optionally interspersed with heteroatoms independently selected from: O, S, N, or with groups independently selected from $NR^a$—$R^b$, —$NR^a$—CO—$R^b$, —CO—$NR^a$—$R^b$, —CO—$R^a$ wherein $R^a$, $R^b$ are each independently H or $C_1$-$C_6$ alkyl, and R, R' and R" are each independently $C_1$-$C_6$ alkyl, $C_2$-$C_6$ alkenyl, $C_2$-$C_6$ alkynyl, halo- or hetero-substituted equivalents, $C_3$-$C_{12}$ carbocyclyl or heterocyclyl and substituted equivalents. R may be a hydrogen. In some embodiments, one of the R' and R" is a leaving group and may comprise an electron withdrawing group EWG for example a trifluoroalkyl (e.g. $CH_2CF_3$) or a cyanoethyl group.

In some embodiments, the orthoester linker is the compound of formula (Ib), wherein AfTg is an affinity tag and R, R', R" are each independently AfTg-L or a $C_1$-$C_{24}$ alkyl, a $C_2$-$C_{24}$ alkenyl, a $C_2$-$C_{24}$ alkynyl, a halosubstituted $C_1$-$C_{24}$ alkyl, a halosubstituted $C_2$-$C_{24}$ alkenyl, a halosubstituted $C_2$-$C_{24}$ alkynyl, a carbocyclyl, a heteroalkyl, an aryl, a heteroaryl, a heterocycle, any substituted equivalents or a combination thereof provided that the total number of carbons doesn't exceed 24; and wherein L is a covalent bond or a straight, branched, mono- or poly-cyclic, saturated, partially unsaturated or unsaturated $C_1$-$C_{12}$ hydrocarbon chain that is optionally substituted with F, Cl, Br, I or $C_1$-$C_3$ alkyls and optionally interspersed with heteroatoms independently selected from: O, S, N, or with groups independently selected from S—S, $NR^a$, $NR^a$—CO, —CO—$NR^a$—, $NR^a$—CO—$NR^b$, CO wherein $R^a$, $R^b$ are each independently H or $C_1$-$C_6$ alkyl.

In some embodiments, the orthoester linker is a compound of formula (Ic) wherein two of R', R", and R''' groups of the orthoester linker are linked together through a carbon-carbon bond and form a cyclic orthoester as shown below:

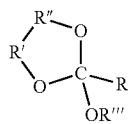

(Ic)

Upon reaction of the orthoester linker compound (Ia) with an oligonucleotide, an oligonucleotide-orthoester linker conjugate (IVa) is obtained.

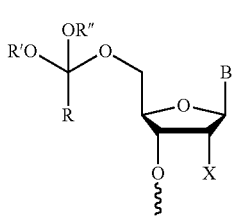

(IVa)

wherein at least one of R, R' and R" is a hydrophobic tag or a fluorous tag, wherein R, R' and R" are each independently a $C_1$-$C_{24}$ alkyl, a $C_2$-$C_{24}$ alkenyl, a $C_2$-$C_{24}$ alkynyl, a halosubstituted alkyl, a halosubstituted alkenyl, a halosubstituted alkynyl, a carbocyclyl, a heteroalkyl, an aryl, a heteroaryl, a heterocycle or any substituted equivalents; preferrably, R' and/or R" is a hydrophobic tag or a fluorous tag, R is H or methyl;

wherein X is H, OH, F, protected hydroxyl, O-methoxy or O-MOE (methoxyethoxy); and wherein B is a protected or unprotected nucleobase.

Upon reaction of the orthoester linker (Ib) with an oligonucleotide, an oligonucleotide-orthoester linker conjugate (IVb) is obtained.

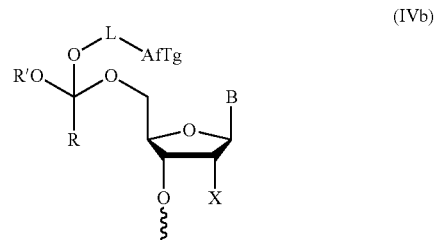

(IVb)

wherein AfTg is an affinity tag;

wherein L is a covalent bond or a straight, branched, mono- or poly-cyclic, saturated, partially unsaturated or unsaturated $C_1$-$C_{12}$ hydrocarbon chain that is optionally substituted with F, Cl, Br, I or $C_1$-$C_3$ alkyls and optionally interspersed with heteroatoms independently selected from: O, S, N, or with groups independently selected from $NR^a$—$R^b$, —$NR^a$—CO—$R^b$, —CO—$NR^a$—$R^b$, —CO—$R^a$ wherein $R^a$, $R^b$ are each independently H or $C_1$-$C_6$ alkyl;

wherein R and R' are each independently a $C_1$-$C_{24}$ alkyl, a $C_2$-$C_{24}$ alkenyl, a $C_2$-$C_{24}$ alkynyl, a halosubstituted alkyl, a halosubstituted alkenyl, a halosubstituted alkynyl, a carbocyclyl, a heteroalkyl, an aryl, a heteroaryl, a heterocycle or any substituted equivalents; and wherein X is H, OH, F, protected hydroxyl, O-methoxy or O-MOE (methoxyethoxy) and wherein B is a protected or unprotected nucleobase.

In preferred embodiments, R is H and R' is $C_1$-$C_6$ alkyl, $C_2$-$C_6$ alkenyl, $C_2$-$C_6$ alkynyl, halo- or hetero-substituted equivalents, $C_3$-$C_{12}$ carbocyclyl or heterocyclyl and substituted equivalents.

In some embodiments, an affinity purification is used to isolate or purify an oligonucleotide-orthoester linker conjugate.

In some embodiments, the orthoester linker reacts with the 5'-hydroxyl of an oligonucleotide, thereby attaching to the 5'-hydroxyl of the oligonucleotide. Thus, in some embodiments, the orthoester linker is attached at the 5'-hydroxyl of the oligonucleotide. In some embodiments, the orthoester linker reacts with the 3'-hydroxyl of an oligonucleotide, thereby attaching to the 3'-hydroxyl of the oligonucleotide. Thus, in some embodiments, the orthoester linker is attached at the 3'-hydroxyl of the oligonucleotide. In some embodiments, the orthoester linker is attached to a hydroxyl group present on a nucleotide base.

In some embodiments, the oligonucleotide is an oligoribonucleotide (RNA). In some embodiments, the oligonucleotide is an oligodeoxyribonucleotide (DNA). In some embodiments, the oligonucleotide is at least 15 nucleotides in length. In some embodiments, the oligonucleotide is at least 50 nucleotides in length. In some embodiments, the oligonucleotide is at least 70 nucleotides in length. In some embodiments, the oligonucleotide is at least 75 nucleotides in length. In some embodiments, the oligonucleotide is at least 100 nucleotides in length. In some embodiments, the oligonucleotide is at least 125 nucleotides in length. In some embodiments, the oligonucleotide is at least 150 nucleotides in length. In some embodiments, the oligonucleotide is from about 15 nucleotides to about 500 nucleotides in length. In some embodiments, the oligonucleotide is from about 40 nucleotides to about 300 nucleotides in length.

The affinity tag and the recognition moiety of the same affinity pair can be interchangeably linked to the biomolecule or biopolymer or to the insoluble support, and the choice will be made based upon the ease of the conjugation reaction and the compatibility of the conditions used to deprotect and cleave the tag from the biomolecule. Taking this into consideration, a skilled person can decide which member of the affinity pair will be attached to the biomolecule and to the solid support.

In some embodiments, the affinity tag is a fluorous affinity tag. Non-limiting examples of fluorous affinity tags include fluorinated substituents such as fluorosubstituted alkyl, fluorosubstituted heteroalkyl, fluorosubstituted alkenyl, fluorosubstituted alkynyl, fluorosubstituted carbocyclyl, fluorosubstituted heterocyclyl and a fluorosubstituted aryl substituents. In some embodiments, an orthoester acts as a linker between a fluorous affinity tag and an oligonucleotide. In other words, the orthoester (i.e., orthoester linker) is attached to the fluorous affinity tag directly (as an R group) or indirectly through a linker L and is attached to the oligonucleotide. In some embodiments, fluorous affinity purification is used to isolate or purify an oligonucleotide-orthoester linked fluorous tag conjugate.

In some embodiments, the affinity tag is a hydrophobic tag. Non-limiting examples of hydrophobic affinity tags include molecules that comprise fluorinated groups, trityl, steroid, lipid, long alkyl saturated or unsaturated chains such as octadecyl substituents and carbocyclyl. In some embodiments, an orthoester acts as a linker between a hydrophobic affinity tag and an oligonucleotide. In other words, the orthoester (i.e., orthoester linker) is attached to the hydrophobic affinity tag directly (as an R group) or indirectly through a linker L and is also attached to the oligonucleotide. In some embodiments, hydrophobic affinity purification is used to isolate or purify an oligonucleotide-orthoester linked hydrophobic tag conjugate.

In some embodiments, the affinity tag is a biotin tag. In some embodiments, an orthoester acts as a linker between a biotin tag and an oligonucleotide. In other words, the orthoester (i.e., orthoester linker) is attached to the biotin tag directly (as an R group) or indirectly through a linker L and is also attached to the oligonucleotide. In some embodiments, avidin or streptavidin is attached to a solid phase or embedded in a gel and is used to capture the oligonucleotide-orthoester linked biotin conjugate.

In some embodiments, the affinity tag is a glutathione tag. In some embodiments, an orthoester acts as a linker between a glutathione tag and an oligonucleotide. In other words, the orthoester (i.e., orthoester linker) is attached to the glutathione tag directly (as an R group) or indirectly through a linker L and is also attached to the oligonucleotide. In some embodiments, glutathione S-tranferase (GST) is attached to a solid phase or embedded in a gel and is used to capture the oligonucleotide-orthoester linked gluthathione conjugate.

In some embodiments, the affinity tag is a maltose tag. In some embodiments, an orthoester acts as a linker between a maltose tag and an oligonucleotide. In other words, the orthoester (i.e., orthoester linker) is attached to the maltose tag directly (as an R group) or indirectly through a linker L and is also attached to the oligonucleotide. In some embodiments, maltose binding protein is attached to a solid phase or embedded in a gel and is used to capture the oligonucleotide-orthoester linked maltose conjugate.

In some embodiments, the affinity tag is an arylboronic acid tag. In some embodiments, an orthoester acts as a linker between an arylboronic acid tag and an oligonucleotide. In other words, the orthoester (i.e., orthoester linker) is attached to the arylboronic acid tag directly (as an R group) or indirectly through a linker L and is also attached to the oligonucleotide. In some embodiments, a diol containing molecule is attached to a solid phase or embedded in a gel and is used to capture the oligonucleotide-orthoester linked arylboronic acid conjugate. In some embodiments, the affinity tag is a diol-containing compound and the arylboronic acid derivative is linked to the solid support.

In some embodiments, the affinity tag is a poly-histidine peptide tag. Non-limiting examples of poly-histidine peptide tags include imidazolyl substituents such as imidazole and histidine. In some embodiments, an orthoester acts as a linker between a poly-histidine peptide tag and an oligonucleotide. In other words, the orthoester (i.e., orthoester linker) is attached to the poly-histidine peptide tag directly (as an R group) or indirectly through a linker L and is also attached to the oligonucleotide. In some embodiments, immobilized metal affinity chromatography (IMAC) purification is used to isolate or purify an oligonucleotide-orthoester linked histidine or imidazolyl conjugate.

In some embodiments, the affinity tag is a poly-sulfhydryl tag. Non-limiting examples of poly-sulfhydryl tags include substituents such as cysteine and dithiothreitol. In some embodiments, an orthoester acts as a linker between a poly-sulfhydryl tag and an oligonucleotide. In other words, the orthoester (i.e., orthoester linker) is attached to the poly-sulfhydryl tag directly (as an R group) or indirectly through a linker L and is also attached to the oligonucleotide. In some embodiments, immobilized metal affinity chromatography (IMAC) purification is used to isolate or purify an oligonucleotide-orthoester linked poly-sulfhydryl conjugate.

In some embodiments, the affinity tag is a maleimide tag. In some embodiments, an orthoester acts as a linker between a maleimide tag and an oligonucleotide. In other words, the orthoester (i.e., orthoester linker) is attached to the maleimide tag directly (as an R group) or indirectly through a linker L and is also attached to the oligonucleotide. In some embodiments, a sulfhydryl containing molecule is attached to a solid phase or embedded in a gel and is used to capture the oligonucleotide-orthoester linked maleimide conjugate. In some embodiments, the affinity tag is a sulfhydryl-containing compound and the maleimide derivative is linked to the solid support. In another embodiment, the affinity tag is a sulfhydryl-containing compound and an alpha-halocarbonyl derivative is linked to the solid support.

In some embodiments, the affinity tag is an adamantane tag. In some embodiments, an orthoester acts as a linker between an adamantane tag and an oligonucleotide. In other words, the orthoester (i.e., orthoester linker) is attached to the adamantane directly or through a linker L and to the oligonucleotide. In some embodiments, a cucurbituril or cyclodextrin is attached to a solid phase or embedded in a gel and is used to capture the oligonucleotide-orthoester linked adamantane conjugate. In other embodiment, the cyclodextrin or cucurbituril compound is attached to the orthoester linker and the adamantane is attached to a solid phase or embedded in a gel for affinity purification.

In some embodiments, the affinity tag is an azido tag. In some embodiments, an orthoester acts as a linker between an azido tag and an oligonucleotide. In other words, the orthoester (i.e., orthoester linker) is attached to the azide through a linker L and to the oligonucleotide. In some embodiments, an alkyne or cyclooctyne is attached to a solid phase or embedded in a gel and is used to capture the oligonucleotide-orthoester linked azide conjugate. In another embodiment the azido moiety is attached to the solid support or the gel and the alkyne or cyclooctyne is attached to the orthoester linker directly or indirectly.

In some embodiments, the affinity tag is cyclooctyne tag. In some embodiments, an orthoester acts as a linker between a cyclooctyne tag and an oligonucleotide. In other words, the orthoester (i.e., orthoester linker) is attached to the cyclooctyne through a linker L and to the oligonucleotide. In some embodiments, a nitrone is attached to a solid phase or embedded in a gel and is used to capture the oligonucleotide-orthoester linked cyclooctyne conjugate. In another embodiment the cyclooctyne moiety is attached to the solid support or to the gel and the nitrone-containing compound is attached to the orthoester linker directly or indirectly.

In some embodiments, the affinity tag is an alkenyl tag. In some embodiments, an orthoester acts as a linker between an alkenyl tag and an oligonucleotide. In other words, the orthoester (i.e., orthoester linker) is attached to the alkene through a linker L and to the oligonucleotide. In some embodiments, a conjugated diene is attached to a solid phase or embedded in a gel and is used to capture the oligonucleotide-orthoester linked alkene conjugate in a Diels-Alder type reaction ([4+2] cycloaddition). In another embodiment the alkene-containing compound is attached to the solid support or the gel and the conjugated diene is attached to the orthoester linker directly or indirectly.

In some embodiments, the affinity tag is an amino tag. In some embodiments, an orthoester acts as a linker between an amino tag and an oligonucleotide. In other words, the orthoester (i.e., orthoester linker) is attached to the amine through a linker L and to the oligonucleotide. In some embodiments, an activated ester such as N-hydroxysuccinimide is attached to a solid phase or embedded in a gel and is used to capture the oligonucleotide-orthoester linked amino-conjugate.

In some embodiments, the affinity tag is a hydrazide or oxyamine tag. In some embodiments, an orthoester acts as a linker between a hydrazide or oxyamine tag and an oligonucleotide. In other words, the orthoester (i.e., orthoester linker) is attached to the hydrazide or oxyamine through a linker L and to the oligonucleotide. In some embodiments, an aldehyde or ketone-containing compound is attached to a solid phase or embedded in a gel and is used to capture the oligonucleotide-orthoester linked hydrazide or oxyamine-conjugate.

In some embodiments, the oligonucleotide comprises a phosphorous protecting group, whereby a phosphorus moiety of an oligonucleotide is attached to a phosphorus protecting group. In some embodiments, the phosphorus moiety is a phosphate, phosphoramidite, or a H-phosphonate group. In some embodiments, the phosphorus protecting group is a methyl or cyanoethyl group (e.g., beta-cyanoethyl group). The methyl group may be removed using, for example, thiophenol or disodium 2-carbamoyl-2-cyanoethylene-1,1-dithiolate. The cyanoethyl group may be removed using, for example, a non-nucleophilic or hindered amine such as diethylamine, t-butylamine, or 1,8-Diazabicycloundec-7-ene (DBU). In some embodiments, the method comprises deprotecting the phosphorous protecting group of the oligonucleotide before reacting the oligonucleotide with the orthoester linker. In some embodiments, the method comprises deprotecting the nucleobase protecting group and optionally the phosphorous protecting group after reacting the oligonucleotide with the orthoester linker.

In some embodiments, the oligonucleotide comprises a nucleobase protecting group. Any nucleobase in the oligonucleotide can comprise a nucleobase protecting group. In some embodiments, the nucleobase protecting group is acetyl, isobutyryl, benzoyl, or the like. For example, the protected-nucleobase may be $N^6$-benzoyl-A, $N^6$-isobutyryl-A, $N^4$-acetyl-C, $N^4$-isobutyryl-C, or $N^2$-isobutyryl-G. In some embodiments, the nucleobase protecting group is removed by contacting the oligonucleotide to a polyamine. In some embodiments, the nucleobase protecting group is removed by contacting the oligonucleotide with a diamine such as 1,2-diaminoethane. In some embodiments, exposing the oligonucleotide to 1,2-diaminoethane for 2 hours at room temperature results in deprotection of the nucleobase. In some embodiments, the nucleobase protecting group is phenoxyacetyl, t-butylphenoxyacetyl, dimethylformamidine, dimethylacetamidine, or the like. In some embodiments, the nucleobase protecting group is removed before reacting the oligonucleotide with the orthoester linker.

In some embodiments, the nucleobase protecting group is removed after reacting the oligonucleotide with the orthoester linker.

In some embodiments, cleavage of the oligonucleotide-orthoester-linker conjugate from the solid support and deprotection of the nucleobase protecting group and optionally the phosphorus protecting group is performed simultaneously and/or in the same reaction.

In some embodiments, the oligonucleotide is an oligoribonucleotide (RNA) comprising a 2'-hydroxyl protecting group. In some embodiments, the 2'-hydroxyl protecting group is a thionocarbamate (TC) protecting group. In some embodiments, the 2'-hydroxyl protecting group is a bis(2-acetoxyethoxy)methyl (ACE) protecting group, a t-butyldimethylsilyl (TBDMS) protecting group, a triisopropylsilyloxymethyl (TOM) protecting group, a pivaloyloxymethyl (PivOM) protecting group or a 2-cyanoethoxymethyl (CEM) protecting group.

In some embodiments, the synthesis of the oligonucleotide is performed on a solid phase (e.g. CPG) that contains the 3'-terminal nucleotide attached to the solid phase with a base labile linker (such as a succinate linker or Universal Support linker (e.g. Glen Research UnySupport), or a UnyLinker). The synthesis cycle includes deprotection of the 5'-OH protecting group (e.g. trityl or DMT), coupling of a phosphoramidite in the presence of an activator, capping of the unreacted hydroxyl groups with a base labile protecting group (e.g. acetyl protecting group), and oxidation of the phoshitetriester linkage to the phosphatetriester linkage.

Nascently synthesized oligonucleotides, DNA, RNA or modified oligonucleotides are synthesized on solid support. The resulting full-length product is prepared for attaching an orthoester linker which comprises an affinity tag by removing the final protective group in a de-blocking step. That protective group can be various groups well known in the literature; most typically DMT, Pixyl, or BZH. The synthesis of oligonucleotides can occur in the 3' to 5' direction where the final protective group is removed from the 5'-hydroxyl of the resulting oligonucleotide, or the synthesis can occur in the 5' to 3' direction in which the final protective group is removed from the 3'-hydroxyl of the resulting oligonucleotide. At this point the phosphorus protective group can be optionally removed from the nascently synthesized oligonucleotide. An orthoester linker comprising an affinity tag is reacted with the hydroxyl group of the full-length product and only the full-length product as the hydroxyls of truncated sequences were capped with for example an acetate protecting groups during synthesis and thus are unable to react with the orthoester linker. The hydroxyl group was liberated in the final deblocking step which may be performed using mild acid as a trans-orthoesterification catalyst. The conjugation of the orthoester linker with the full length oligonucleotide is typically performed in a high dielectric constant solvent (e.g., acetonitrile, DMF, dioxane, THF, propylene carbonate and the like), at room temperature or at higher temperature, up to 95° C., and an acid solution (acid in anhydrous solvent, for example acetonitrile) is added to the reaction at a concentration from about 0.001M to about 0.1 M, preferably at about 0.02M (e.g. perfluoroheptanoic acid or heptafluorobutyric acid, trichloroacetic acid, dichloroacetic acid, 2-dichloropropionic, 2 3-dichloropropionic, 2,6-Bis(trifluoromethyl)benzoic acid, 2-(Trifluoromethyl)benzoic acid, 4,4,5,5,6,6,7,7,8,8,9,9,9-Tridecafluorononanoic acid and 4,4,5,5,6,6,6-heptafluorohexanoic acid) and the reaction is carried out for about 15 minutes to about 12 hours, depending on the reactivity of the orthoester linker.

The resulting orthoester linker-oligonucleotide conjugate and the untagged truncated oligonucleotides can now be treated with various basic amines (ammonia, ammonium hydroxide, methylamine, ethylenediamine and the like) to optionally remove various protective groups, nucleobase protecting groups and if present, base labile 2'-hydroxyl protecting groups such as TC, or PivOM, and possibly cleave the linker, typically a succinate linker or a unylinker that attaches the oligonucleotides to the solid support.

The full-length oligonucleotide-orthoester linker conjugate and the untagged truncated sequences (crude sample) are eluted from the solid support in a buffer, typically a buffer containing 0.2 M sodium phosphate, 0.6 M sodium chloride, pH 7.4, and 10% dimethylformamide (loading buffer).

The liberated crude oligonucleotides can then be purified using a chromatographic separation or a solid-phase extraction (e.g. a cartridge) aided by the affinity pair. The crude oligonucleotide sample containing the full-length oligonucleotide-orthoester linker conjugate attached to the affinity tag and the untagged truncated sequences, is loaded, with the loading buffer, on to a column or a cartridge filled with a resin or beads or a polymeric material containing the capture moiety. The affinity tag attached to the full-length oligonucleotide-orthoester linker conjugate binds—by affinity or covalently—to the capture moiety imbedded in the resin or the beads and is retained on the resin or the beads while the untagged truncated sequences are eluted out of the column or the cartridge with a washing buffer, usually a 0.01M sodium phosphate buffer (pH=7.4)

The orthoester linker can then be cleaved from the full-length oligonucleotide conjugate by adding to the column or the cartridge a mild acid solution (cleavage buffer), for example a 3.0 M sodium acetate buffer (pH5.5) and letting it sit for 30 mins to 3 hours at room temperature. If monomers with non-base labile 2'-hydroxyls protecting groups were used to synthesize the oligonucleotide, such as ACE, CEM, TBDMS or TOM or others—the deprotection of those non base-labile 2'-hydroxyls protecting groups (e.g. TBDMS, TOM or CEM) can be performed with fluoride ions before (if the affinity capture material is resistant to the chemical deprotection treatment) or after the cleavage of the orthoester linker from the full length oligonucleotide. Alternatively, if acid labile 2'-hydroxyl protective groups are used, such as ACE, the deprotection of these groups can be carried out during the cleavage of the orthoester linker from the full-length oligonucleotide. After cleavage of the orthoester linker, the cleavage buffer is then removed from the column using the wash buffer until the pH of the eluent is back to about 7. The adsorbed purified full-length oligonucleotide is eluted from the resin or the beads, using a 10% acetonitrile in DNase/RNase-Free water.

In some embodiments, the orthoester linker conjugation is performed on the synthesis column in presence of an acid. Following the orthoester-oligonucleotide conjugation, cleavage of the oligonucleotide-orthoester conjugate from the synthesis solid phase (e.g. CPG) is performed, as well as the deprotection of the oligonucleotide various protecting groups (phosphorous, nucleobases and 2'O-hydroxyl protecting groups when RNA is synthesized).

Depending on the chemistry used to synthesize the oligonucleotide (i.e. monomers composition), the deprotection of the protecting groups is performed with a base or basic reagent (e.g. 1,2-diaminoethane, ammonia, ammonium hydroxide and the like) at room temperature or at higher temperature. In some embodiments, synthesis of the oligonucleotide is accomplished on a solid phase that contains the 3'-terminal nucleotide attached by a non-base labile cleavable linker (e.g. photocleavable linker). In this embodiment, capping of unreacted 5'-hydroxyl groups on the growing oligonucleotide is accomplished with a non-base labile reagent (e.g. Unicap), which upon deprotection leaves a phosphate group rather than a free hydroxyl group on the truncated oligonucleotide sequences. In such an embodiment, deprotection of phosphorus and nucleotide protecting groups with an amine base yields a deprotected oligonucleotide still attached to a solid phase, but with only the 5'-terminal hydroxyl group available for conjugation with the orthoester linker. Following conjugation between the orthoester linker and the oligonucleotide, which is still attached to the solid-phase, but nucleotide and phosphorus deprotected, the oligonucleotide can be cleaved from the solid phase and subjected to affinity purification to isolate the desired full length orthoester-oligonucleotide conjugate. Finally, the orthoester linker is cleaved from the purified full-length oligonucleotide in a mild acidic solution (pH=5-6) and eluted from the affinity separation medium.

The 2'-hydroxyl protecting group can be removed using any suitable conditions. In some embodiments, a TC or PivOM protecting group is removed from the 2'-hydroxyl by contacting the oligoribonucleotide with a diamine such as 1,2-diaminoethane. In some embodiments, a PivOM protecting group is removed from the oligoribonucleotide by contacting the oligoribonucleotide with ammonia or an alkyl amine. In some embodiments, contacting the oligoribonucleotide with a diamine, ammonia, or an alkyl amine results in simultaneous deprotection of the 2'-hydroxyl group and cleavage of the oligoribonucleotide from the solid support. In some embodiments, an ACE protecting group is removed by contacting the oligoribonucleotide with an acid. In some embodiments, the ACE protecting group and orthoester linker are removed simultaneously. In some embodiments, the 2'-hydroxyl protecting groups are TBDMS or TOM protecting groups and are removed by contacting the oligoribonucleotide with a composition comprising fluoride. The TBDMS or TOM protecting groups may be removed after isolating the oligoribonucleotide-orthoester linker conjugate and before, simultaneously, or after cleaving the orthoester linker.

In some embodiments, the 2'-hydroxyl protecting group is removed prior to isolating the oligoribonucleotide-orthoester linker conjugate. In some embodiments, the 2'-hydroxyl protecting group is removed after isolating the oligoribonucleotide-orthoester linker conjugate. In some embodiments, the oligonucleotide is treated with 1,2-diaminoethane, resulting in simultaneous removal of the protecting groups from the oligonucleotide and cleavage of the oligoribonucleotide-orthoester linker conjugate from the solid support.

In some embodiments, the oligonucleotide comprises a phosphorus protecting group or a nucleobase protecting group. In some embodiments, the oligonucleotide comprises a phosphorus protecting group and a nucleobase protecting group. In some embodiments, the oligonucleotide is an RNA that comprises a phosphorus protecting group, a nucleobase protecting group, and a 2'-hydroxyl protecting group.

In some embodiments, the oligonucleotide is treated with 1,2-diaminoethane, thereby removing the 2'-OH protecting group (e.g., TC or PivOM) from the oligonucleotide and cleaving the oligoribonucleotide-orthoester linker conjugate from the synthesis solid support simultaneously.

In some embodiments, two of R', R'', and R''' groups of the orthoester linker (Ia) are linked together through a carbon-carbon bond and form a 5, 6, or 7-member 7-member ring cyclic orthoester as shown in compound of formula (I).

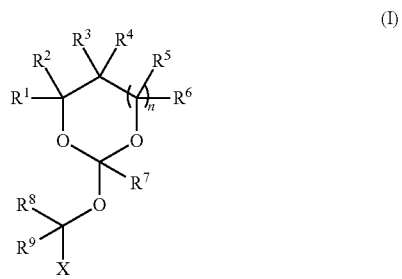
(I)

wherein each of $R^1$, $R^2$, $R^3$, $R^4$, $R^5$, $R^6$, $R^7$, $R^8$ and $R^9$ is independently H, $C_1$-$C_{24}$ alkyl, $C_1$-$C_{24}$ heteroalkyl, $C_2$-$C_{24}$ alkenyl, $C_2$-$C_{24}$ heteroalkenyl $C_2$-$C_{24}$ alkynyl, $C_2$-$C_{24}$ heteroalkynyl, halogen, aryl, carbocyclyl, heteroaryl, heterocyclyl, substituted $C_1$-$C_{24}$ alkyl, substituted $C_2$-$C_{24}$ alkenyl, substituted $C_2$-$C_{24}$ alkynyl, or substituted aryl and at least one of $R^1$, $R^2$, $R^3$, $R^4$, $R^5$, and $R^6$ is not H; X is H, methyl or an electron withdrawing group; and n is 0, 1, or 2, wherein at least one of $R^1$, $R^2$, $R^3$, $R^4$, $R^5$, $R^6$ or $R^7$ comprises an affinity tag; preferably, $R^7$, $R^8$ and $R^9$ are H.

When n is 2, the orthoester linker moiety forms a 7-member ring cyclic orthoester as shown in the following structure, and has two additional R groups $R'_5$ and $R'_6$ on the additional carbon which are defined each independently, as any of $R^1$ to $R^6$ groups:

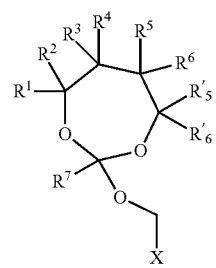

In some embodiments, in the orthoester linker of the formula (I), each of $R^1$, $R^2$, $R^3$, $R^4$, $R^5$, $R^6$ and $R^7$ is independently H, $C_1$-$C_{24}$ alkyl, $C_1$-$C_{24}$ heteroalkyl, $C_2$-$C_{24}$ alkenyl, $C_2$-$C_{24}$ heteroalkenyl, $C_2$-$C_{24}$ alkynyl, $C_2$-$C_{24}$ heteroalkynyl, halogen, aryl, heteroaryl, heterocyclyl, carbocyclyl, or any substituted equivalents or combination thereof provided that the total number of carbons doesn't exceed 24; $R^8$ and $R^9$ are H; X is H, methyl or an electron withdrawing group; and n is 0, 1, or 2, wherein at least one of $R^1$, $R^2$, $R^3$, $R^4$, $R^5$, $R^6$ or $R^7$ comprises an affinity tag.

In some embodiments, in the orthoester linker of the formula (I), at least one of $R^1$, $R^2$, $R^3$, $R^4$, $R^5$, $R^6$ or $R^7$ is a fluorosubstituted alkyl, a fluorosubstituted alkenyl, a fluorosubstituted alkynyl, a fluorosubstituted carbocyclyl, a fluorosubstituted heteroalkyl, a fluorosubstituted heteroalkenyl, a fluorosubstituted heteroalkynyl, or a fluorosubstituted heterocyclyl.

In some embodiments, the orthoester linker is the following compound of formula (Id):

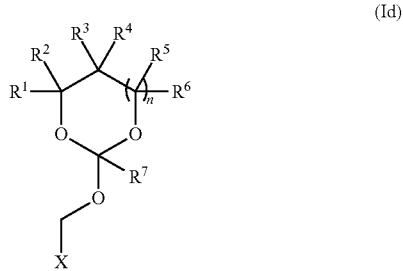
(Id)

wherein at least one of $R^1$, $R^2$, $R^3$, $R^4$, $R^5$, $R^6$ and $R^7$ is $C_1$-$C_{24}$ alkyl, $C_1$-$C_{24}$ heteroalkyl, $C_2$-$C_{24}$ alkenyl, $C_2$-$C_{24}$ heteroalkenyl, $C_2$-$C_{24}$ alkynyl, $C_2$-$C_{24}$ heteroalkynyl, halogen, aryl, heteroaryl, heterocyclyl, carbocyclyl, any substituted equivalent or any combination thereof provided that the total number of carbons doesn't exceed 24 and the remaining $R^1$, $R^2$, $R^3$, $R^4$, $R^5$, $R^6$ and $R^7$ are H, $C_1$-$C_6$ alkyl, $C_2$-$C_6$ alkenyl, $C_2$-$C_6$ alkynyl, halo- or hetero-substituted equivalents, $C_3$-$C_{12}$ carbocyclyl or heterocyclyl and substituted equivalents with the proviso that two R groups of $R^1$ to $R^7$ groups do not form a fused ring with the cyclic orthoester as shown below:

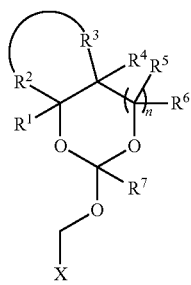

wherein X is F, Cl, Br, or a mono-, bis or tris-halosubstituted methyl; and n is 0 or 1, wherein at least one of $R^1$, $R^2$, $R^3$, $R^4$, $R^5$, $R^6$ or $R^7$ comprises an affinity tag.

The orthoester linker of the formula (Id) includes compounds in which n is 0 and at least two of $R^1$, $R^2$, $R^3$, $R^4$, $R^5$, and $R^6$ are each independently $C_1$-$C_{24}$ alkyl, $C_1$-$C_{24}$ heteroalkyl, $C_2$-$C_{24}$ alkenyl, $C_2$-$C_{24}$ heteroalkenyl, $C_2$-$C_{24}$ alkynyl, $C_2$-$C_{24}$ heteroalkynyl, halogen, aryl, heteroaryl, heterocyclyl, carbocyclyl or any substituted equivalent, and all the remaining R groups of $R^1$, $R^2$, $R^3$, $R^4$, $R^5$, and $R^6$ are H, provided that the two R groups that are not H are not linked together to form a fused ring with the cyclic orthoester.

The orthoester linker of the formula (Id) includes compounds in which one of $R^1$, $R^2$, $R^3$, $R^4$, $R^5$ or $R^6$ is a fluorosubstituted alkyl, a fluorosubstituted alkenyl, a fluorosubstituted alkynyl, or a fluorosubstituted aryl.

In the orthoester linker of formula (Id), the affinity tag may be a fluorous tag or a hydrophobic tag with a cLog P value of at least 3.

The affinity tag (AfTg) may be a part or the totality of the chemical structure of an R group ($R^1$, $R^2$, $R^3$, $R^4$, $R^5$, $R^6$, $R^7$) or it may be attached to the orthoester through a linker L as shown below.

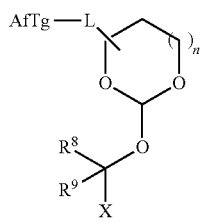

Wherein AfTg is an affinity tag, and L is a covalent bond or is a straight, branched, mono- or poly-cyclic, saturated, partially unsaturated or unsaturated $C_1$-$C_{12}$ hydrocarbon chain that is optionally substituted with F, Cl, Br, I or $C_1$-$C_3$ alkyls and optionally interspersed with heteroatoms independently selected from: O, S, N, or with groups independently selected from $NR^a$—$R^b$, —$NR^a$—CO—$R^b$, —CO—$NR^a$—$R^b$, —CO—$R^a$ wherein $R^a$, $R^b$ are each independently H or $C_1$-$C_6$ alkyl.

In some embodiments, the orthoester linker is a compound of formula (I) wherein $R^5$ and $R^6$ are H. In some embodiments, the orthoester linker is a compound of formula (I) wherein $R^5$, $R^6$, $R^7$, $R^8$ and $R^9$ are H. Preferably, n is 0.

In some embodiments, the orthoester linker is a compound of formula (I) wherein one of $R^1$, $R^2$, $R^3$, $R^4$, $R^5$, and $R^6$ is $C_1$-$C_{24}$ alkyl, $C_1$-$C_{24}$ heteroalkyl, $C_2$-$C_{24}$ alkenyl, $C_2$-$C_{24}$ heteroalkenyl, $C_2$-$C_{24}$ alkynyl, $C_2$-$C_{24}$ heteroalkynyl, halogen, aryl, heteroaryl, heterocyclyl, substituted $C_1$-$C_{24}$ alkyl, substituted $C_2$-$C_{24}$ alkenyl, substituted $C_2$-$C_{24}$ alkynyl, or substituted aryl and all the others of $R^1$, $R^2$, $R^3$, $R^4$, $R^5$, and $R^6$ are H; $R^7$, $R^8$, and $R^9$ are H; X is H or an electron withdrawing group; and n is 0, 1, or 2, and at least one of $R^1$, $R^2$, $R^3$, $R^4$, $R^5$ or $R^6$ comprises an affinity tag.

In some embodiments, $R^1$ comprises an affinity tag. In some embodiments, $R^2$ comprises an affinity tag. In some embodiments, $R^3$ comprises an affinity tag. In some embodiments, $R^4$ comprises an affinity tag. In some embodiments, $R^5$ comprises an affinity tag. In some embodiments, $R^6$ comprises an affinity tag. In some embodiments, $R^7$ comprises an affinity tag. In some embodiments, at least two of $R^1$, $R^2$, $R^3$, $R^4$, $R^5$, $R^6$ or $R^7$ comprises an affinity tag. In some embodiments, at least three of $R^1$, $R^2$, $R^3$, $R^4$, $R^5$, $R^6$ or $R^7$ comprises an affinity tag. In some embodiments, at least four of $R^1$, $R^2$, $R^3$, $R^4$, $R^5$, $R^6$ or $R^7$ comprises an affinity tag. In some embodiments, at least five of $R^1$, $R^2$, $R^3$, $R^4$, $R^5$, $R^6$ or $R^7$ comprises an affinity tag. In some embodiments, each of $R^1$, $R^2$, $R^3$, $R^4$, $R^5$, or $R^6$ comprises an affinity tag.

In some embodiments, the orthoester linker is a compound of formula (I) wherein at least one of $R^1$, $R^2$, $R^3$, $R^4$, $R^5$, $R^6$ or $R^7$ is a fluorosubstituted alkyl, a fluorosubstituted alkenyl, a fluorosubstituted alkynyl, a fluoroheteroalkyl or a fluorosubstituted aryl. In some embodiments, the orthoester linker is a compound of formula (I) wherein at least one of $R^1$, $R^2$, $R^3$, $R^4$, $R^5$, or $R^6$ is a fluorosubstituted alkyl, a fluorosubstituted alkenyl, a fluorosubstituted alkynyl, or a fluorosubstituted aryl.

In some embodiments, the orthoester linker is a compound of formula (I) wherein $R^1$, $R^2$, $R^3$, $R^4$, $R^5$ or $R^6$ is a $C_1$-$C_{24}$ alkyl comprising one or more heteroatom. In some embodiments, the heteroatom is oxygen. In some embodiments, the heteroatom is nitrogen. In some embodiments, the heteroatoms are a combination of different heteroatoms.

In some embodiments, the orthoester linker is a compound of formula (I) wherein $R^7$ is H.

In some embodiments, the orthoester linker is a compound of formula (I) wherein $R^1$, $R^2$, and $R^3$ are H and $R^4$ is a $C_1$-$C_{24}$ alkyl.

In some embodiments, the orthoester linker is a compound of formula (I) wherein $R^1$, $R^2$, $R^3$, $R^5$, $R^6$ and $R^7$ are hydrogen, and $R^4$ is $C_1$-$C_{24}$ alkyl, $C_1$-$C_{24}$ heteroalkyl or $C_6$-$C_{24}$ arylalkyl and substituted equivalents.

In some embodiments, the orthoester linker is a compound of formula (I) wherein $R^8$ and $R^9$ are hydrogen.

In some embodiments, the orthoester linker is a compound of formula (I) wherein one of $R^8$ or $R^9$ is methyl.

In some embodiments, the orthoester linker is a compound of formula (I) wherein one of $R^8$ or $R^9$ is a halogen.

In some embodiments, the orthoester linker is a compound of formula (I) wherein X is hydrogen.

In some embodiments, the orthoester linker is a compound of formula (I) wherein X is a halosubstituted alkyl. In some embodiments, the halosubstituted alkyl is $CF_3$, $CF_2H$, $CFH_2$, $CCl_3$, $CCl_2H$, or $CClH_2$. In some embodiments, the orthoester linker is a compound of formula (I) wherein X is $CF_3$.

In some embodiments, the orthoester linker is a compound of formula (I) wherein X is Cl, F, $SO_3H$, $NO_2$, $SO_2R^{10}$, $CH_2SO_2R^{10}$, $COR^{10}$, $CH_2COR^{10}$, $NO_2$, $CH_2CN$, or carbonyl, wherein $R^{10}$ is $C_1$-$C_6$ alkyl, $C_2$-$C_6$ alkenyl, $C_2$-$C_6$ alkynyl, substituted $C_1$-$C_6$ alkyl, aryl, heteroaryl, or heterocyclyl.

In some embodiments, the orthoester linker is a compound of formula (I) wherein n is 0.

In some embodiments, the orthoester linker is a compound of formula (I) wherein $R^1$, $R^2$, $R^3$, $R^4$, $R^5$ or $R^6$ is substituent

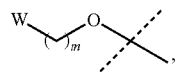

wherein W is a fluorosubstituted alkyl group and m is 1 to 12. In some embodiments, the fluorosubstituted alkyl comprises 1 to 25 fluorine atoms.

In some embodiments, the orthoester linker is a compound of formula (I) that comprises at $R^1$, $R^2$, $R^3$, or $R^4$ substituent

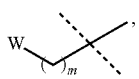

wherein W is a halosubstituted alkyl group and m is 1 to 12. In some embodiments, the substituent comprises 1-14 additional fluorine atoms.

In some embodiments, the orthoester linker is a compound of formula (I) that comprises at $R^1$, $R^2$, $R^3$, $R^4$, $R^5$ or $R^6$ a substituent

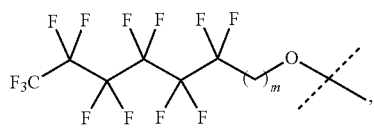

wherein m is 0 to 6. In some embodiments, $R^5$ and $R^6$ are hydrogen.

In some embodiments, the orthoester linker is a compound of formula (I) that comprises at $R^1$, $R^2$, $R^3$, $R^4$, $R^5$ or $R^6$ a substituent

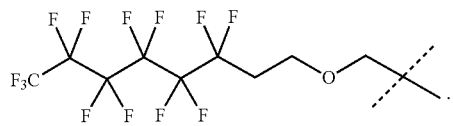

In some embodiments, $R^5$ and $R^6$ are hydrogen.

In some embodiments, the orthoester linker is a compound of formula (I) that comprises at $R^1$, $R^2$, $R^3$, $R^4$, $R^5$ or $R^6$ substituent

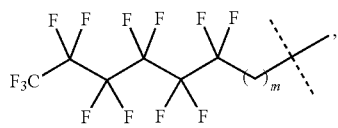

wherein m is 0 to 6. In some embodiments, $R^5$ and $R^6$ are hydrogen.

In some embodiments, the orthoester linker is a compound of formula (I) wherein $R^1$, $R^2$, $R^3$ or $R^4$, $R^5$ and $R^6$ are H and $R^3$ or $R^4$ is a $C_1$-$C_{24}$ fluoroalkyl optionally comprising one or more heteroatom; X is $CF_3$; and n is 0 or 1.

In some embodiments, the orthoester linker is a compound of formula (I) wherein $R^1$, $R^2$, $R^3$ or $R^4$, $R^5$ and $R^6$ are H and $R^3$ or $R^4$ is a $C_1$-$C_{24}$ alkyl optionally comprising one or more heteroatom; X is $CF_3$; and n is 0 or 1.

In some embodiments, the orthoester linker is

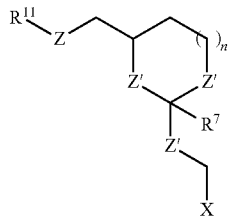

wherein $R^{11}$ is H, $C_1$-$C_{24}$ alkyl, $C_1$-$C_{24}$ heteroalkyl, $C_1$-$C_{24}$ substituted alkyl, $C_2$-$C_{24}$ alkenyl, $C_2$-$C_{24}$ heteroalkenyl, $C_2$-$C_{24}$ substituted alkenyl, $C_2$-$C_{24}$ alkynyl, $C_2$-$C_{24}$ heteroalkynyl, $C_2$-$C_{24}$ substituted alkynyl, aryl, substituted aryl, heteroaryl, substituted heteroaryl, heterocyclyl or substituted heterocyclyl; $R^7$ is H or $CH_3$. Z is $CR^aR^b$, O, S or $NR^a$ wherein $R^a$ and $R^b$ are each independently H or $C_1$-$C_6$ alkyl; Z' are each independently selected from O and S; X is H, $CH_3$ or an electron withdrawing group; and n is 0, 1, or 2. In some embodiments, $R^{11}$ comprises an affinity tag. In some embodiments, $R^{11}$ is an affinity tag. Preferably n is 0.

In some embodiment, the orthoester linker is:

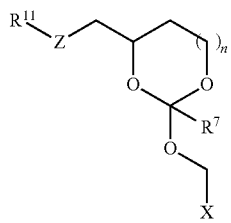

wherein $R^{11}$ is H, $C_1$-$C_{24}$ alkyl, $C_1$-$C_{24}$ heteroalkyl, $C_1$-$C_{24}$ substituted alkyl, $C_2$-$C_{24}$ alkenyl, $C_2$-$C_{24}$ heteroalkenyl, $C_2$-$C_{24}$ substituted alkenyl, $C_2$-$C_{24}$ alkynyl, $C_2$-$C_{24}$ heteroalkynyl, $C_2$-$C_{24}$ substituted alkynyl, aryl, substituted aryl, heteroaryl, substituted heteroaryl, heterocyclyl or substituted heterocyclyl; $R^7$ is H or $CH_3$. Z is $CR^aR^b$, O, S or $NR^a$ wherein $R^a$ and $R^b$ are each independently H or $C_1$-$C_6$ alkyl. X is H, $CH_3$ or an electron withdrawing group; and n is 0, 1, or 2. In some embodiments, $R^{11}$ comprises an affinity tag. Preferably n is 0.

In some embodiment, the orthoester linker is:

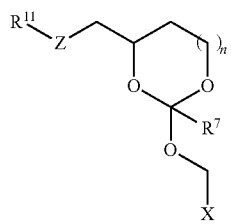

wherein $R^{11}$ is H, $C_1$-$C_{23}$ alkyl, $C_1$-$C_{23}$ heteroalkyl, $C_1$-$C_{23}$ substituted alkyl, $C_2$-$C_{23}$ alkenyl, $C_2$-$C_{23}$ heteroalkenyl, $C_2$-$C_{23}$ substituted alkenyl, $C_2$-$C_{23}$ alkynyl, $C_2$-$C_{23}$ heteroalkynyl, $C_2$-$C_{23}$ substituted alkynyl, aryl, substituted aryl, heteroaryl, substituted heteroaryl, heterocyclyl or substituted heterocyclyl; $R^7$ is H or $CH_3$. Z is $CR^aR^b$, O, S, $NR^a$, $NR^aCO$, $CONR^a$, wherein $R^a$ and $R^b$ are each independently H, $C_1$-$C_6$ alkyl, or $R^a$ and $R^{11}$ together form a heterocycle with N; X is F, Cl, Br, or a mono-, bis or tris-halosubstituted methyl; and n is 0 or 1, $R^{11}$ comprises an affinity tag.

In some embodiments, the orthoester linker is:

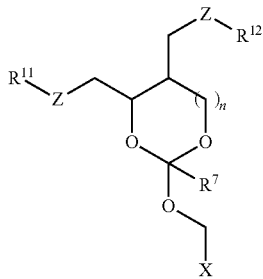

wherein $R^{11}$ and $R^{12}$ are each independently H, $C_1$-$C_{23}$ alkyl, $C_1$-$C_{23}$ heteroalkyl, $C_1$-$C_{23}$ substituted alkyl, $C_2$-$C_{23}$ alkenyl, $C_2$-$C_{23}$ heteroalkenyl, $C_2$-$C_{23}$ substituted alkenyl, $C_2$-$C_{23}$ alkynyl, $C_2$-$C_{23}$ heteroalkynyl, $C_2$-$C_{23}$ substituted alkynyl, aryl, substituted aryl, heteroaryl, substituted heteroaryl, heterocyclyl or substituted heterocyclyl provided that at least one of $R^{11}$ and $R^{12}$ comprises an affinity tag; $R^7$ is H or $CH_3$. Z are each independently $CR^aR^b$, O, S, $NR^aCO$, $CONR^a$ or $NR^a$ wherein $R^a$ and $R^b$ are each independently H, $C_1$-$C_6$ alkyl, or $R^a$ and $R^{11}$ or $R^a$ and $R^{12}$ together form a heterocycle with N; X is F, Cl, Br, or a mono-, bis or tris-halosubstituted methyl; and n is 0 or 1.

In some embodiments, the orthoester linker is:

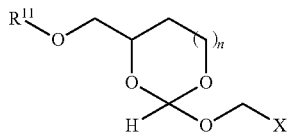

wherein $R^{11}$ is H, $C_1$-$C_{24}$ alkyl, $C_1$-$C_{24}$ heteroalkyl, $C_1$-$C_{24}$ substituted alkyl, $C_2$-$C_{24}$ alkenyl, $C_2$-$C_{24}$ heteroalkenyl, $C_2$-$C_{24}$ substituted alkenyl, $C_2$-$C_{24}$ alkynyl, $C_2$-$C_{24}$ heteroalkynyl, $C_2$-$C_{24}$ substituted alkynyl, aryl, substituted aryl, heteroaryl, substituted heteroaryl, heterocyclyl or substituted heterocyclyl; X is an electron withdrawing group; and n is 0, 1, or 2. In some embodiments, $R^{11}$ comprises an affinity tag. In some embodiments, $R^{11}$ is a $C_1$-$C_{12}$ alkyl optionally substituted with at least 4 fluorine atoms. In some embodiments, X is $CF_3$, $CF_2H$, $CFH_2$, Br, Cl, F, $SO_3H$, $NO_2$, CN or carbonyl. In some embodiments, X is Br, Cl, F, or a mono-, bis or tris-halosubstituted methyl.

In some embodiments, the orthoester linker is:

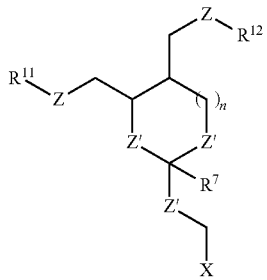

-continued

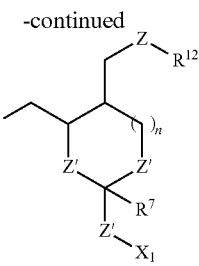

wherein $R^{11}$ and $R^{12}$ are each independently H, $C_1$-$C_{24}$ alkyl, $C_1$-$C_{24}$ heteroalkyl, $C_1$-$C_{24}$ substituted alkyl, $C_2$-$C_{24}$ alkenyl, $C_2$-$C_{24}$ heteroalkenyl, $C_2$-$C_{24}$ substituted alkenyl, $C_2$-$C_{24}$ alkynyl, $C_2$-$C_{24}$ heteroalkynyl, $C_2$-$C_{24}$ substituted alkynyl, aryl, substituted aryl, heteroaryl, substituted heteroaryl, heterocyclyl or substituted heterocyclyl; $R^7$ is H or $CH_3$. Z are each independently $CR^aR^b$, O, S or $NR^a$ wherein $R^a$ and $R^b$ are each independently H or $C_1$-$C_6$ alkyl provided that $R^{11}$ and $R^{12}$ do not form together a cycle; Z' are each independently selected from O and S; X is X is Br, Cl, F, a mono-, bis or tris-halosubstituted methyl; $X_1$ is a vinyl, an acetylene, a phenyl or any substituted equivalents; and n is 0, 1, or 2. In some embodiments, X is $CF_3$, $CF_2H$, $CFH_2$, Br, Cl, F, $SO_3H$, $NO_2$, CN or carbonyl. In some embodiments, $R^{11}$ and $R^{11}$ comprise or are an affinity tag. Preferably n is 0.

Suitable orthoester linkers include the orthoester linker having one of the following structures:

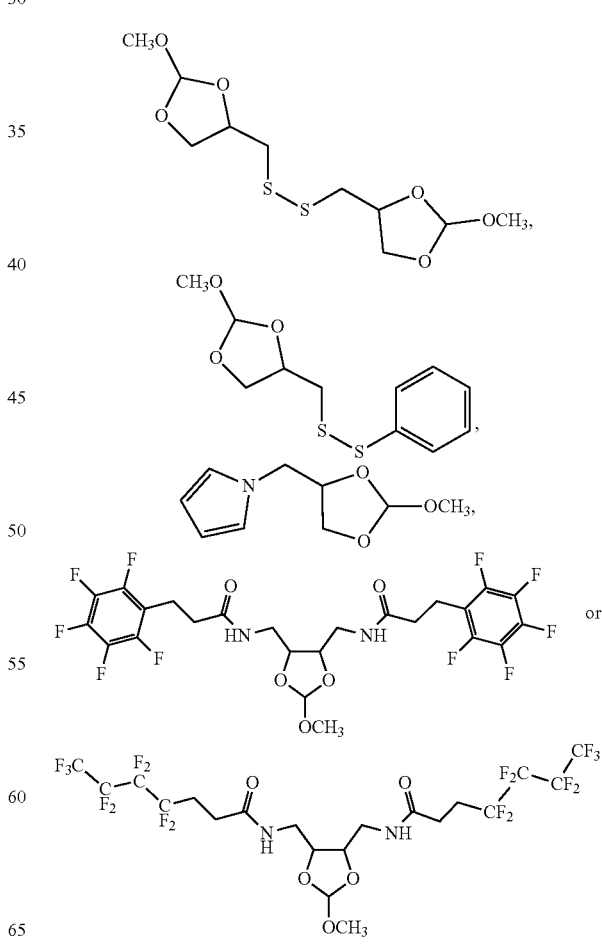

In some embodiments, the orthoester linker is a fluorous orthoester linker having the following structure:

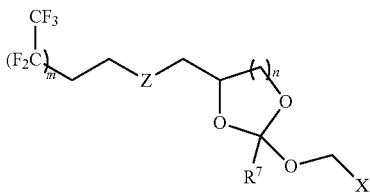

wherein Z is $CH_2$, O, S, $NR^a$, or $NR^aCO$ wherein $R^a$ is H or $C_1$-$C_6$ alkyl; $R^7$ is H, methyl, ethyl, n-propyl, phenyl or benzyl; X is H, F, Cl, Br, or a mono-, bis- or tris-halosubstituted methyl or cyano-; m is an integer from 0 to 12; n is 1 or 2.

In some embodiments, the orthoester linker is

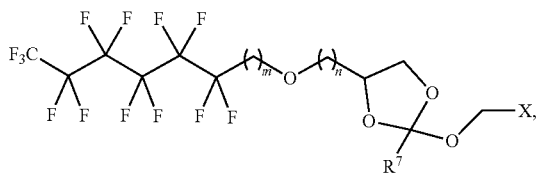

wherein $R^7$ is H, $C_1$-$C_{24}$ alkyl, $C_2$-$C_{24}$ alkenyl, $C_2$-$C_{24}$ alkynyl, halosubstituted alkyl, aryl, heteroaryl, or heterocycle; X is an electron withdrawing group; and each of m and n are independently 1, 2, 3, or 4.

In another embodiment, the present invention provides an orthoester linker of formula (II)

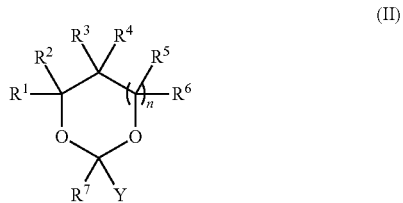

(II)

wherein each of $R^1$, $R^2$, $R^3$, $R^4$, $R^5$, $R^6$ and $R^7$ is independently H, $C_1$-$C_{24}$ alkyl, $C_1$-$C_{24}$ heteroalkyl, $C_2$-$C_{24}$ alkenyl, $C_2$-$C_{24}$ heteroalkenyl $C_2$-$C_{24}$ alkynyl, $C_2$-$C_{24}$ heteroalkynyl, halogen, aryl, heteroaryl, heterocyclyl, substituted $C_1$-$C_{24}$ alkyl, substituted $C_2$-$C_{24}$ alkenyl, substituted $C_2$-$C_{24}$ alkynyl, substituted aryl, substituted heteroaryl or substituted heterocyclyl; Y is a leaving group; and n is 0, 1, or 2, wherein at least one of $R^1$, $R^2$, $R^3$, $R^4$, $R^5$, $R^6$ or $R^7$ comprises an affinity tag. Preferably, $R^7$ is H.

In some embodiments, at least one of $R^1$, $R^2$, $R^3$, $R^4$, $R^5$, $R^6$ or $R^7$ is $CF_3$—$(CF_2)_q$—$(CR^{12}R^{13})_p$—Z—$(CR^{14}R^{15})_m$, wherein Z is, O, S, $SO_2$, NH, NHCO, CONH, or $CR^{16}R^{17}$; each of $(CR^{12}R^{13})$, $(CR^{14}R^{15})$ and $(CR^{16}R^{17})$ is independently $C_1$-$C_3$ alkylene, halosubstituted $C_1$-$C_3$ alkylene, $C_2$-$C_3$ alkenylene, halosubstituted $C_2$-$C_3$ alkenylene, $C_2$-$C_3$ alkynylene, halosubstituted $C_2$-$C_3$ alkynylene, $CH_2$—$CH_2$—O—, or $CH_2$—$CH_2$—NH—; m is 1 or 2; p is 0, 1 or 2; and q is an integer from 0 to 7.

In some embodiments, the leaving group Y is O—Y' and is derived from an alcohol of formula HO—Y'. In some embodiments, Y' is a $C_1$-$C_8$ alkyl. In some embodiments, Y' is a substituted $C_1$-$C_8$ alkyl, preferably a halosubstituted alcohol. In some embodiments, Y' is a vinyl, an acetylene, a phenyl or any substituted equivalents, where the substituent(s) is an electron withdrawing group EWG. In some embodiments, Y' is a methyl, an ethyl, or any substituted equivalents where the substituent is halo, cyano, or nitro. In some embodiments, the alcohol of formula HO—Y' has a pKa from about 8 to about 15, preferably from about 9 to 13.

In some embodiments, the alcohol of formula HO—Y' is methanol, ethanol, 2,2,2-trifluoroethanol, 2,2,2-trichloroethanol, 2,2-difluoroethanol, 2,2-dichloroethanol 2-methoxyethanol, hydroxyacetaldehyde, 2-propen-1-ol, 2-silylethanol, 1-hydroxy-2-propyne, 2-chloroethanol, 2-fluoroethanol, 3-butenyl alcohol, 3-butyn-1-ol, 2-butyn-1-ol, 2,3-butadien-1-ol, 1-chloro-2-propanol, 1-fluoro-2-propanol, 2-cyanoethanol, 2-(methylthio)ethan-1-ol, 2-buten-1-ol, 2-chloro-1-propanol, 2-ethoxyethanol, 2-chloro-1-propanol, 1-hydroxy-2-propanone, 2,2-difluoro-ethanol, 3-fluoro-1-propanol, 2-methyl-3-butyn-1-ol, 2,2-dichloroethanol, 4-penten-2-ol, 3-chloro-1-propanol, 4-pentyn-2-ol, 2-fluoro-1-propanol, 2-methylene-1-butanol, 2-methyl-3-buten-1-ol, 1-chloro-1-propanol, 1-cyclopropene-1-methanol, 2-fluoro-1-propanol, 2-cyclopropene-1-methanol, 3-methyl-3-buten-1-ol, 1,4-pentadien-3-ol, 1-penten-4-yn-3-ol, 3,4-pentadien-2-ol, 2-methyl-2,3-butadien-1-ol, 3-pentyn-2-ol, 2-methyl-2-buten-1-ol, 4-methyl-1-penten-3-ol, 4-pentyn-1-ol, 3,4-pentadien-1-ol, 2-pentyn-1-ol, 3-methyl-2-methylene-1-butanol, 3-hydroxy-2-methyl-propanal, 3-methyl-2-buten-2-ol, 3-hydroxy-butanal, 2-cyclopropen-1-ol, 3-hydroxy-butanal, 1-methoxy-2-propanol, 2-(1-methylethoxy)-ethanol, 4-methoxy-1-butanol, 2-(2-methoxyethoxy)-ethanol, α-methyl-cyclopropanemethanol, 3-methyl-4-penten-2-ol, 3-methoxy-1-propanol, 2-methyl-1-penten-3-ol, 1-ethoxy-ethanol, 3-pentyn-1-ol, 3-pentyn-1-ol, 2-penten-1-ol, 4-hydroxy-butanal, 4-hydroxy-butanal, 2-hydroxy-butanal, 2-penten-3-ol, 2,3-dimethyl-3-buten-1-ol, 3-hydroxy-2-methyl-propanenitrile, 3-methylene-2-pentanol, 2-ethyl-3-buten-1-ol, 3,4-dimethyl-2-pentanol, 2-chloro-2-propanol, 1-(methyldioxy)-ethanol, 2-ethyl-3-butyn-1-ol, benzenemethanol, 2-(ethylthio)-ethanol, 3-ethoxy-1-propanol, 1-chloro-3-fluoro-2-propanol, 1,3-difluoro-2-propanol, 2-3-hydroxy-butanone, 2-methyl-1-hexanol, 2-(ethenyloxy)-ethanol, 2,2-dimethyl-3-buten-1-ol, 4-methyl-4-penten-2-ol, 2-propoxy-ethanol, 3-hydroxy-butanenitrile, 2-fluoro-2-propen-1-ol, 2,4-dimethyl-1-pentanol, 1-methoxy-1-propanol, 2,3-dimethyl-2-buten-1-ol, 3-chloro-2-propen-1-ol, 3-penten-1-ol, 2,4-pentadiyn-1-ol, 2,2-dimethyl-3-butyn-1-ol, 2-ethyl-2,3-butadien-1-ol, 3-chloro-2-propyn-1-ol, 1,1-difluoro-2-propanol, 1,5-hexadiyn-3-ol, 2,3-hexadien-1-ol, 2-penten-2-ol, 1-methoxy-1,2-ethanediol, 2-methylene-3-butyn-1-ol, 2-(chloromethoxy)-ethanol, α-methyl-1-cyclopropene-1-methanol, 2-hydroxy-butanethial, 1-chloro-2-methyl-1-propanol, 3-(methylthio)-1-propanol, 1-hexyn-3-ol, 3-chloro-2-butanol, 1,5-hexadien-3-ol, 5-hexyn-1-ol, 1-chloro-2-butanol, 1-methyl-cyclopropanemethanol, 4-penten-2-yn-1-ol, 5-hydroxy-pentanal, 4-methyl-3-penten-2-ol, 1-hexen-3-ol, 1-hydroxy-2-butanone, 3,4-hexadien-1-ol, 3-chloro-2-methyl-1-propanol, 2-methoxy-1-butanol, 2-ethoxy-1-propanol, 5-hexyn-3-ol, 3-methoxy-2-butanol, 2-methyl-1,4-pentadien-3-ol, 2-methyl-1-penten-4-yn-3-ol, 4,5-hexadien-3-ol, 2-(methylthio)-1-propanol, 2,5-hexadiyn-1-ol, 2-(hydroxymethyl)-butanal, 3-fluoro-2-butanol, 2-(hydroxymethyl)-2-propenal, 2-ethenyl-3-buten-1-ol, 1-(ethylthio)-ethanol, 2-cyclobutene-1-methanol, 2-hydroxy-3-butenal, 2-(1-methylethyl)-3-buten-1-ol, 1-cyclopropene-1-ethanol, 1-fluoro-2-butanol, 3-fluoro-2-methyl-1- propanol, 1-(1-methylethoxy)-ethanol, 3-hydroxy-1-buten-1-one, 3-hexyn-2-ol, 4-ethoxy-1-butanol, 4-fluoro-1-butanol, 5-hexen-2-ol, 2-hexyn-1-ol, 4-chloro-1-butanol, 3-hexyn-1-ol, 1-ethoxy-2-propanol, 4-chloro-2-butanol, 4-methyl-2,3-pentadien-1-ol, 2,4-pentadien-1-ol, 3-propoxy-1-propanol, 2-methylene-1-pentanol, 2,4-pentadien-1-ol, 2-penten-4-yn-1-ol, 2-methyl-4-penten-1-ol, 1-(methylthio)-2-propanol, 4-methyl-2-pentyn-1-ol, 3-hydroxy-2,2-dimethyl-propanenitrile, 4-(methylthio)-1-butanol, 2-chloro-1-butanol, 4,4-dimethyl-1-pentyn-3-ol, 4,5-hexadien-1-ol, 3-methyl-4-penten-1-ol, 3-methylene-1-pentanol, 2,4-hexadiyn-1-ol, 2-(2-hydroxyethoxy)-acetaldehyde, 4,5-hexadien-2-ol, 3-methyl-2-methylene-3-buten-1-ol, 2-methyl-3,4-pentadien-1-ol, 2-cyclopropylidene-ethanol, 4-hydroxy-3-methyl-butanal, 4-3-methylene-penten-2-ol, 2,3-heptadien-1-ol, 2,5-heptadiyn-1-ol, 3-methyl-4-pentyn-1-ol, 2-methyl-4-pentyn-1-ol, 1-cyclobutene-1-methanol, 2-fluoro-1-butanol, 3,4-heptadien-1-ol, 4-fluoro-2-butanol, 2-(1-methylethyl)-2,3-butadien-1-ol, 4-methyl-3-methylene-2-pentanol, 3-hydroxy-2-methyl-butanenitrile, 1-1-methoxy-2-methyl-propanol, 3-ethyl-3,4-pentadien-2-ol, 1-methyl-2-cyclopropene-1-methanol, 3-hexen-1-ol, 2-chloro-2-methyl-1-propanol, 4-hydroxy-butanenitrile, 2-thiiranemethanol, 3-chloro-1-butanol, 2-hexen-1-ol, 3-methoxy-1-butanol, 5-hexen-2-yn-1-ol, 2-(ethenylthio)-ethanol, 2-fluoro-2-methyl-1-propanol, 4-methyl-2-penten-1-ol, 3-heptyn-1-ol, 3-(ethylthio)-1-propanol, 2-[(1-methylethyl)thio]-ethanol, 4-methoxy-2-butanol, 4-hexyn-2-ol, 1-methoxy-2-butanol, 3,3-difluoro-1-propanol, 3-fluoro-1-butanol, 2-chloro-1-methoxy-ethanol, 2,3,5-hexatrien-1-ol, 2-(hydroxymethyl)-butanenitrile, 2,4,6-heptatriyn-1-ol, 1-fluoro-3-methyl-2-butanol, 2-cyclobuten-1-ol, 2-butoxy-ethanol, 2-chloro-2,2-difluoro-ethanol, 2-oxiranemethanol, 1-chloro-3-buten-2-ol, 1-propoxy-2-propanol, 3-hepten-1-ol, 2-propoxy-1-propanol, 2-(propylthio)-ethanol, or 3-cyclopentene-1-methanol.

In some embodiments, the orthoester linker is a compound of formula (II) wherein $R^1$, $R^2$, $R^3$, $R^4$, $R^5$ or $R^6$ is a $C_1$-$C_{24}$ alkyl comprising one or more heteroatom. In some embodiments, the heteroatom is oxygen. In some embodiments, the heteroatom is N. In some embodiments, the heteroatom is a combination of different heteroatoms.

In some embodiments, the orthoester linker is a compound of formula (II) wherein $R^7$ is H.

In some embodiments, the orthoester linker is a compound of formula (II) wherein $R^1$, $R^2$, one of $R^3$ or $R^4$, $R^5$, $R_6$ and $R^7$ are H and the other one of $R^3$ or $R^4$ is a $C_1$-$C_{24}$ alkyl or $C_1$-$C_{24}$ heteroalkyl.

In some embodiments, the orthoester linker is a compound of formula (II) wherein $R^1$, $R^2$, $R^3$, and $R^7$ are hydrogen, and $R^4$ is $C_1$-$C_{24}$ alkyl or $C_1$-$C_{24}$ heteroalkyl.

In some embodiments, the orthoester linker is a compound of formula (II) wherein n is 0.

In some embodiments, the orthoester linker is a compound of formula (II) wherein $R^1$, $R^2$, and $R^3$ are H and $R^4$ is a $C_1$-$C_{24}$ alkyl or $C_1$-$C_{24}$ heteroalkyl; and n is 0 or 1.

In some embodiments, the present invention provides an orthoester linker of formula (III)

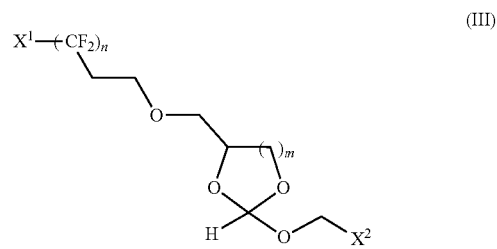

(III)

wherein each of $X^1$ and $X^2$ are independently H or an electron withdrawing group; m is 1 or 2; and n is an integer ranging from 4 to 12.

In some embodiments, the orthoester linker is a compound of formula (III) wherein $X^1$ or $X^2$ is H, $CH_3$, or $CF_3$.

In some embodiments, the orthoester linker is a compound of formula (III) wherein $X^1$ and $X^2$ are H, $CH_3$, or $CF_3$.

In some embodiments, the orthoester linker is a compound of formula (III) wherein $X^1$ and $X^2$ is $CF_3$.

In some embodiments, the orthoester linker is a compound of formula (III) wherein m is 1.

In some embodiments, the orthoester linker is a compound of formula (III) wherein n is an integer from 6 to 12.

In some embodiments, the orthoester linker is a compound of formula (III) wherein n is an integer from 8 to 12.

In some embodiments, the orthoester linker is a compound of formula (IIIa)

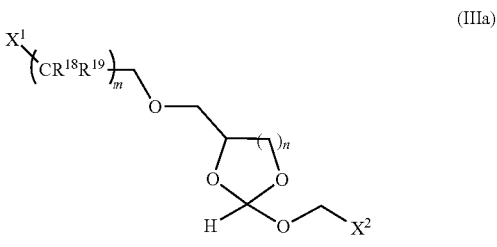

(IIIa)

wherein $X^1$ is H, F, a protected amino group, a protected carboxylic acid, a $C_2$ alkenyl group or a $C_2$ substituted alkenyl group, a $C_2$ alkynyl group or a $C_2$ substituted alkynyl group; $R^{18}$ and $R^{19}$ are each independently H, F, $C_{1-3}$ heteroalkyl or $C_{1-3}$ substituted alkyl; $X^2$ is H, $CH_3$, or $CF_3$; n is 1 or 2; and m is an integer ranging from 0 to 12.

In some embodiments, the orthoester linker is the compound of formula (IIIa), wherein $X^1$ is H, F, an azido, a protected sulfhydryl, a protected poly-sulfhydryl, a polyhistidine, a protected amino group, a protected hydrazide group, a protected oxyamine group, a cyclooctyne, a conjugated diene, a $C_2$ alkenyl group, a $C_2$ substituted alkenyl group, a $C_2$ alkynyl group or a $C_2$ substituted alkynyl group; $R^{18}$ and $R^{19}$ are each independently H, F, $C_{1-3}$ heteroalkyl or $C_{1-3}$ substituted alkyl; $X^2$ is H, $CH_3$, F, Cl, Br, or a mono-, bis- or tris-halosubstituted methyl or cyano-; n is 1 or 2; and m is an integer ranging from 0 to 12.

In some embodiments, the orthoester linker is

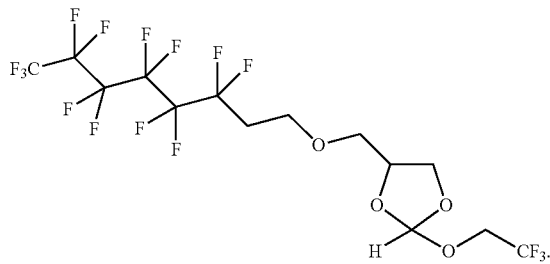 [SMILES: FC(F)(F)COC1OCC(COCCC(F)(F)C(F)(F)C(F)(F)C(F)(F)C(F)(F)C(F)(F)F)O1]

The orthoester linkers of the present invention can be prepared using any suitable method. In some embodiments, an orthoester linker is formed by reacting a 1,2-diol, 1,3-diol, or 1,4-diol with an alcohol in the presence of an acid. In some embodiments, the acid is used in a substoichiometric amount. In some embodiments, the acid is a Brönsted acid. In some embodiments, the acid is a Lewis acid. In certain embodiments, the acid is a dilute mineral acid (e.g., at a concentration of about 0.2 M or less). In some embodiments, the alcohol has a boiling point of from about 30° C. to about 120° C. Thus, in some embodiments, the alcohol has a boiling point of from about 30° C. to about 120° C., from about 30° C. to about 110° C., from about 30° C. to about 100° C., from about 30° C. to about 95° C., from about 30° C. to about 90° C., from about 30° C. to about 85° C., from about 30° C. to about 80° C., from about 30° C. to about 75° C., from about 30° C. to about 70° C., from about 30° C. to about 65° C., from about 30° C. to about 60° C, from about 30° C. to about 55° C., from about 30° C. to about 50° C., from about 35° C. to about 120° C., from about 40° C. to about 120° C., from about 45° C. to about 120° C., from about 50° C. to about 120° C., from about 55° C. to about 120° C., from about 60° C. to about 120° C., from about 40° C. to about 100° C., from about 50° C. to about 100° C., from about 40° C. to about 90° C., or from about 40° C. to about 80° C.

In another embodiment, the present invention provides an oligonucleotide (i.e., an oligonucleotide-orthoester linker conjugate) comprising a moiety of formula (IV)

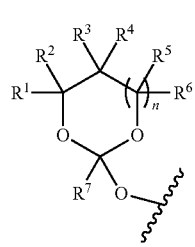

(IV)

wherein each of $R^1$, $R^2$, $R^3$, $R^4$, $R^5$, $R^6$ and $R^7$ is independently H, $C_1$-$C_{24}$ alkyl, $C_1$-$C_{24}$ heteroalkyl, $C_2$-$C_{24}$ alkenyl, $C_2$-$C_{24}$ heteroalkenyl $C_2$-$C_{24}$ alkynyl, $C_2$-$C_{24}$ heteroalkynyl, halogen, aryl, heteroaryl, heterocyclyl, substituted $C_1$-$C_{24}$ alkyl, substituted $C_2$-$C_{24}$ alkenyl, substituted $C_2$-$C_{24}$ alkynyl, substituted aryl, substituted heteroaryl or substituted heterocyclyl; and n is 0, 1, or 2, wherein at least one of $R^1$, $R^2$, $R^3$, $R^4$, $R^5$, $R^6$ or $R^7$ comprises an affinity tag. Preferably, $R^7$ is H.

When n is 2, the orthoester linker moiety forms a 7-member ring cyclic orthoester as shown in the following structure, and has two additional R groups $R'_5$ and $R'_6$ on the additional carbon which are defined each independently, as any of $R^1$ to $R^6$ groups:

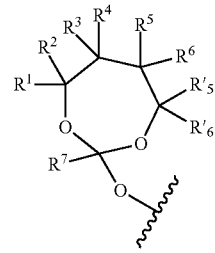

In the moiety of the formula (IV), the oxygen linked to the squiggly line is the oxygen of the 5'end or the 3'end of the oligonucleotide.

In the moiety of the formula (IV), at least one of $R^1$, $R^2$, $R^3$, $R^4$, $R^5$, $R^6$ and $R^7$ may be $C_1$-$C_{24}$ alkyl, $C_1$-$C_{24}$ heteroalkyl, $C_2$-$C_{24}$ alkenyl, $C_2$-$C_{24}$ heteroalkenyl, $C_2$-$C_{24}$ alkynyl, $C_2$-$C_{24}$ heteroalkynyl, halogen, aryl, heteroaryl, heterocyclyl, carbocyclyl, any substituted equivalent or a combination thereof and the remaining $R^1$, $R^2$, $R^3$, $R^4$, $R^5$, $R^6$ and $R^7$ may be H, $C_1$-$C_6$ alkyl, $C_2$-$C_6$ alkenyl, $C_2$-$C_6$ alkynyl, $C_6$-$C_{12}$ arylalkyl, carbocyclyl, heterocyclyl, any substituted equivalent or combination thereof; and n is 0, 1, or 2, wherein at least one of $R^1$, $R^2$, $R^3$, $R^4$, $R^5$, $R^6$ or $R^7$ comprises an affinity tag; and with the proviso that said moiety is not

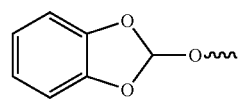

In some of these oligonucleotide orthoester linker conjugates, n=0 and the affinity tag is a fluorous or a hydrophobic tag with a cLog P value of at least 3.

These oligonucleotide orthoester linker conjugates include those in which the oligonucleotide comprises an oligoribonucleic acid (RNA).

In the oligonucleotide orthoester linker conjugates, at least one of $R^1$, $R^2$, $R^3$, $R^4$, $R^5$ or $R^6$ may be a fluorosubstituted alkyl, a fluorosubstituted alkenyl, a fluorosubstituted alkynyl, a fluorosubstituted aryl, a fluorosubstituted heteroalkyl, a fluorosubstituted heteroalkenyl, a fluorosubstituted heteroalkynyl, or a fluorosubstituted heterocyclyl.

In the oligonucleotide orthoester linker conjugates, at least one of $R^1$, $R^2$, $R^3$, $R^4$, $R^5$ or $R^6$ may be a fluorous tag and the remaining R groups including $R^7$ may be H.

In the oligonucleotide orthoester linker conjugates, at least two of $R^1$, $R^2$, $R^3$, $R^4$, $R^5$ or $R^6$ may be a fluorous tag.

In the oligonucleotide orthoester linker conjugates, moiety of the Formula (IV) may be selected from the group consisting of:

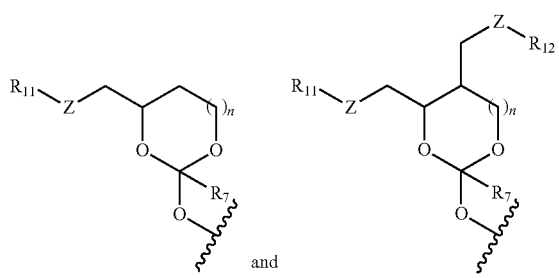

wherein $R^{11}$ and $R^{12}$ are each independently H, $C_1$-$C_{23}$ alkyl, $C_1$-$C_{23}$ heteroalkyl, $C_1$-$C_{23}$ substituted alkyl, $C_2$-$C_{23}$ alkenyl, $C_2$-$C_{23}$ heteroalkenyl, $C_2$-$C_{23}$ substituted alkenyl, $C_2$-$C_{23}$ alkynyl, $C_2$-$C_{23}$ heteroalkynyl, $C_2$-$C_{23}$ substituted alkynyl, aryl, substituted aryl, heteroaryl, substituted heteroaryl, heterocyclyl or substituted heterocyclyl provided that at least one of $R^{11}$ and $R^{12}$ comprises an affinity tag; $R^7$ is H, methyl, ethyl, n-propyl, phenyl or benzyl; Z are each independently $CR^a R^b$, O, S or $NR^a$ wherein $R^a$ and $R^b$ are each independently H, $C_1$-$C_6$ alkyl, or $R^a$ and $R^{11}$ or $R^a$ and $R^{12}$ together form a heterocycle with N; n is 0, 1, or 2.

The moiety of the formula (IV) may have the following structure:

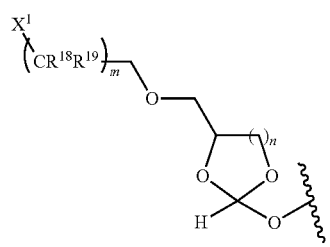

wherein $X^1$ is H, F, an azido, a protected sulfhydryl, a protected poly-sulfhydryl, a poly-histidine, a protected amino group, a protected hydrazide group, a protected oxyamine group, a maleimide, a cyclooctyne, a conjugated diene, a $C_2$ alkenyl group, a $C_2$ substituted alkenyl group, a $C_2$ alkynyl group or a $C_2$ substituted alkynyl group; $R^{18}$ and $R^{19}$ are each independently H, F, $C_{1-3}$ heteroalkyl or $C_{1-3}$ substituted alkyl; n is 1 or 2; and m is an integer ranging from 0 to 12.

The moiety of the formula (IV) may be selected from the group consisting of:

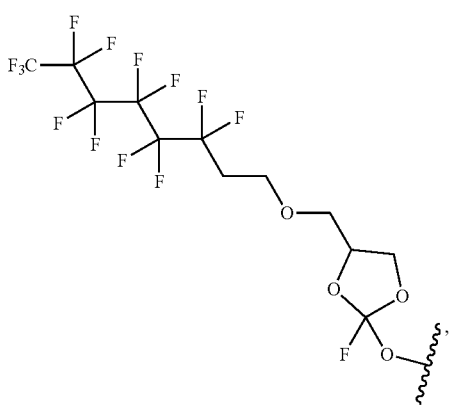

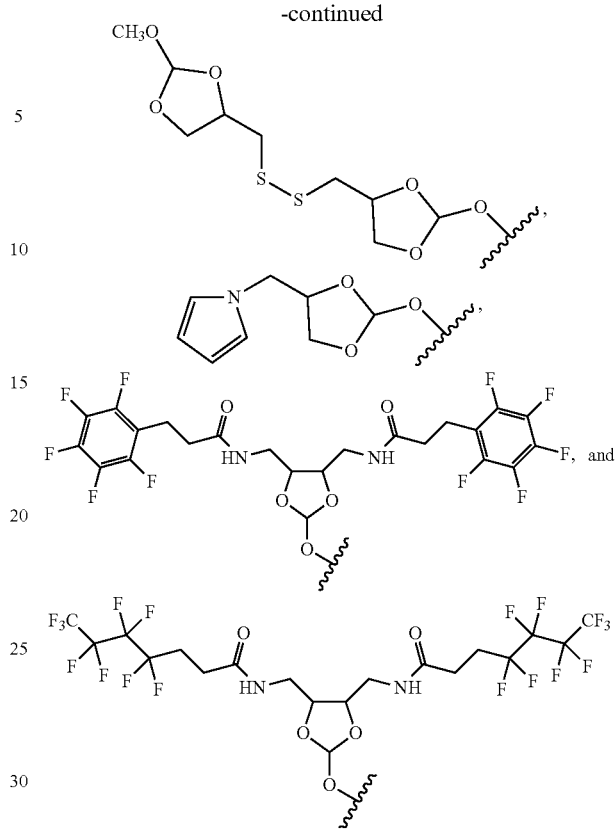

In some embodiments, the oligonucleotide is attached to an orthoester linker at the 5'-position. In some embodiments, the oligonucleotide is attached to the orthoester linker at the 3'-position.

In some embodiments, the oligonucleotide is ribonucleic acid (RNA). In some embodiments, the oligonucleotide is deoxyribonucleic acid (DNA). In some embodiments, the oligonucleotide is at least 25 nucleotides in length. In some embodiments, the oligonucleotide is at least 50 nucleotides in length. In some embodiments, the oligonucleotide is at least 75 nucleotides in length. In some embodiments, the oligonucleotide is at least 100 nucleotides in length. In some embodiments, the oligonucleotide is at least 125 nucleotides in length. In some embodiments, the oligonucleotide is at least 150 nucleotides in length.

In some embodiments, the oligonucleotide comprises a moiety of formula (IV) wherein $R^1$, $R^2$, $R^3$, or $R^4$ is a $C_1$-$C_{24}$ alkyl comprising a heteroatom. In some embodiments, the heteroatom is oxygen.

In some embodiments, n is 0.

In some embodiments, $R^5$ is H.

In some embodiments, $R^6$ is H.

In some embodiments, $R^1$, $R^2$, and $R^3$ are hydrogen, and $R^4$ is $C_6$-$C_{24}$ arylalkyl or substituted equivalent, In some embodiments, $R^1$, $R^2$, and $R^3$ are H and $R^4$ is a $C_1$-$C_{24}$ alkyl or substituted alkyl.

In some embodiments, $R^1$, $R^2$, and $R^3$ are H and $R^4$ is a $C_1$-$C_{24}$ alkyl optionally comprises one or more heteroatom; and n is 0 or 1.

In some embodiments, $R^1$ is $C_4$-$C_{24}$ alkyl or heteroalkyl and comprises at least 9 fluorine atoms.

In some embodiments, the oligonucleotide comprises a moiety

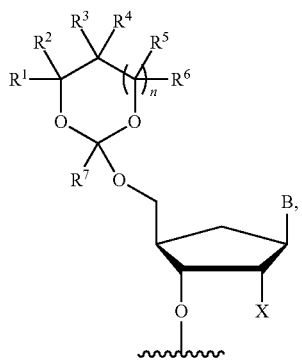

wherein each of $R^1$, $R^2$, $R^3$, $R^4$, $R^5$, $R^6$ and $R^7$ is independently H, $C_1$-$C_{24}$ alkyl, $C_1$-$C_{24}$ heteroalkyl, $C_2$-$C_{24}$ alkenyl, $C_2$-$C_{24}$ heteroalkenyl $C_2$-$C_{24}$ alkynyl, $C_2$-$C_{24}$ heteroalkynyl, halogen, aryl, heteroaryl, heterocyclyl, substituted $C_1$-$C_{24}$ alkyl, substituted $C_2$-$C_{24}$ alkenyl, substituted $C_2$-$C_{24}$ alkynyl, substituted aryl, substituted heteroaryl or substituted heterocyclyl; X is H, F, hydroxyl, protected hydroxyl, alkoxyl, or alkoxyalkyl; n is 0, 1, or 2; and B is a nucleoside base, wherein at least one of $R^1$, $R^2$, $R^3$, $R^4$, $R^5$, $R^6$ or $R^7$ comprises an affinity tag.

In some embodiments, the oligonucleotide comprises a moiety

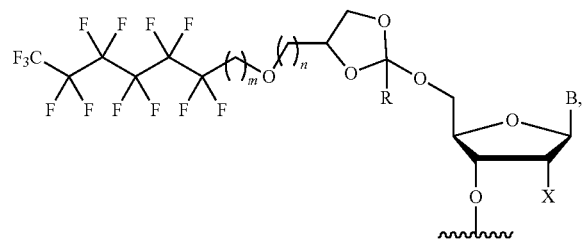

wherein R is H, $C_1$-$C_{24}$ alkyl, $C_2$-$C_{24}$ alkenyl, $C_2$-$C_{24}$ alkynyl, halosubstituted alkyl, aryl, heteroaryl, or heterocycle; X is H, F, hydroxyl, protected hydroxyl, alkoxyl, or alkoxyalkyl; each of m and n is independently 0, 1, or 2; and B is a nucleoside base.

In some embodiments, the oligonucleotide comprises a moiety

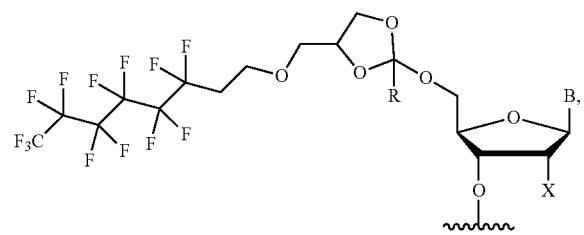

wherein R is H, $C_1$-$C_{24}$ alkyl, $C_2$-$C_{24}$ alkenyl, $C_2$-$C_{24}$ alkynyl, halosubstituted alkyl, aryl, heteroaryl, or heterocycle; X is H, F, hydroxyl, protected hydroxyl, alkoxyl, or alkoxyalkyl; and B is a nucleoside base.

In another embodiment, the present disclosure provides a method of synthesizing an oligonucleotide (i.e., an oligonucleotide-orthoester linker conjugate) comprising a moiety of formula (IV)

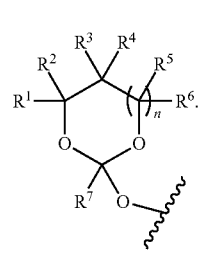

(IV)

The method comprises contacting an oligonucleotide with an orthoester linker to form the oligonucleotide comprising a moiety of formula (IV), wherein each of $R^1$, $R^2$, $R^3$, $R^4$, $R^5$, $R^6$ and $R^7$ is independently H, $C_1$-$C_{24}$ alkyl, $C_1$-$C_{24}$ heteroalkyl, $C_2$-$C_{24}$ alkenyl, $C_2$-$C_{24}$ heteroalkenyl $C_2$-$C_{24}$ alkynyl, $C_2$-$C_{24}$ heteroalkynyl, halogen, aryl, heteroaryl, heterocyclyl, substituted $C_1$-$C_{24}$ alkyl, substituted $C_2$-$C_{24}$ alkenyl, substituted $C_2$-$C_{24}$ alkynyl, substituted aryl, substituted heteroaryl or substituted heterocyclyl; and n is 0, 1, or 2, wherein at least one of $R^1$, $R^2$, $R^3$, $R^4$, $R^5$, $R^6$ or $R^7$ comprises an affinity tag.

In some embodiments, the oligonucleotide is reacted with an orthoester linker in the presence of an acid. In some embodiments, the reaction is an acid-catalyzed exchange reaction. In some embodiments, the acid is a Brönsted acid. In some embodiments, the acid is a Lewis acid. In some embodiments, the acid is a mineral acid such as hydrochloric acid, sulfuric acid, or nitric acid. In some embodiments, the oligonucleotide is reacted with an orthoester in the presence of a mineral acid at an acid concentration of about 0.2 M or less. In some embodiments, the acid is an organic acid such as acetic acid or a derivative thereof such as di- or trichloroacetic acid, formic acid, benzoic acid, toluenesulfonic acid, and triflic acid. In some embodiments, the acid is sodium acetate (pH=5.5), $BF_3 \cdot Et_2O$, $SiO_2$, montmorillonite-K10, montmorillonite-KSF, or Amberlyst-15.

In some embodiments, the orthoester linker reacts with a hydroxyl group that is liberated on the final nucleotide synthon by a deblocking step after it has been coupled via an acid catalyzed reaction, as shown in the illustrative example below.

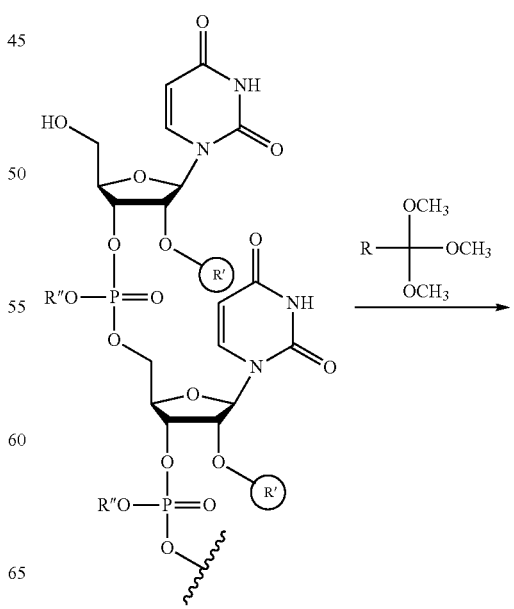

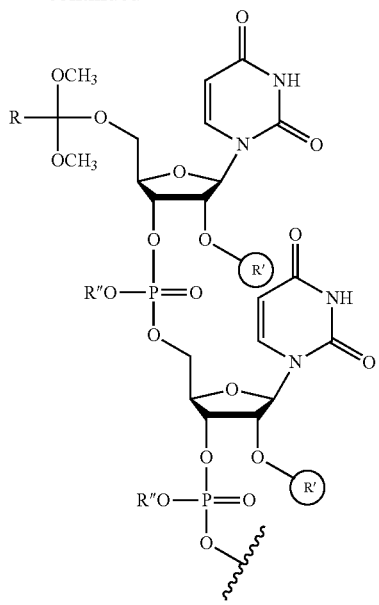

In some embodiments, the orthoester linker present in one of the monomer synthon's blocking groups and that unique monomer synthon is used in the final coupling step, as shown in the illustrative example below.

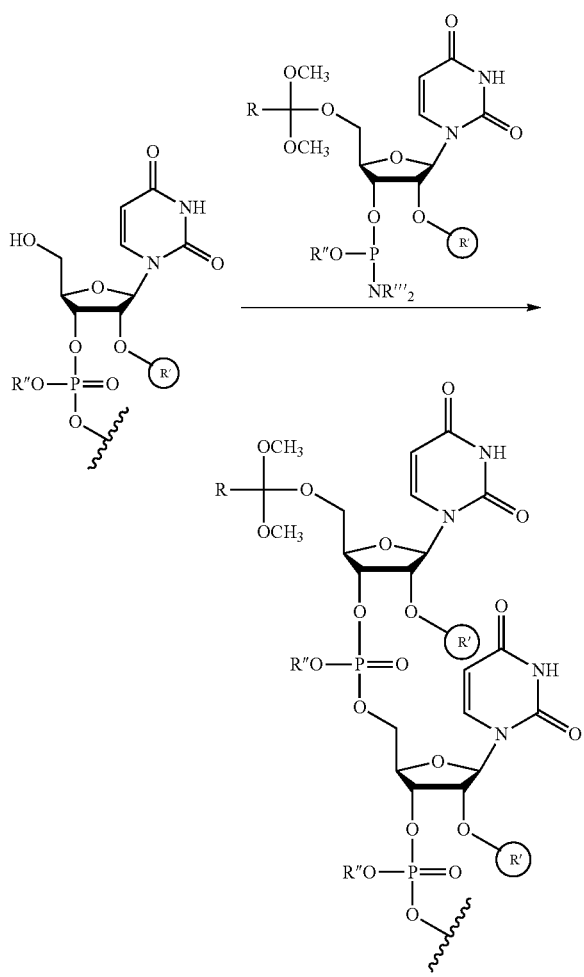

Figure 9:
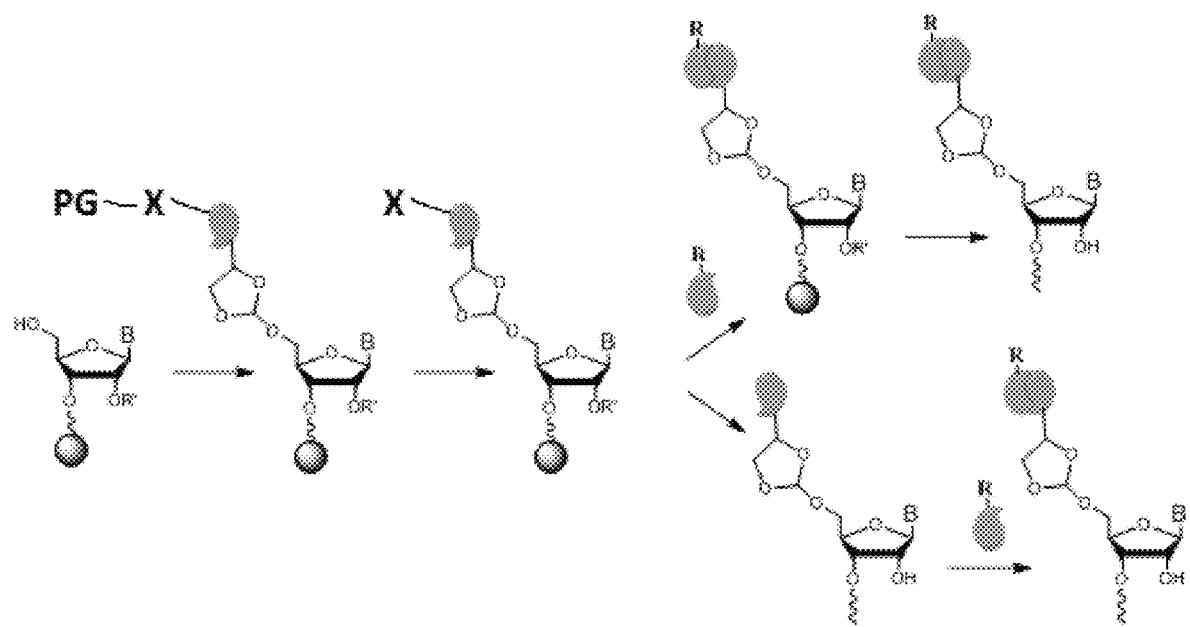
FIGS. 9 and 10 illustrate that an affinity tag, represented by the R group, can be attached to the oligonucleotide prior to or after deprotection and cleavage from the solid support.
Figure 10:
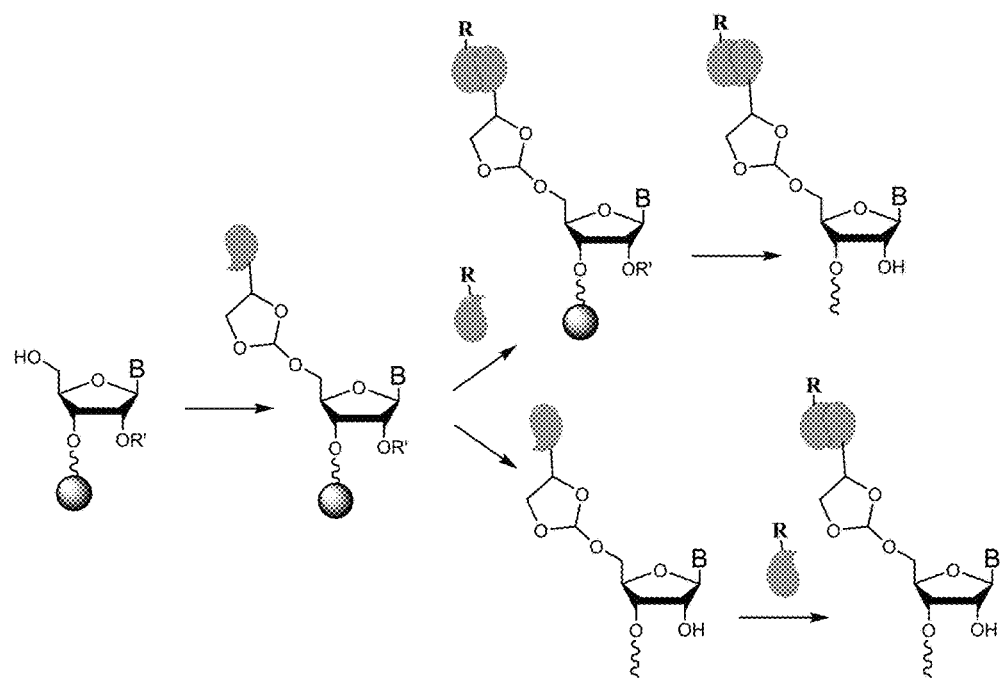

In certain embodiments, the affinity tag is attached to the orthoester linker after the linker has been attached to the oligonucleotide, as shown in FIGS. 9 and 10. The affinity tag, represented by the R group, can either be attached to the oligonucleotide prior to deprotection and cleavage from the solid support or it can be attached to the orthoester linker after deprotection and cleavage from the solid support. The R group can be any affinity tag. In some embodiments, the R group is an affinity tag selected from a fluorosubstituted alkyl, fluorosubstituted alkenyl, fluorosubstituted alkynyl, and fluorosubstituted aryl substituent. In some embodiments, the R group can be attached to the orthoester linker using olefin metathesis, cycloaddition reaction (e.g., Diels-Alder reaction, 4+1 cycloaddition, 3+2 cycloaddition, norbornene cycloaddition, oxanorbornadiene cycloaddition), click chemistry (e.g., tetrazole photoclick chemistry, copper-catalyzed click chemistry, strain-promoted click chemistry), Suzuki cross-coupling, Staudinger ligation, Michael addition, quadricyclane ligation, tetrazine ligation, or oxidative coupling. Other conjugation schemes well known in the art can be employed to link the affinity tag to the orthoester linker moiety. Non-limiting example of these conjugation include reacting an amine terminated moiety with a N-hydrosuccinamide (NHS) moiety or other activated ester, a thiol-terminated moiety with an alpha-halocarbonyl containing moiety and the like.

In certain embodiments, the orthoester linker contains a chemical moiety (e.g. thiol, amine, alcohol, etc.) that is blocked from reacting with a protecting group. After attachment of the orthoester linker, the protecting group can be removed and the chemical moiety can react covalently and specifically with another chemical moiety on a solid-phase.

The oligonucleotide may be deprotected to remove the orthoester protecting group using any suitable method. In some embodiments, the oligonucleotide-orthoester linker conjugate is deprotected using an acid. In some embodiments, the acid is in a catalytic amount (i.e., substoichiometric amount). In some embodiments, the acid is a Brönsted acid. In some embodiments, the acid is a Lewis acid. In some embodiments, the acid is a mineral acid such as hydrochloric acid, sulfuric acid, or nitric acid. In some embodiments, the oligonucleotide-orthoester linker conjugate is deprotected in the presence of a mineral acid at an acid concentration of about 0.2 M or less. In some embodiments, the acid is an organic acid such as acetic acid, formic acid, benzoic acid, toluenesulfonic acid, and triflic acid. In some embodiments, the acid is $BF_3.Et_2O$, $SiO_2$, montmorillonite K10, montmorillonite-KSF, or Amberlyst-15.

In some embodiments, the oligonucleotide-orthoester linker conjugate is deprotected under mildly acidic conditions. In some embodiments, the oligonucleotide-orthoester linker conjugate is deprotected at a pH of about 3 or more. Thus, in some embodiments, the oligonucleotide-orthoester linker conjugate is deprotected at a pH of about 3 or more, about 3.5 or more, about 4 or more, about 4.5 or more, about 5 or more, about 5.5 or more, about 6 or more, about 6.5 or more, or about 7 or more. In some embodiments, the oligonucleotide is deprotected at a pH of from about 3 to about 7. Thus, in some embodiments, the oligonucleotide is deprotected at a pH of from about 3 to about 7, from about 3.5 to about 7, from about 4 to about 7, from about 4.5 to about 7, from about 5 to about 7, from about 5.5 to about 7, from about 6 to about 7, from about 3 to about 6.5, from about 3 to about 6, from about 3 to about 5, or from about 4 to about 6.

In some embodiments, the oligonucleotide product has a purity of at least about 60% after removal of the orthoester.

Thus, in some embodiments, the oligonucleotide product has a purity of at least about 80%, at least about 85%, at least about 90%, at least about 92%, at least about 94%, at least about 95%, at least about 96%, at least about 97%, at least about 98%, at least about 99%, at least about 99.5%, at least about 99.9%, at least about 99.95%, or at least about 99.99% after removal of the orthoester. In some embodiments, the oligonucleotide product comprises one or more impurities at an amount of about 20% or less, about 15% or less, about 10% or less, about 9% or less, about 8% or less, about 7% or less, about 6% or less, about 5% or less, about 4% or less, about 3% or less, about 2% or less, about 1% or less, about 0.5% or less, about 0.1% or less, about 0.05% or less, or about 0.01% or less.

The oligonucleotides of the present disclosure can be purified using any suitable chromatographic method. In some embodiments, oligonucleotide-orthoester linker conjugate is purified using fluorous affinity chromatography. In some embodiments, the oligonucleotide-orthoester linker conjugate is purified using column chromatography. In some embodiments, the oligonucleotide-orthoester linker conjugate is purified using liquid chromatography (e.g., high pressure liquid chromatography).

In some embodiments, the oligonucleotide-orthoester linker conjugate is purified using fluorous affinity chromatography. Fluorous affinity chromatography utilizes the concept of fluorophilicity where fluorinated compounds tend to have affinity for other fluorinated compounds. In some embodiments, the oligonucleotide is attached to an orthoester comprising a fluorous tag. The oligonucleotide-orthoester linker conjugate is passed through a fluorous column. The fluorous column generally comprises a polymer resin to which fluorinated organic groups are bound. In some embodiments, the oligonucleotide-orthoester linker conjugate binds strongly to the column, while the non-labeled impurities (e.g., truncated or failed sequences) do not interact with the column and pass through the column. Subsequent washing does not release the fluorinated oligonucleotide-orthoester linker conjugate from the column due to the strength of fluorophilic interaction with the fluorous column. After all the impurities have been removed from the column, the oligonucleotide-orthoester linker conjugate is released from the column via cleavage of the oligonucleotide from the orthoester protecting group. The oligonucleotide is generally cleaved under mildly acidic conditions, which breaks interactions between the oligonucleotide and the fluorous column. The oligonucleotide is then eluted from the column using an appropriate solvent, yielding a purified oligonucleotide.

In some embodiments, the oligonucleotide-orthoester linker conjugate purified using high performance liquid chromatography (HPLC). In some embodiments, an oligonucleotide is attached to the orthoester linker and introduced into an HPLC system for purification. The orthoester oligonucleotide-orthoester linker conjugate is generally introduced into the HPLC as a mixture comprising at least one impurity. In some embodiments, the present method allows for separation of oligonucleotide product from impurities of a similar size. The at least one impurity may be of any type. In some embodiments, the at least one impurity is a truncated or failure sequence produced during an oligonucleotide synthesis. In some embodiments, the orthoester oligonucleotide-orthoester linker conjugate is purified using reverse-phase HPLC. In such embodiments, the oligonucleotide-orthoester linker conjugate is purified on a reverse-phase column (e.g., $C_5$ or $C_{18}$ hydrocarbon column). In some embodiments, the oligonucleotide-orthoester linker conjugate is purified is purified on a normal-phase HPLC column. In some embodiments, the oligonucleotide-orthoester linker conjugate is collected from the HPLC system and deprotected to yield the desired oligonucleotide. The HPLC system may comprise an injector, pump, an HPLC column, and a detector. In some embodiments, the detector is an absorbance detector (e.g., UV/VIS or PDA), refractive-index detector, scattering detector (e.g., evaporative or multi-angle), mass spectrometer, conductivity detector, fluorescence detector, chemiluminescence detector, optical rotation detector, or electrochemical detector. In some embodiments, the HPLC system is a triple quadrupole LC-MS, Orbitrap LC-MS, Ion Trap LC-MS, or TOF LC-MS. In some embodiments, the purification method is partially or fully automated.

In some embodiments, the oligonucleotide-orthoester linker conjugate is purified using a cartridge comprising a compound that binds an affinity moiety on the oligonucleotide-orthoester linker conjugate.

In some embodiments, the oligonucleotide is synthesized on a multiplex synthesis platform and the isolation of the oligonucleotides is performed in parallel on a multiplex purification platform.

In some embodiments, the multiplex synthesis or purification platform allows to perform the purification in parallel of 4, 12, 48, 96, 192, or 384 oligonucleotide syntheses.

Some compounds of the present invention may contain asymmetric centers and can thus occur as racemates and racemic mixtures, single enantiomers, diastereomeric mixtures and individual diastereomers. Additional asymmetric centers may be present depending upon the nature of the various substituents on the molecule. Each such asymmetric center will independently produce two optical isomers and it is intended that all of the possible optical isomers and diastereomers in mixtures and as pure or partially purified compounds are included within the scope of this invention. The present invention is meant to comprehend all such isomeric forms of these compounds.

Referring to FIG. 1, it is a schematic of a typical chemical synthesis of an oligonucleotide on a solid support. The typical desired oligonucleotide product contains an internucleotide bond between the 5'-hydroxyl and 3'-hydroxyl of adjacent nucleotides. To accomplish the synthesis, the first step of the synthesis cycle is generally the reaction of a protected monomer with a nucleoside attached to the surface or reaction of a protected monomer with a hydroxyl group on the surface. The hydroxyl group on the surface can either be part of a cleavable universal linker or non-cleavable surface attachment. After initial coupling of the reactive phosphorus group with a hydroxyl on the surface, the steps that follow typically include capping of unreacted hydroxyl groups and then oxidation of the reactive phosphorus intermediate. Under certain conditions where certain modified phosphorus groups are being used, it may be necessary to oxidize prior to capping, especially in the case where the oxidation reagent produces a modified phosphorus group such as a phosphorothioate, boranophosphonate, or phosphoramidate. The final step is usually the deblocking of the hydroxyl group that will couple to the next protected nucleotide monomer. The protecting group removed in this final step is generally a dimethoxytrityl group (DMT). However, many other protective groups are well known in the art such as, for example, the 9-phenylxanthyl group (Pixyl), benzhydryloxy-bis(trimethylsilyloxy)silyl (BZH). Upon the completion of the chain assembly, the desired product is released from the solid phase, deprotected, and utilized in further biological applications.

Figure 2:
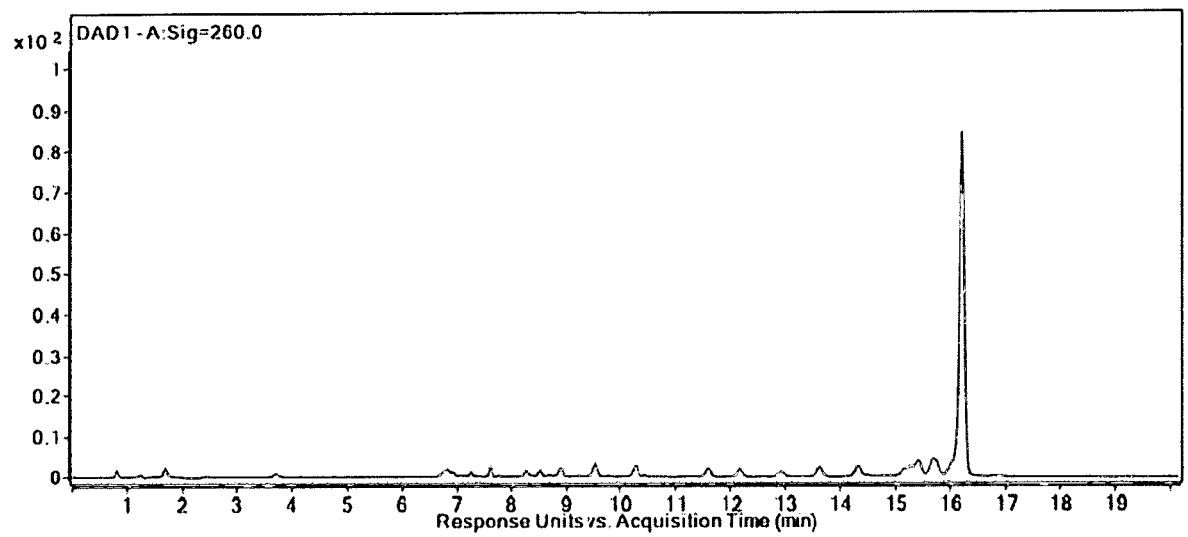
FIG. 2 shows a diode array detector (DAD) spectrum of a crude oligonucleotide mixture comprising a full-length sequence and multiple failure sequences where the full-length sequence is the largest peak.

Referring to FIG. 2, it shows a diode array detector (DAD) spectrum of a crude oligonucleotide mixture obtained in chemical synthesis on solid support. The mixture comprises a full-length target oligonucleotide and multiple failure truncated oligonucleotides which are byproducts of the synthesis. As shown in FIG. 2, the full-length target oligonucleotide is the largest peak.

Figure 3:
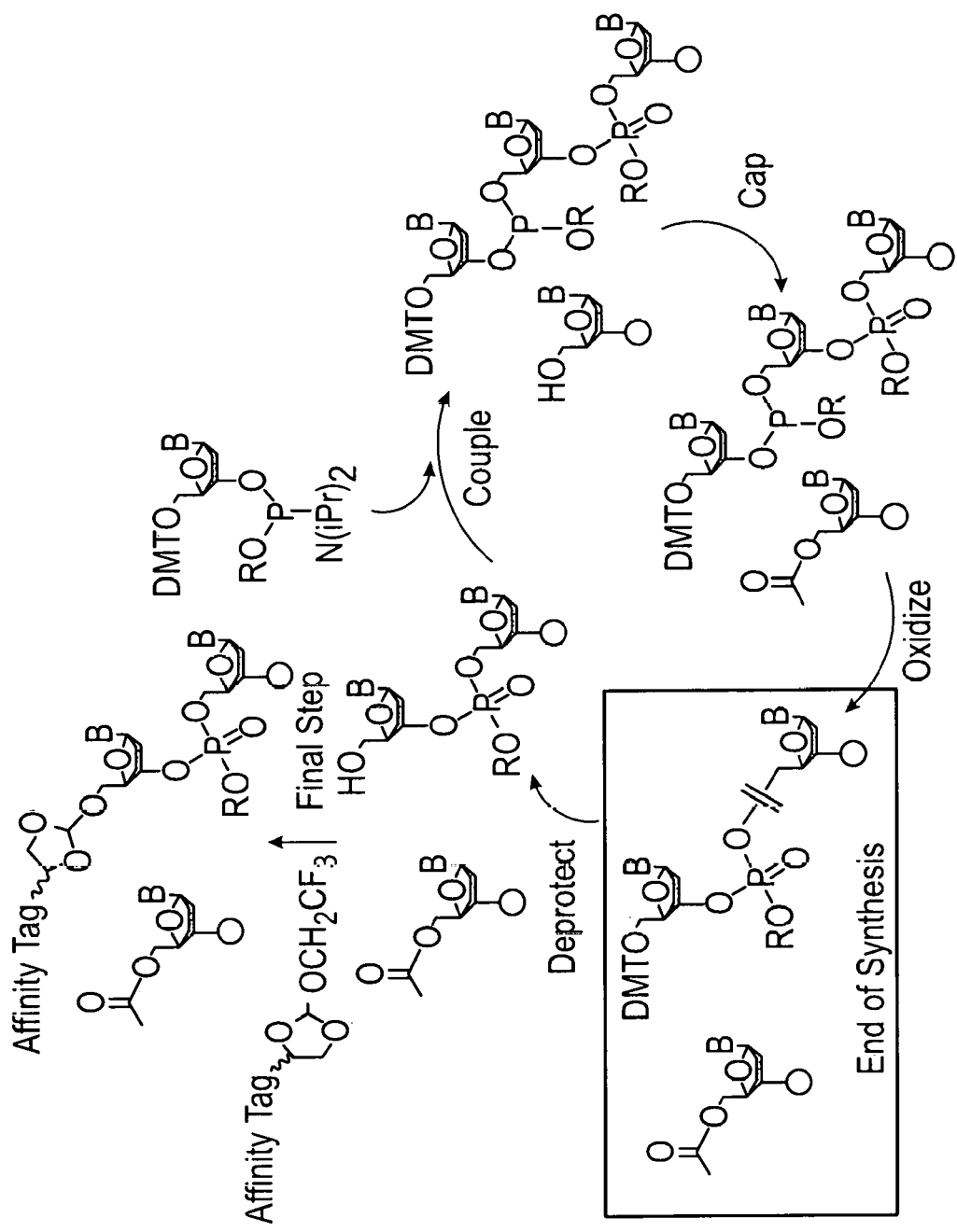
FIG. 3 shows a typical chemical synthesis of oligonucleotides in which the 5'-hydroxyl of the truncated or failure sequences were capped with an acetyl protecting group while the full-length oligonucleotides bear a dimethoxytrityl (DMT) protecting group on their 5'-termini, allowing for specific removal of the DMT group and region-specific addition of the orthoester linker at the 5'-position of the full length oligonucleotides.

Referring to FIG. 3, it is a schematic of a typical chemical synthesis of oligonucleotides in which the 5'-hydroxyl of the truncated or failure sequences were capped with an acetyl protecting group while the full-length oligonucleotides bear a dimethoxytrityl (DMT) protecting group on their 5'-termini, allowing for specific removal of the DMT group and region-specific addition of the orthoester linker at the 5'-position of the full length oligonucleotides.

Figure 4:
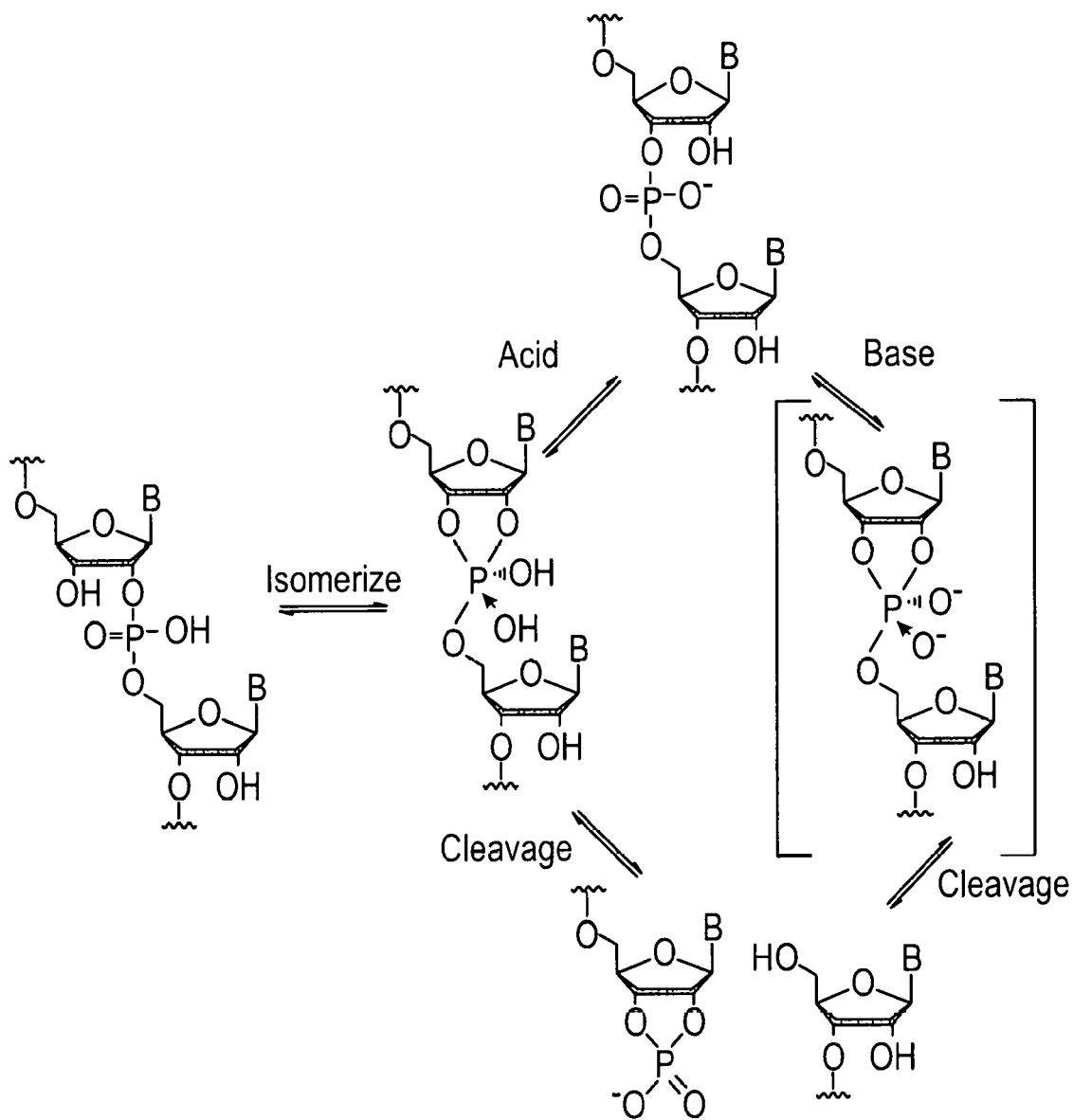
FIG. 4 shows an acid cleavage of the internucleotide bond of an RNA and isomerization of the internucleotide bond resulting in a mixture of 5'-3' and 5'-2' linked RNA products.

Referring to FIG. 4, it is a schematic of an acid cleavage of the internucleotide bond of an RNA and isomerization of the internucleotide bond resulting in a mixture of 5'-3' and 5'-2' linked RNA products.

Figure 5:
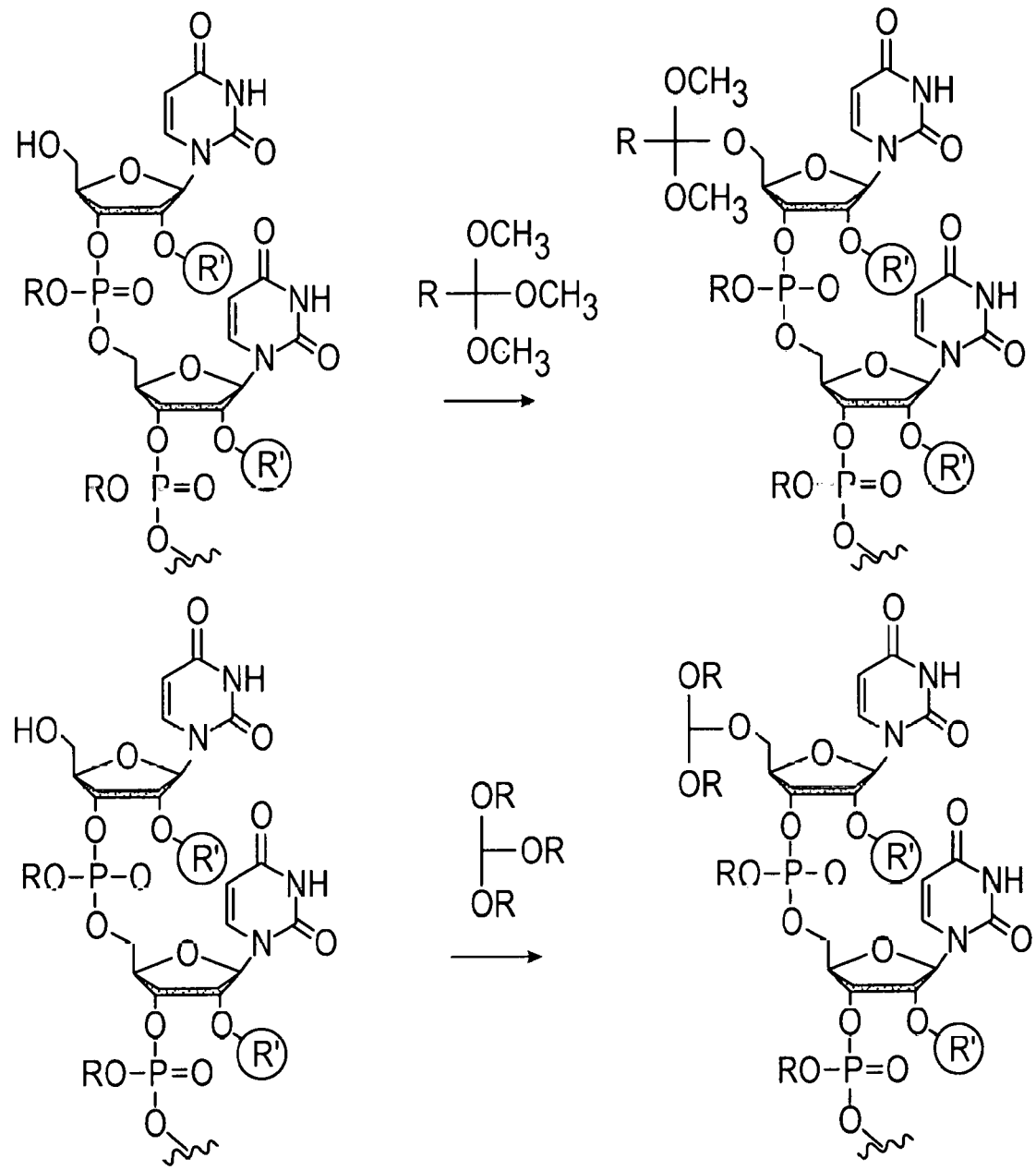
FIG. 5 shows protection of an oligonucleotide with an acyclic orthoester linker where an affinity tag is located on the R group linked to the central carbon of the orthoester or on all the R groups of the orthoester yielding an orthoester conjugated oligonucleotide with two affinity tags.

Referring to FIG. 5, it is a schematic of protecting an oligonucleotide with an acyclic orthoester linker. In the upper panel, an affinity tag is located on the R group linked to the central carbon of the orthoester linker. Reacting an oligonucleotide with this orthoester linker yields an oligonucleotide-orthoester linker conjugate with one affinity tag. In the lower panel, an affinity tag is located on all three R groups of the orthoester linker. This reaction yields an orthoester linker conjugated oligonucleotide with two affinity tags.

Figure 6:
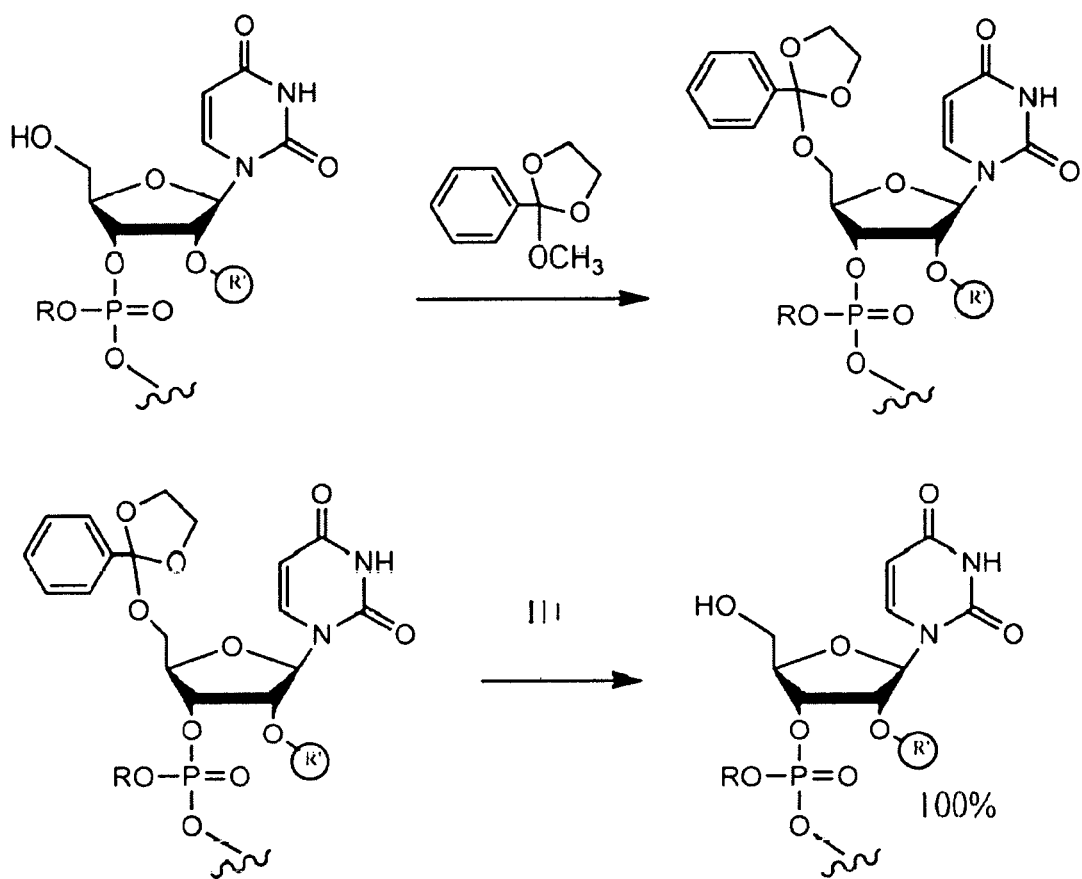
FIG. 6 shows protection of an oligonucleotide with a cyclic orthoester and acid-promoted cleavage of the orthoester protecting group.

Referring to FIG. 6, the upper panel is a schematic of protecting an oligonucleotide with a cyclic orthoester. The lower panel is a schematic of acid-promoted cleavage of the orthoester protecting group.

Figure 7:
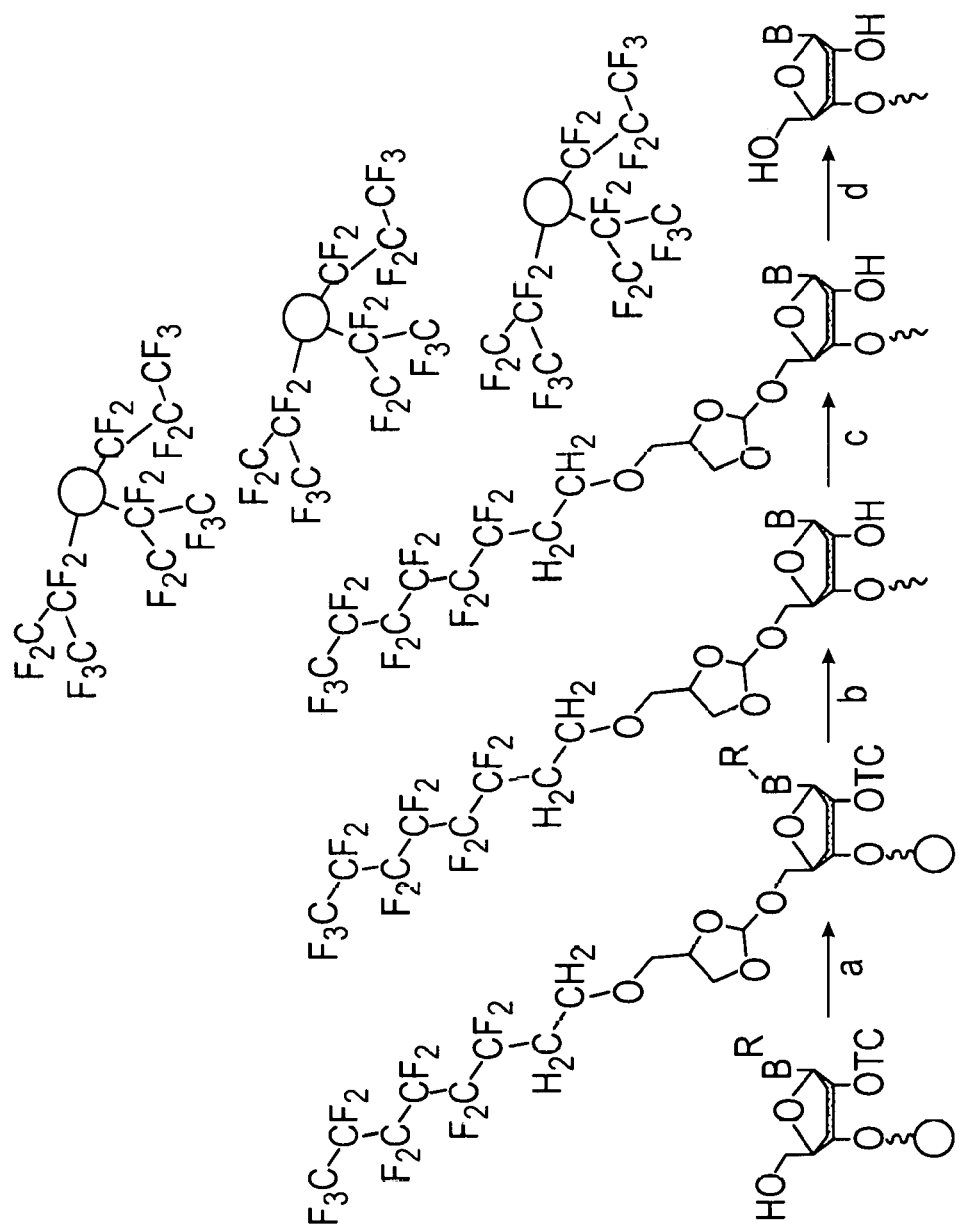
FIG. 7 shows the purification workflow of an oligonucleotide using an orthoester linker comprising a fluorous affinity tag. The workflow shows a four-step process in which the oligonucleotide is first conjugated to the fluorosubstituted orthoester linker, then the oligonucleotide portion of the oligonucleotide orthoester linker conjugate is deprotected and cleaved from the solid support, then the oligonucleotide orthoester linker conjugate is purified using the fluorous affinity tag either by HPLC or solid phase extraction. In the last step, the fluorosubstituted orthoester linker is cleaved from the oligonucleotide yielding the desired purified product oligonucleotide.

Referring to FIG. 7, it is a schematic of the purification workflow of an oligonucleotide using an orthoester linker comprising a fluorous affinity tag. The workflow shows a four-step process in which the oligonucleotide is first conjugated to the fluorosubstituted orthoester linker in step a. In step b, the oligonucleotide portion of the oligonucleotide orthoester linker conjugate is deprotected and cleaved from the solid support. In step c, the oligonucleotide orthoester linker conjugate is purified using the fluorous affinity tag either by HPLC or solid phase extraction. In step d, the fluorosubstituted orthoester linker is cleaved from the oligonucleotide yielding the desired purified product oligonucleotide.

Figure 8:
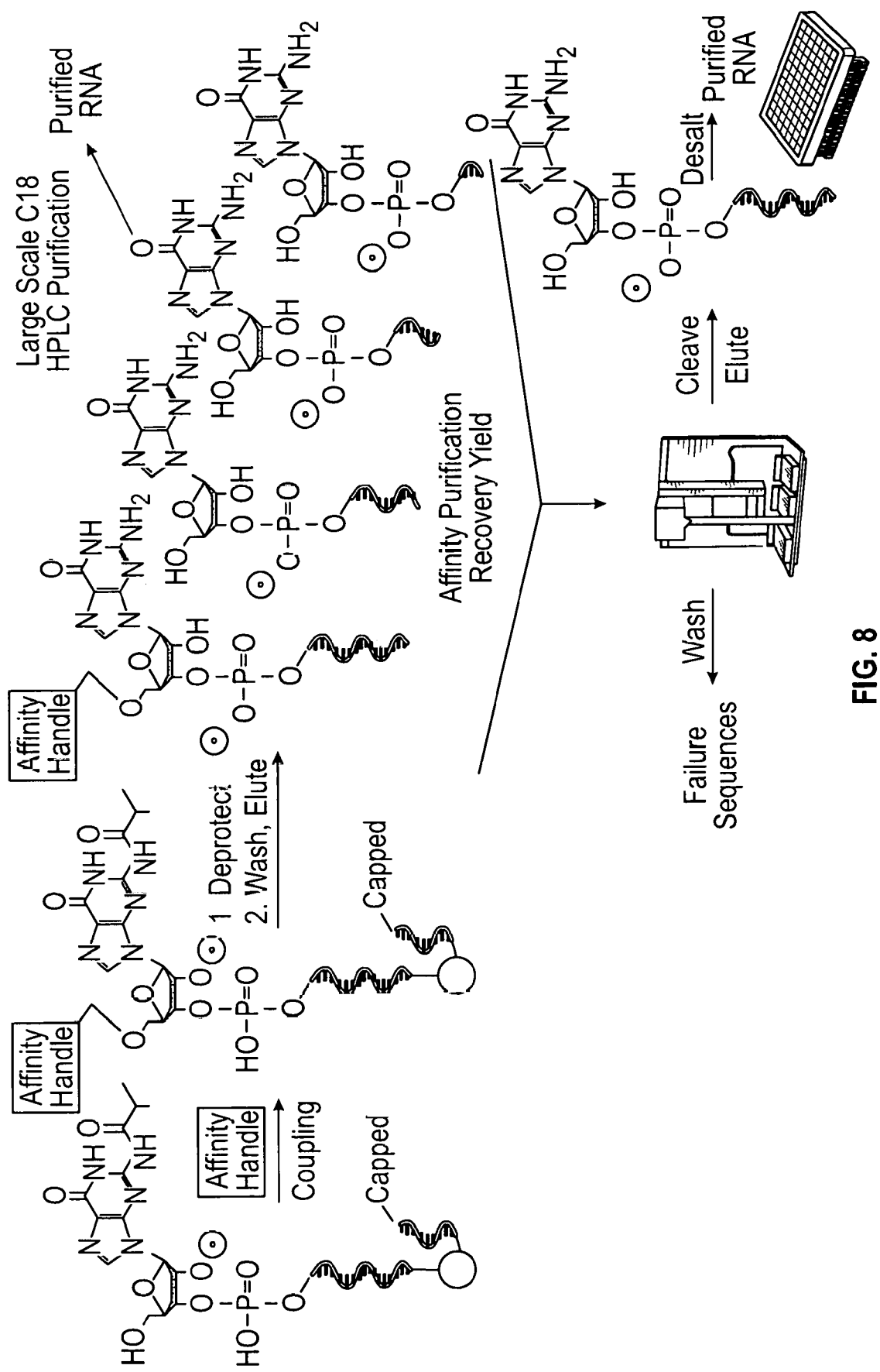
FIG. 8 shows purification strategies using an orthoester protecting group and chromatographic separation for purification of an oligonucleotide.

Referring to FIG. 8, it shows purification strategies using an orthoester protecting group and chromatographic separation for purification of an oligonucleotide-orthoester linker conjugate by using an affinity tag.

As will be apparent to those of skill in the art upon reading this disclosure, each of the individual embodiments described and illustrated herein has discrete components and features which can be readily separated from or combined with the features of any of the other several embodiments without departing from the scope or spirit of the present teachings. Any recited method can be carried out in the order of events recited or in any other order which is logically possible.

Example 1

Synthesis of 2-methoxy-4-(((3,3,4,4,5,5,6,6,7,7,8,8,8-tridecafluorooctyl)oxy)methyl)-1,3-dioxolane. 3-[(3,3,4,4,5,5,6,6,7,7,8,8,8-tridecafluorooctyl)oxy]-1,2-propanediol (1 eq., BOC Sciences) was dissolved in trifluorotoluene (Aldrich) at a concentration of 2 M. Trimethyl orthoformate (3 eq., Aldrich) was dissolve in anhydrous cyclohexane (Aldrich) at a concentration of 3.5 M in a round bottom flask. A catalytic amount of Amberlyst 15 (H form, Aldrich) was added to the flask along with a Teflon coated magnetic stirbar. The trifluorotoluene solution of 3-[(3,3,4,4,5,5,6,6,7,7,8,8,8-tridecafluorooctyl)oxy]-1,2-propanediol was added with stirring and the flask was fitted with a Dean-Stark distillation head. The reaction was slowly heated to reflux and the methanol was removed by azeotropic distillation at a boiling point of 45° C. After 3 hours, the reaction was complete and the flask cooled to room temperature. The Amberlyst resin was removed by filtration and the filtrate concentrated at reduced pressure on a rotary evaporator. The residual was purified by fractional distillation under reduced pressure (b.p.=130-135° C. at 10 mmHg), providing the title compound in 94% isolated yield.

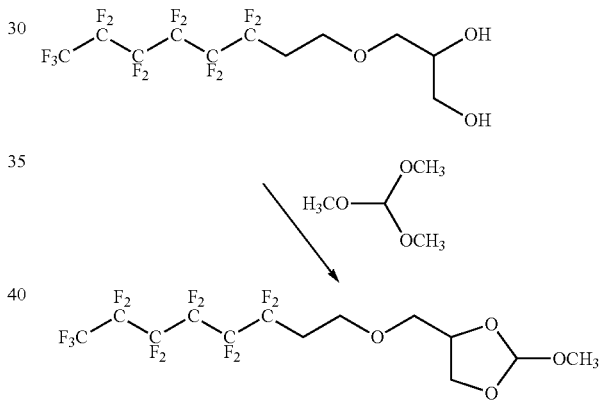

Example 2

4-(((3,3,4,4,5,5,6,6,7,7,8,8,8-tridecafluorooctyl)oxy)methyl)-2-(2,2,2-trifluoroethoxy)-1,3-dioxolane. Tris(2,2,2-trifluoroethyl)orthoformate (50 g, 161 mmol, SynQuest Laboratories) and 3-[(3,3,4,4,5,5,6,6,7,7,8,8,8-tridecafluorooctyl)oxy]-1,2-propanediol (25 g, 57 mmol, Wako Chemicals) was dissolved in 800 mL of anhydrous cyclohexane (Aldrich) in a round bottom flask. Trifluorotoluene (Aldrich) was added in 5 mL portions until the solution was clear (30 mL). A catalytic amount of p-toluenesulfonic acid (Aldrich) was added to the flask along with a Teflon coated magnetic stirbar. The flask was fitted with a Dean-Stark distillation head. The reaction was slowly heated to reflux and the trifluoroethanol was removed by azeotropic distillation at a boiling point of 65° C. After 3 hours, the reaction was complete and the flask was cooled to room temperature. The reaction mixture was concentrated at reduced pressure on a rotary evaporator. The residual was purified by fractional distillation under reduced pressure (b.p.=95-100° C. at 0.05 mmHg), providing the title compound in 74% isolated yield.

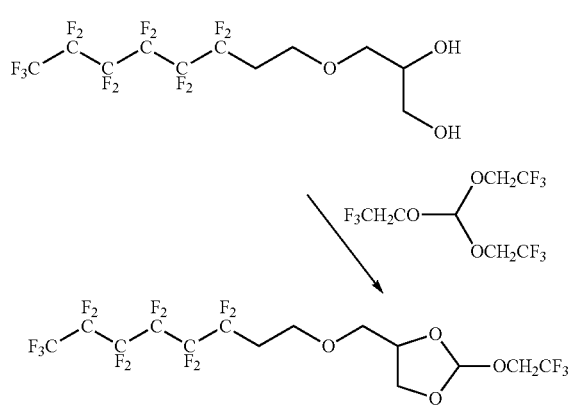

Example 3

Synthesis of 2-methoxy-4-(3,3,4,4,5,5,6,6,7,7,8,8,8-tridecafluorooctyl)-1,3-dioxolane. 5,5,6,6,7,7,8,8,9,9,10,10,10-tridecafluorodecane-1,2-diol (25 g, 61 mmol, 1 eq., Shanghai Chemhere Co., Ltd.) was dissolved in 300 mL of a 90/10 (vol/vol) mixture of cyclohexanes/trifluorotoluene (Aldrich) at a concentration of 2 M. Trimethylorthoformate (9 g, 85 mmol, 1.4 eq., Aldrich) was added to the flask along with a catalytic amount of Amberlyst 15 (H form, Aldrich) and a Teflon coated magnetic stirbar. The flask was fitted with a Dean-Stark distillation head. The reaction was slowly heated to reflux and the methanol was removed by azeotropic distillation at a boiling point of 45° C. After 4 hours, the reaction was deemed complete by the lack of further distillation of methanol azeotrope and the flask was cooled to room temperature. The Amberlyst resin was removed by filtration and the filtrate concentrated at reduced pressure on a rotary evaporator. The residual was purified by fractional distillation under reduced pressure (b.p.=120-130° C. at 10 mmHg), providing the title compound in 64% isolated yield. The product was verified by characteristic peaks in the $^1$H NMR and by molecular ion in ESI/TOF mass spectroscopy (M+1, 451.1 m/z).

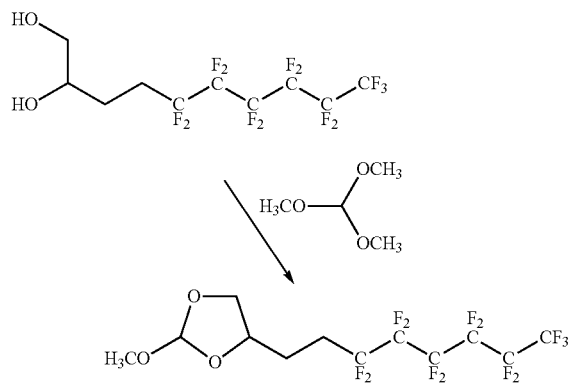

Example 4

Synthesis of 4-(3,3,4,4,5,5,6,6,7,7,8,8,8-tridecafluorooctyl)-2-(2,2,2-trifluoroethoxy)-1,3-dioxolane. Tris(2,2,2-trifluoroethyl)orthoformate (1.4 eq., 48 mmol, 15 g, SynQuest Laboratories) and 5,5,6,6,7,7,8,8,9,9,10,10,10-tridecafluorodecane-1,2-diol (14 g, 34 mmol, 1 eq., Shanghai Chemhere Co., Ltd.) was dissolved in 240 mL of anhydrous cyclohexane (Aldrich) in a round bottom flask. The resulting solution was slightly cloudy and trifluorotoluene (Aldrich) was added dropwise until the solution was clear (5 mL). A catalytic amount of p-toluenesulfonic acid (Aldrich) was added to the flask along with a Teflon coated magnetic stirbar. The flask was fitted with a Dean-Stark distillation head. The reaction was slowly heated to reflux and the trifluoroethanol was removed by azeotropic distillation at a boiling point of 65° C. After 1 hour, the reaction was complete and the flask was cooled to room temperature. The reaction mixture was concentrated at reduced pressure on a rotary evaporator. The residual mixture was purified by fractional distillation under reduced pressure (b.p.=85-104° C. at 0.05 mmHg), providing the title compound in 44% isolated yield. The product was verified by characteristic peaks in the $^1$H NMR and by molecular ion in ESI/TOF mass spectroscopy (M+1, 519.1, 520.1 m/z).

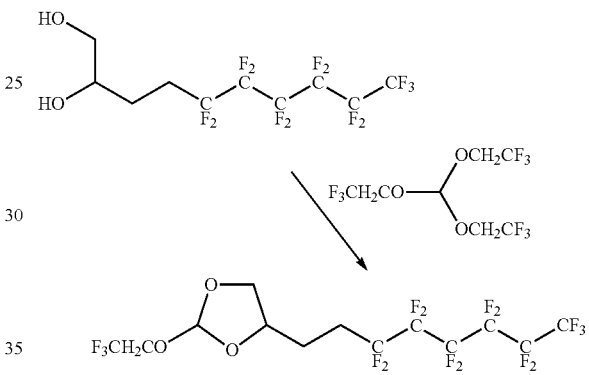

Example 5

Synthesis of 2-methoxy-4-(3,3,4,4,5,5,6,6,6-nonafluorohexyl)-1,3-dioxolane. 5,5,6,6,7,7,8,8,8-nonafluorooctane-1,2-diol (1 eq., 65 mmol, 20 g, Polyorg Inc. (Leominster, Mass.)) was dissolved in 300 mL of cyclohexanes (Aldrich). Trimethylorthoformate (27.5 g, 260 mmol, 4 eq., Aldrich) was added to the flask along with a catalytic amount of Amberlyst 15 (H form, Aldrich) and a Teflon coated magnetic stirbar. The flask was fitted with a Dean-Stark distillation head. The reaction was slowly heated to reflux and the methanol was removed by azeotropic distillation at a boiling point of 45° C. The Amberlyst resin was removed by filtration and the filtrate concentrated at reduced pressure on a rotary evaporator. The residual mixture was purified by fractional distillation under reduced pressure (b.p.=89-105° C. at 10 mmHg), providing the title compound in 32% isolated yield. The product was verified by characteristic peaks in the $^1$H NMR and by molecular ion in ESI/TOF mass spectroscopy (M+1, 35.1 m/z).

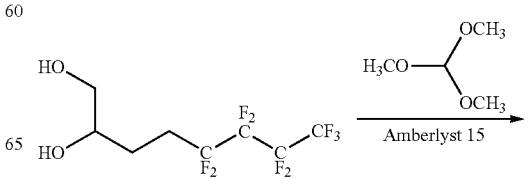

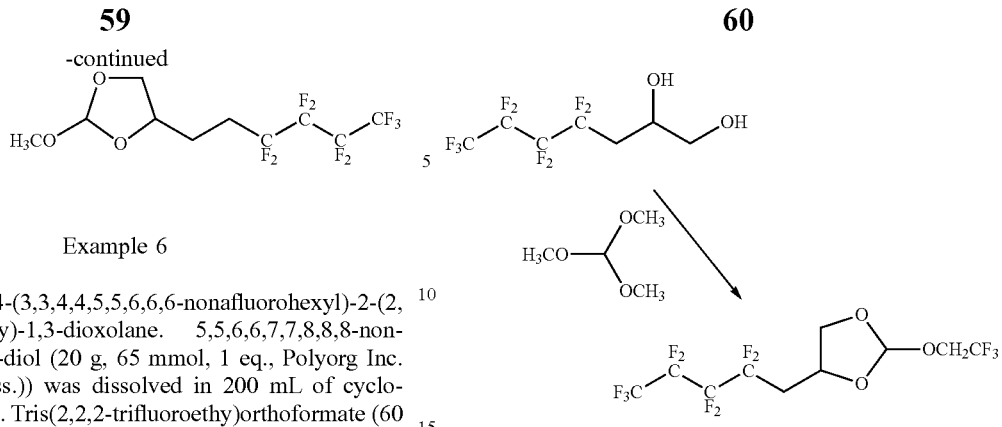

Example 6

Synthesis of 4-(3,3,4,4,5,5,6,6,6-nonafluorohexyl)-2-(2,2,2-trifluoroethoxy)-1,3-dioxolane. 5,5,6,6,7,7,8,8,8-nonafluorooctane-1,2-diol (20 g, 65 mmol, 1 eq., Polyorg Inc. (Leominster, Mass.)) was dissolved in 200 mL of cyclohexanes (Aldrich). Tris(2,2,2-trifluoroethy)orthoformate (60 g, 195 mmol, 3.0 eq., SynQuest Laboratories) was added to the flask along with a catalytic amount of Amberlyst 15 (H form, Aldrich) and a Teflon coated magnetic stirbar. The flask was fitted with a Dean-Stark distillation head. The reaction was slowly heated to reflux and the trifluoroethanol was removed by azeotropic distillation at a boiling point of 65° C. The Amberlyst resin was removed by filtration and the filtrate concentrated at reduced pressure on a rotary evaporator. The residual mixture was purified by fractional distillation under reduced pressure (b.p.=99-116° C. at 0.1 mmHg), providing the title compound in 20% isolated yield. The product was verified by characteristic peaks in the $^1$H NMR and by molecular ion in ESI/TOF mass spectroscopy (M+1, 419.1 m/z)

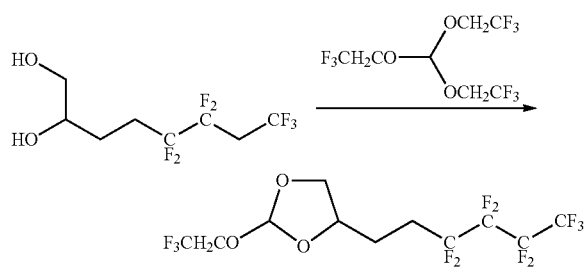

Example 7

Synthesis of 4-(2,2,3,3,4,4,5,5,5-nonafluoropentyl)-2-(2,2,2-trifluoroethoxy)-1,3-dioxolane. 1H, 1H, 2H, 3H, 3H-perfluoroheptane-1,2-diol (25 g, 85 mmol, 1 eq., SynQuest Laboratories, Inc. (Alachua, Fla.)) was dissolved in 250 mL of cyclohexanes (Aldrich). Trimethylorthoformate (18 g, 170 mmol, 2.0 eq., Aldrich) was added to the flask along with a catalytic amount of Amberlyst 15 (H form, Aldrich) and a Teflon coated magnetic stirbar. The flask was fitted with a Dean-Stark distillation head. The reaction was slowly heated to reflux and the methanol was removed by azeotropic distillation at a boiling point of 65° C. After 4 hours, the reaction was deemed complete by the lack of further distillation of trifluoroethanol azeotrope and the flask cooled to room temperature. The Amberlyst resin was removed by filtration and the filtrate concentrated at reduced pressure on a rotary evaporator. The residual mixture was purified by fractional distillation under reduced pressure (b.p.=105-110° C. at 10 mmHg), providing the title compound in 39% isolated yield. The product was verified by characteristic peaks in the $^1$H NMR and by molecular ion in ESI/TOF mass spectroscopy (M+1, 405.0 m/z).

Example 8

Synthesis of 4,5-bis(((3,3,4,4,5,5,5-heptafluoropentyl)oxy)methyl)-2-methoxy-1,3-dioxolane. (5-Hydroxymethyl-2,2-dimethyl-[1,3]dioxolan-4-yl)-methanol (10 g, 62 mmol, Combi-Blocks, Inc. (San Diego, Calif.)) was dissolved in 200 mL of anhydrous tetrahydrofuran. Sodium hydride (10 g, Aldrich, 95%) was added to the flask and the mixture was heated to reflux for 30 minutes then allowed to cool to room temperature. 1,1,1,2,2,3,3-Heptafluoro-5-iodopentane (42.7 g, 124 mmol, Oakwood Chemical (Estill, S.C.)) was added to the flask and the reaction heated to reflux for 2 hours. The reaction was cooled to room temperature the excess base was neutralized by the addition of ammonium chloride and the solvent evaporated under reduced pressure on a rotary evaporator. The crude mixture was dissolved in dichloromethane and extracted with sodium bicarbonate, followed by water and brine. The dichloromethane solution was dried over sodium sulfate and the product purified from the starting material on silica gel using ethyl acetate and hexanes. The product fractions were evaporated in a tared flask giving 20.6 g of a yellow viscous oil (≅60% yield). The oil was dissolved in 200 mL of methanol and cooled to 0° C. in an ice/water bath. Concentrated $H_2SO_4$ was added dropwise with stirring until the final concentration was 9% and the reaction was stirred for 2 hours. The reaction was allowed to warm to room temperature and triethylamine was added to neutralize the acid using pH paper as an indicator. The methanol was evaporated to dryness and the product purified on silica gel using ethyl acetate and hexanes, yielding 13.6 g of purified 1,4-bis((3,3,4,4,5,5,5-heptafluoropentyl)oxy)-butane-2,3-diol.

1,4-bis((3,3,4,4,5,5,5-heptafluoropentyl)oxy)butane-2,3-diol (26.5 mmol, 13.6 g) was dissolved in 150 mL of cyclohexanes (Aldrich). Trimethylorthoformate (5.6 g, 53 mmol, Aldrich) was added to the flask along with a catalytic amount of Amberlyst 15 (H form, Aldrich) and a Teflon coated magnetic stirbar. The flask was fitted with a Dean-Stark distillation head. The reaction was slowly heated to reflux and the methanol was removed by azeotropic distillation at a boiling point of 45° C. After 4 hours, the reaction was deemed complete by the lack of further distillation of methanol azeotrope and the flask cooled to room temperature. The Amberlyst resin was removed by filtration and the filtrate concentrated at reduced pressure on a rotary evaporator. The residual mixture was purified by fractional distillation under reduced pressure (b.p.=185-190° C. at 10 mmHg), providing the title compound in 61% isolated yield.

The product was verified by characteristic peaks in the $^1$H NMR and by molecular ion in ESI/TOF mass spectroscopy (M+1, 557.2 m/z).

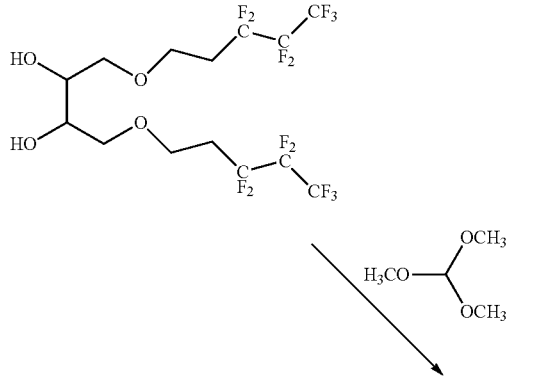

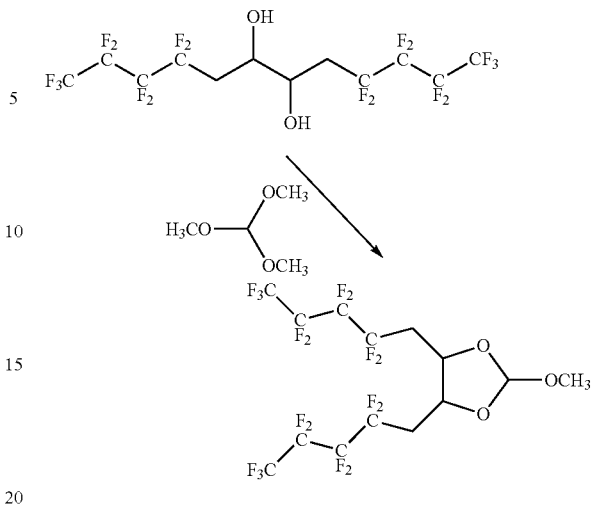

Example 9

Synthesis of 2-methoxy-4,5-bis(2,2,3,3,4,4,4,5,5,5-nonafluoropentyl)-1,3-dioxolane. 1,1,1,2,2,3,3,4,4,9,9,10,10,11,11,12,12,12-Octadecafluoro-6,7-dodecanediol was prepared by the method described by Laurent, P. et al (Journal of Fluorine Chemistry, 62(2-3), 161-71; 1993). The diol (12 g, 22.8 mmol) was dissolved in 120 mL of cyclohexanes (Aldrich). Trimethylorthoformate (4.8 g, 45.6 mmol, 2.0 eq., Aldrich) was added to the flask along with a catalytic amount of Amberlyst 15 (H form, Aldrich) and a Teflon coated magnetic stirbar. The flask was fitted with a Dean-Stark distillation head. The reaction was slowly heated to reflux and the methanol was removed by azeotropic distillation at a boiling point of 45° C. After 4 hours, the reaction was deemed complete by the lack of further distillation of methanol azeotrope and the flask cooled to room temperature. The Amberlyst resin was removed by filtration and the filtrate concentrated at reduced pressure on a rotary evaporator. The residual mixture was purified by fractional distillation under reduced pressure (b.p.=162-173° C. at 10 mmHg), providing the title compound in 52% isolated yield. The product was verified by characteristic peaks in the $^1$H NMR and by molecular ion in ESI/TOF mass spectroscopy (M+1, 569.1 m/z).

Example 10

Synthesis of 4,4,5,5,6,6,7,7,8,8,9,9,10,10,11,11,11-heptadecafluoro-N-((2-methoxy-1,3-dioxolan-4-yl)methyl)undecanamide. N-(2,3-dihydroxypropyl)-4,4,5,5,6,6,7,7,8,8,9,9,10,10,11,11,11-heptadecafluoroundecanamide was prepared by reaction of 3-aminopropane-1,2-diol (Aldrich), with the nitrophenyl ester of heptadecafluoroundecanoic acid (SynQuest Laboratories, Inc., Alachua, Fla.).

Heptadecafluoroundecanoic acid (10.0 g, 20.3 mmol), p-nitrophenol (2.8 g, 20.3 mmol), N,N'-dicyclohexylcarbodiimide (4.2 g, 20.3 mmol), N,N-dimethylpyridin-4-amine (250 mg) was dissolved in 350 mL of anhydrous dioxane. The reaction was stirred overnight at room temperature, and then evaporated to form an oil. The product was purified by silica gel column chromatography eluting with a gradient of hexane:ethyl acetate (starting at 9:1). The product, 4-nitrophenyl 4, 4, 5, 5, 6, 6, 7, 7, 8, 8, 9, 9, 10, 10, 11, 11, 11-heptadecafluoro-undecanoate, was isolated with 90+% yield.

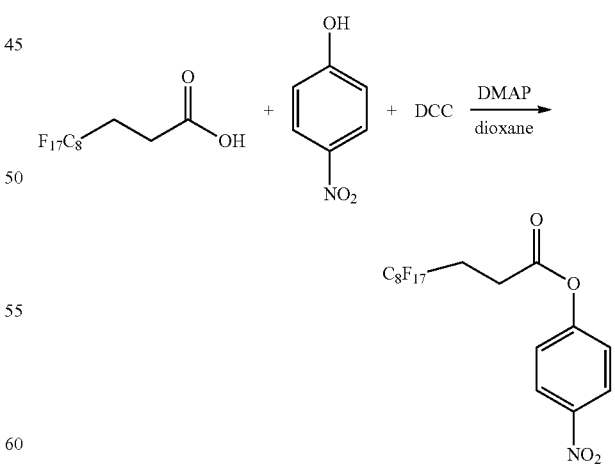

4-Nitrophenyl 4,4,5,5,6,6,7,7,8,8,9,9,10,10,11,11,11-heptadecafluoroundecanoate (10 g, 16.3 mmol), 3-aminopropane-1,2-diol (1.4 g, 16.3 mmol), triethylamine (1.7 g, 16.3 mmol) was dissolved in a mixture of 200 mL dichloromethane and 80 mL of N,N-dimethyl-formamide. The reaction was stirred for 3 hours at room temperature. The reaction mixture was purified by silica gel column chromatography using methylene chloride, generating the product in 87% isolated yield.

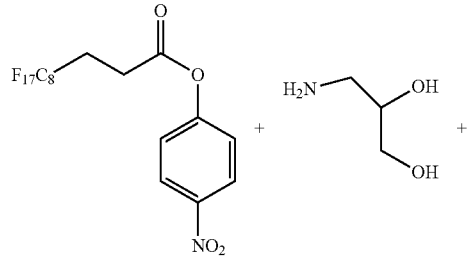

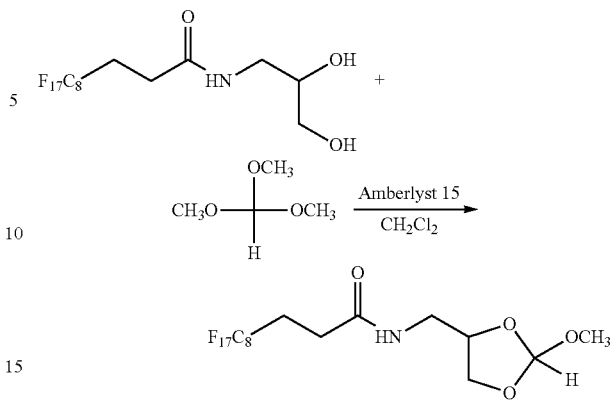

N-(2,3-dihydroxypropyl)-4,4,5,5,6,6,7,7,8,8,9,9,10,10,11,11,11-heptadecafluoroundecanamide (8.6 g, 15.2 mmol) was dissolved in 100 mL of cyclohexanes (Aldrich). Trimethylorthoformate (3.2 g, 30.4 mmol, 2.0 eq., Aldrich) was added to the flask along with a catalytic amount of Amberlyst 15 (H form, Aldrich) and a Teflon coated magnetic stirbar. The flask was fitted with a Dean-Stark distillation head. The reaction was slowly heated to reflux and the methanol was removed by azeotropic distillation at a boiling point of 45° C. After 4 hours, the reaction was deemed complete by the lack of further distillation of methanol azeotrope and the flask cooled to room temperature. The Amberlyst resin was removed by filtration and the filtrate concentrated at reduced pressure on a rotary evaporator. The residual mixture was purified by silica gel column chromatography using dichloromethane and triethylamine, providing the title compound in 60% isolated yield. The product was verified by characteristic peaks in the $^1$H NMR and by molecular ion in ESI/TOF mass spectroscopy (M+1, 608.0 m/z).

Example 11

Synthesis of 4,4,5,5,6,6,7,7,8,8,9,9,9-tridecafluoro-N-((2-methoxy-1,3-dioxolan-4-yl)methyl)nonanamide. N-(2,3-dihydroxypropyl)-4,4,5,5,6,6,7,7,8,8,9,9,9-tridecafluorononanamide was prepared by reaction of 3-aminopropane-1,2-diol (Aldrich), with the nitrophenyl ester of 3-(perfluorohexyl)propionic acid (SynQuest Laboratories, Inc., Alachua, Fla.) as described for EXAMPLE 10.

N-(2,3-dihydroxypropyl)-4,4,5,5,6,6,7,7,8,8,9,9,9-tridecafluorononanamide, 10.0 g, 21.5 mmol, was dissolved in 120 mL of cyclohexanes (Aldrich). Trimethylorthoformate (4.6 g, 43.0 mmol, 2.0 eq, Aldrich) was added to the flask along with a catalytic amount of Amberlyst 15 (H form, Aldrich) and a Teflon coated magnetic stirbar. The flask was fitted with a Dean-Stark Distillation Head. The reaction was slowly heated to reflux and the methanol was removed by azeotropic distillation at a boiling point of 45° C. After 4 hours, the reaction was deemed complete by the lack of further distillation of methanol azeotrope and the flask cooled to room temperature. The Amberlyst resin was removed by filtration and the filtrate concentrated at reduced pressure on a rotary evaporator. The residual was purified by silica gel column chromatography using dichloromethane and triethylamine, providing the title compound in 71% yield. The product was verified by characteristic peaks in the $^1$H NMR and by molecular ion in ESI/TOF mass spectroscopy (M+1, 508.1 m/z).

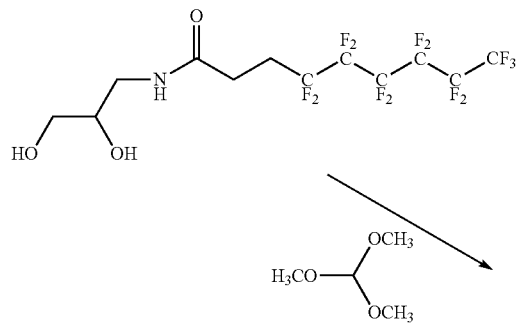

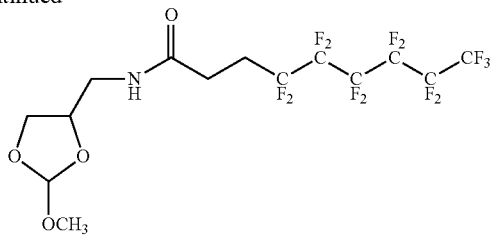

Example 12

Synthesis of 4,4,5,5,6,6,6-heptafluoro-N-((2-methoxy-1,3-dioxolan-4-yl)methyl)hexanamide. N-(2,3-dihydroxypropyl)-4,4,5,5,6,6,6-heptafluorohexanamide was prepared by reaction of 3-aminopropane-1,2-diol (Aldrich), with the nitrophenyl ester of 2H, 2H, 3H, 3H-perfluorohexanoic acid (SynQuest Laboratories, Inc., Alachua, Fla.) as described for EXAMPLE 10.

N-(2,3-dihydroxypropyl)-4,4,5,5,6,6,6-heptafluorohexanamide (10.0 g, 31.7 mmol) was dissolved in 160 mL of cyclohexanes (Aldrich). Trimethylorthoformate (6.7 g, 63.4 mmol, 2.0 eq, Aldrich) was added to the flask along with a catalytic amount of Amberlyst 15 (H form, Aldrich) and a Teflon coated magnetic stirbar. The flask was fitted with a Dean-Stark distillation head. The reaction was slowly heated to reflux and the methanol was removed by azeotropic distillation at a boiling point of 45° C. After 4 hours, the reaction was deemed complete by the lack of further distillation of methanol azeotrope and the flask cooled to room temperature. The Amberlyst resin was removed by filtration and the filtrate concentrated at reduced pressure on a rotary evaporator. The residual mixture was purified by silica gel column chromatography using dichloromethane and triethylamine, providing the title compound in 55% isolated yield. The product was verified by characteristic peaks in the $^1$H NMR and by molecular ion in ESI/TOF mass spectroscopy (M+1, 358.1 m/z).

Example 13

Synthesis of N-((2-methoxy-1,3-dioxolan-4-yl)methyl)-3-(perfluorophenyl)propenamide. N-(2,3-dihydroxypropyl)-3-(perfluorophenyl)propanamide was prepared by reaction of 3-aminopropane-1,2-diol (Aldrich) with the nitrophenyl ester of 3-(Pentafluorophenyl)propionic acid (SynQuest Laboratories, Inc., Alachua, Fla.) as described for EXAMPLE 10.

N-(2,3-dihydroxypropyl)-3-(perfluorophenyl)propanamide (10.0 g, 32.0 mmol) was dissolved in 160 mL of cyclohexanes (Aldrich). Trimethylorthoformate (6.8 g, 64.0 mmol, 2.0 eq., Aldrich) was added to the flask along with a catalytic amount of Amberlyst 15 (H form, Aldrich) and a Teflon coated magnetic stirbar. The flask was fitted with a Dean-Stark Distillation Head. The reaction was slowly heated to reflux and the methanol was removed by azeotropic distillation at a boiling point of 45° C. After 4 hours, the reaction was deemed complete by the lack of further distillation of methanol azeotrope and the flask cooled to room temperature. The Amberlyst resin was removed by filtration and the filtrate concentrated at reduced pressure on a rotary evaporator. The residual was purified by silica gel column chromatography using dichloromethane and triethylamine, providing the title compound in 78% isolated yield. The product was verified by characteristic peaks in the $^1$H NMR and by molecular ion in ESI/TOF mass spectroscopy (M+1, 355.1 m/z).

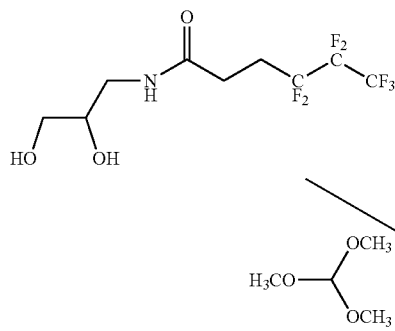

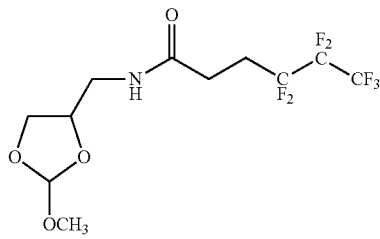

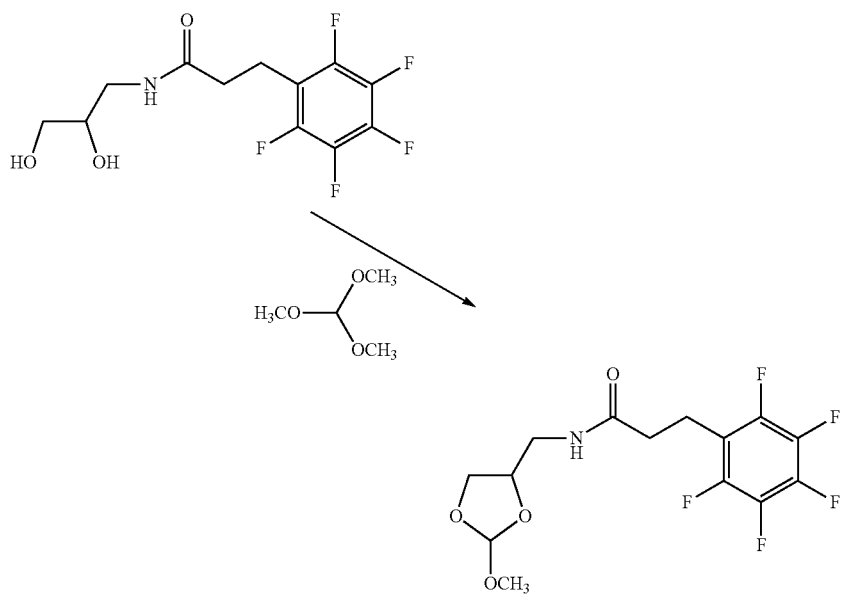

Example 14

Synthesis of N,N'-((2-methoxy-1,3-dioxolane-4,5-diyl)bis(methylene))bis(3-(perfluorophenyl)propanamide). N,N'-(2,3-dihydroxybutane-1,4-diyl)bis(3-(perfluorophenyl)propanamide) was prepared by reaction of 1,4-diaminobutane-2,3-diol (Chemspace, Riga, Latvia) with the nitrophenyl ester of 3-(Pentafluoro acid (SynQuest Laboratories, Inc., Alachua, Fla.).

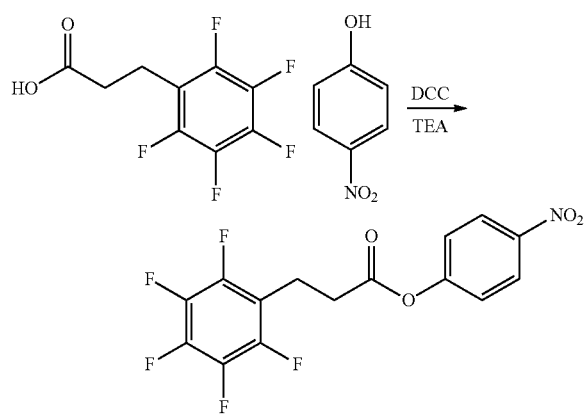

4-nitrophenyl 3-(perfluorophenyl)propanoate (20 g, 55.4 mmol), 1,4-diaminobutane-2,3-diol (3.3 g, 27.7 mmol) and triethylamine (5.6 g, 55.4 mmol) was dissolved in a mixture of 250 mL dichloromethane and 100 mL N,N-dimethylformamide. The reaction was stirred for 3 hours at room temperature. The reaction mixture was purified by silica gel column chromatography in methylene chloride, giving the product in 82% isolated yield.

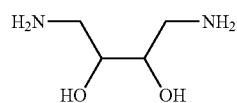

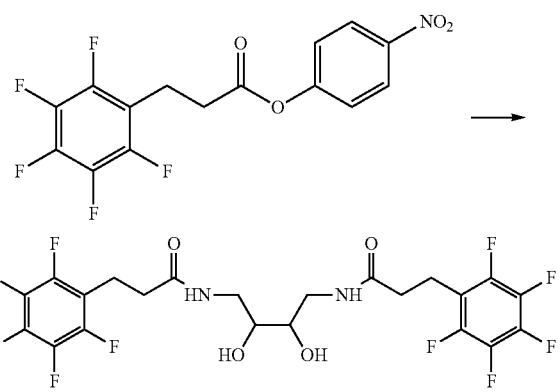

N,N'-(2,3-dihydroxybutane-1,4-diyl)bis(3-(perfluorophenyl)propanamide) (10.0 g, 17.7 mmol) was dissolved in 100 mL of cyclohexanes (Aldrich), resulting in a cloudy solution which was then clarified by dropwise addition of trifluorotoluene (Aldrich). Trimethylorthoformate (3.8 g, 35.4 mmol, 2.0 eq., Aldrich) was added to the flask along with a catalytic amount of Amberlyst 15 (H form, Aldrich) and a Teflon coated magnetic stirbar. The flask was fitted with a Dean-Stark distillation head. The reaction was slowly heated to reflux and the methanol was removed by azeotropic distillation at a boiling point of 45° C. After 4 hours, the reaction was deemed complete by the lack of further distillation of methanol azeotrope and the flask cooled to room temperature. The Amberlyst resin was removed by filtration and the filtrate concentrated at reduced pressure on a rotary evaporator. The residual mixture was purified by silica gel column chromatography using dichloromethane and triethylamine, providing the title compound in 41% isolated yield. The product was verified by characteristic peaks in the $^1$H NMR and by molecular ion in ESI/TOF mass spectroscopy (M+1, 607.2 m/z).

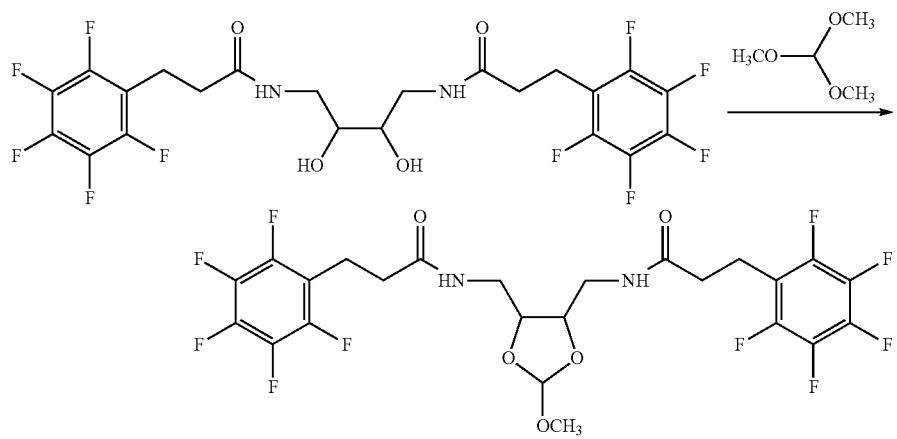

Example 15

Synthesis of N,N'-((2-methoxy-1,3-dioxolane-4,5-diyl)bis(methylene))-bis(4,4,5,5,6,6,7,7,7-nonafluoro-heptanamide). N,N'-(2,3-dihydroxybutane-1,4-diyl)bis(4,4,5,5,6,6,7,7,7-nonafluoroheptanamide), was prepared by reaction of 1,4-diaminobutane-2,3-diol (Chemspace, Riga, Latvia), with the nitrophenyl ester of 4,4,5,5,6,6,7,7,7-Nonafluoroheptanoic acid (SynQuest Laboratories, Inc., Alachua, Fla.) using reaction conditions as described for EXAMPLE 14.

N,N'-(2,3-dihydroxybutane-1,4-diyl)bis(4,4,5,5,6,6,7,7,7-nonafluoroheptanamide) (10.0 g, 15.0 mmol) was dissolved in 100 mL of cyclohexanes (Aldrich). The solution was clarified by dropwise addition of trifluorotoluene (Aldrich). Trimethylorthoformate (3.2 g, 30.0 mmol, 2.0 eq, Aldrich) was added to the flask along with a catalytic amount of Amberlyst 15 (H form, Aldrich) and a Teflon coated magnetic stirbar. The flask was fitted with a Dean-Stark distillation head. The reaction was slowly heated to reflux and the methanol was removed by azeotropic distillation at a boiling point of 45° C. After 4 hours, the reaction was deemed complete by the lack of further distillation of methanol azeotrope and the flask cooled to room temperature. The Amberlyst resin was removed by filtration and the filtrate concentrated at reduced pressure on a rotary evaporator. The residual mixture was purified by silica gel column chromatography using dichloromethane and triethylamine, providing the title compound in 64% isolated yield. The product was verified by characteristic peaks in the $^1$H NMR and by molecular ion in ESI/TOF mass spectroscopy (M+1, 711.1 m/z).

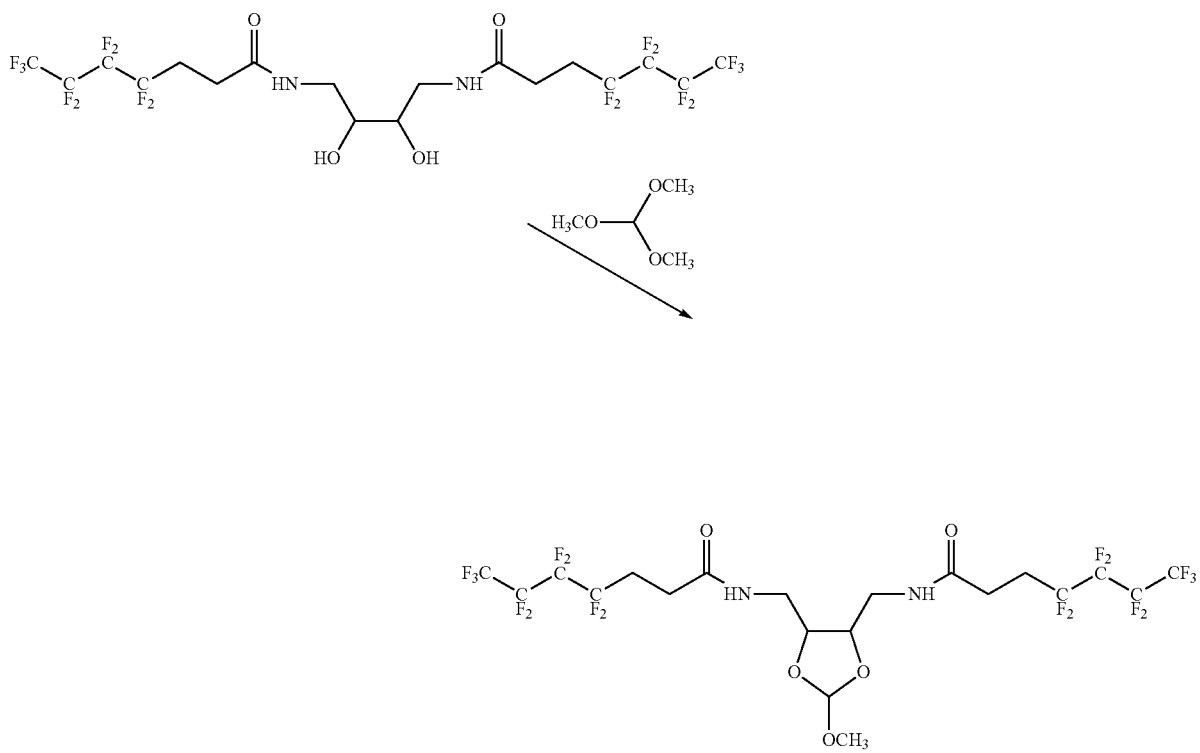

Example 16

Synthesis of 4-(chloromethyl)-2-methoxy-1,3-dioxolane. 4-(chloromethyl)-2-methoxy-1,3-dioxolane was prepared in 94% isolated yield by the method described by Nguyen-Ba N. et al (Anti-viral compounds, U.S. Pat. No. 5,789,394A, Aug. 4, 1998).

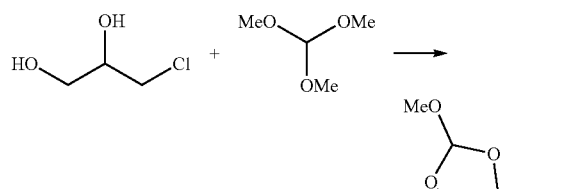

Example 17

Synthesis of S-((2-methoxy-1,3-dioxolan-4-yl)methyl) ethanethioate. S-(2,3-dihydroxypropyl) ethanethioate was prepared by the method described by Polster J. et al (J. Agric. Food Chem., 63, 1419-1432; 2015). The diol (10.21 g, 68 mmol) was dissolved in cyclohexane (Aldrich) at a concentration of 0.7 M in a round bottom flask containing a Teflon coated magnetic stirbar. Trimethyl orthoformate (1.5 eq, Aldrich) and a catalytic amount of p-toluenesulfonic acid (5 mol %, Aldrich) were added to the round bottom flask and the flask was fitted with a Dean-Stark distillation head. The reaction was slowly heated to reflux and the methanol was removed by azeotropic distillation at a boiling point of 45° C. After 2 hours, the reaction was complete and the flask cooled to room temperature, followed by concentration at reduced pressure on a rotary evaporator. The product was purified by silica gel column chromatography (conditioned with 1% triethylamine in 9:1 hexanes:ethyl acetate), eluting with a gradient of hexane:ethyl acetate (started from 9:1 hexanes:ethyl acetate). The title compound was isolated in 72% yield. The product was verified by characteristic peaks in the $^1$H and $^{13}$C NMR and by molecular ion in positive mode ESI/TOF mass spectroscopy ([M-OMe]$^+$, 161.0 m/z).

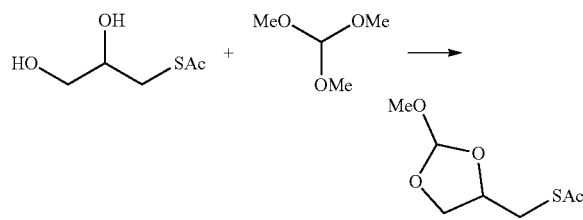

Example 18

Synthesis of 1,2-bis((2-methoxy-1,3-dioxolan-4-yl) methyl)disulfane. (2-methoxy-1,3-dioxolan-4-yl)methanethiol was prepared by the method described by Polster J. et al (J. Agric. Food Chem., 63, 1419-1432; 2015). The thiol (3.00 g, 20 mmol) was dissolved in EtOAc (Aldrich) at a concentration of 0.33 M in a round bottom flask containing a Teflon coated magnetic stirbar. To the solution was added NaI (54 mg, 0.36 mmol, Aldrich) and 30% $H_2O_2$ (4.0 mL, 36 mmol, Aldrich) and the mixture was stirred at 23° C. for 0.5 hours. The reaction was quenched by the addition of 100 mL saturated aqueous sodium thiosulfate. The mixture was extracted with three 150 mL portions of ethyl acetate (Aldrich). The combined organic extracts were washed with a 150 mL portion of saturated sodium chloride, dried over magnesium sulfate (Aldrich), and concentrated at reduced pressure on a rotary evaporator. The crude residue was purified by silica gel chromatography by eluting with a gradient of hexane:ethyl acetate (starting from 9:1). The title compound was isolated in 78% yield. The product was verified by characteristic peaks in the 1H and 13C NMR and by molecular ion in positive mode ESI/TOF mass spectroscopy ([M-OMe]$^+$, 267.0 m/z).

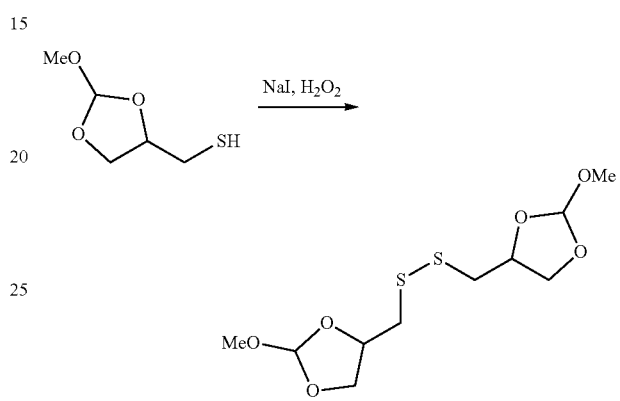

Example 19

Synthesis of 2-methoxy-4-((phenyldisulfanyl)methyl)-1,3-dioxolane. 3-(phenyldisulfanyl)propane-1,2-diol was prepared by the method described by Hunter R. et al (Journal of Organic Chemistry, 71, 8268-8271; 2006). The diol (102 mg, 0.47 mmol) was dissolved in cyclohexane (Aldrich) at a concentration of 0.1M in a round bottom flask containing a Teflon coated magnetic stirbar. Trimethyl orthoformate (1.5 eq, Aldrich) and p-toluenesulfonic acid (Aldrich) were added to the round bottom flask and the flask was fitted with a Dean-Stark distillation head. The reaction was slowly heated to reflux and the methanol was removed by azeotropic distillation at a boiling point of 45° C. After 3 hours, the reaction was complete and the flask cooled to room temperature, followed by concentration at reduced pressure on a rotary evaporator. The product was purified by silica gel column chromatography, eluting with a gradient of hexane: ethyl acetate (starting from hexane). The title compound was isolated in 68% yield. The product was verified by characteristic peaks in the 1H and 13C NMR and by molecular ion in positive mode ESI/TOF mass spectroscopy ([M-OMe]$^+$, 227.0 m/z).

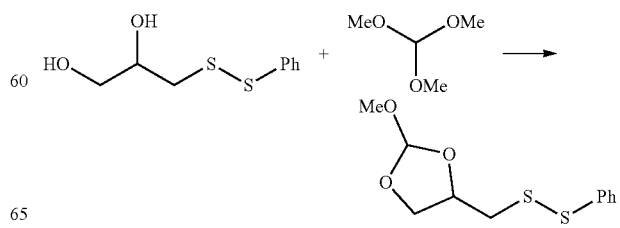

Example 20

Synthesis of 1-((2-methoxy-1,3-dioxolan-4-yl)methyl)-1H-pyrrole. 3-(1H-pyrrol-1-yl)propane-1,2-diol (5.0 g, 35.4 mmol, Aurum Pharmatech) was dissolved in cyclohexane (Aldrich) at a concentration of 0.2M in a round bottom flask containing a Teflon coated magnetic stirbar. Trimethyl orthoformate (1.5 eq, Aldrich) and a catalytic amount of p-toluenesulfonic acid (5 mol %, Aldrich) were added to the round bottom flask and the flask was fitted with a Dean-Stark distillation head. The reaction was slowly heated to reflux and the methanol was removed by azeotropic distillation at a boiling point of 45° C. After 3 hours, the reaction was complete and the flask cooled to room temperature, followed by concentration at reduced pressure on a rotary evaporator. The product was purified by silica gel column chromatography, eluting with a gradient of hexane:ethyl acetate (starting from pure hexane). The title compound was isolated in 66% yield. The product was verified by characteristic peaks in the $^1$H and $^{13}$C NMR and by molecular ion in positive mode ESI/TOF mass spectroscopy ([M+H], 183.1 m/z.

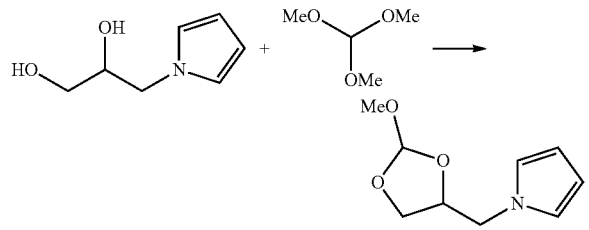

Example 21

Synthesis of 1-((2R,4S,5R)-4-hydroxy-5-((((4-((((2-methoxy-1,3-dioxolan-4-yl)methyl)disulfanyl)methyl)-1,3-dioxolan-2-yl)oxy)methyl)tetrahydrofuran-2-yl)-5-methylpyrimidine-2,4(1H,3H)-dione. 20 mg 3'-dT-CPG (Glen Research) was treated with 100 μL 3% trichloroacetic acid in dichloromethane (Glen Research) twice for 1 min, followed by 5 mL acetonitrile, and was dried with a stream of nitrogen. 1,2-bis((2-methoxy-1,3-dioxolan-4-yl)methyl)disulfane orthoester (45 μL), acetonitrile (45 μL, Aldrich), and 3% trichloroacetic acid in dichloromethane (10 μL, Glen Research) were added to the 3'-dT-CPG. The mixture was heated at 60° C. for 1 hr. After removal of residual liquid, the CPG was washed with 8 mL acetonitrile, followed by drying with a stream of nitrogen. The 3'-dT-CPG-orthoester conjugate was treated with concentrated 28% ammonium hydroxide (100 μL) at 23° C. for 2 hours. The resulting filtrate was concentrated under reduced pressure on a Savant speedvac, dissolved in 500p water, and analyzed by ESI/TOF mass spectrometry ([M-OMe]$^+$, 477.1 m/z).

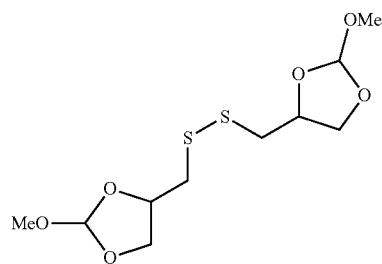

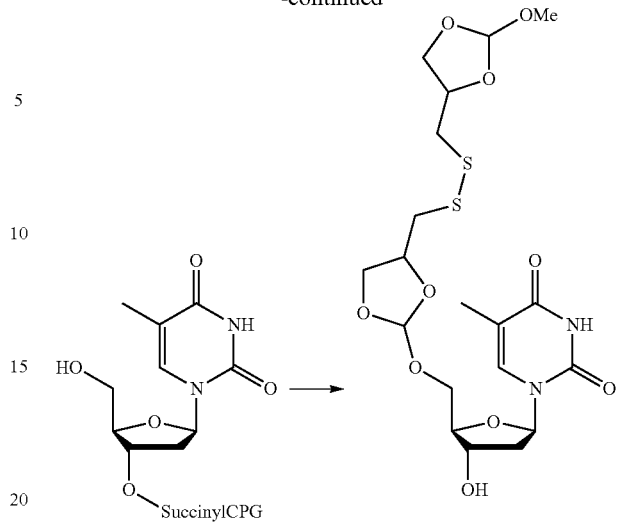

Example 22

1,2-bis((2-methoxy-1,3-dioxolan-4-yl)methyl)disulfane: dT conjugate, Sulfolink capture, and release. 30 mg 3'-dT-CPG (Glen Research) was treated with 100 μL of 3% trichloroacetic acid in dichloromethane (Glen Research) twice for 1 min, followed by 5 mL acetonitrile, and was dried with a stream of nitrogen. 1,2-bis((2-methoxy-1,3-dioxolan-4-yl)methyl)disulfane orthoester (45 μL), acetonitrile (45 μL, Aldrich), and 3% trichloroacetic acid in dichloromethane (10 μL, Glen Research) were added to the 3'-dT-CPG. The mixture was heated at 60° C. for 1 hour. After removal of residual liquid, the CPG was washed with 8 mL acetonitrile, followed by drying with a stream of nitrogen. The dT-CPG: orthoester conjugate was treated with 50 mM TCEP (200 μL, Aldrich) solution, prepared in ammonium bicarbonate (200 mM), pH 8.0, for 1 hour at 23° C. The reduced thiol containing conjugate was deprotected and released from the CPG by treatment with concentrated ammonium hydroxide (100 μL, Aldrich) for 1 hour at 23° C. Following concentration of the filtrate in a Savant speedvac for 1 hour, the residue was dissolved in 200 μL 50 mM Tris.HCl, 5 mM EDTA, pH 8.5. This solution was incubated with 300 μL Sulfolink resin (ThermoFisher) for 12 hours at 23° C. The resin was washed with 200 μL 50 mM Tris.HCl, 5 mM EDTA, pH 8.5, followed by 8 mL acetonitrile. The product 3'-dT was release from the resin by incubating with 100 μL 20% v/v aqueous formic acid at 23° C. for 60 minutes. The resulting filtrate was concentrated on a Savant speedvac and analyzed by ESI/TOF mass spectrometry (M+H, m/z 243.1).

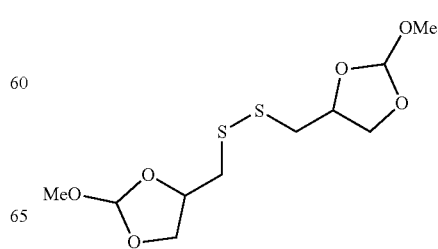

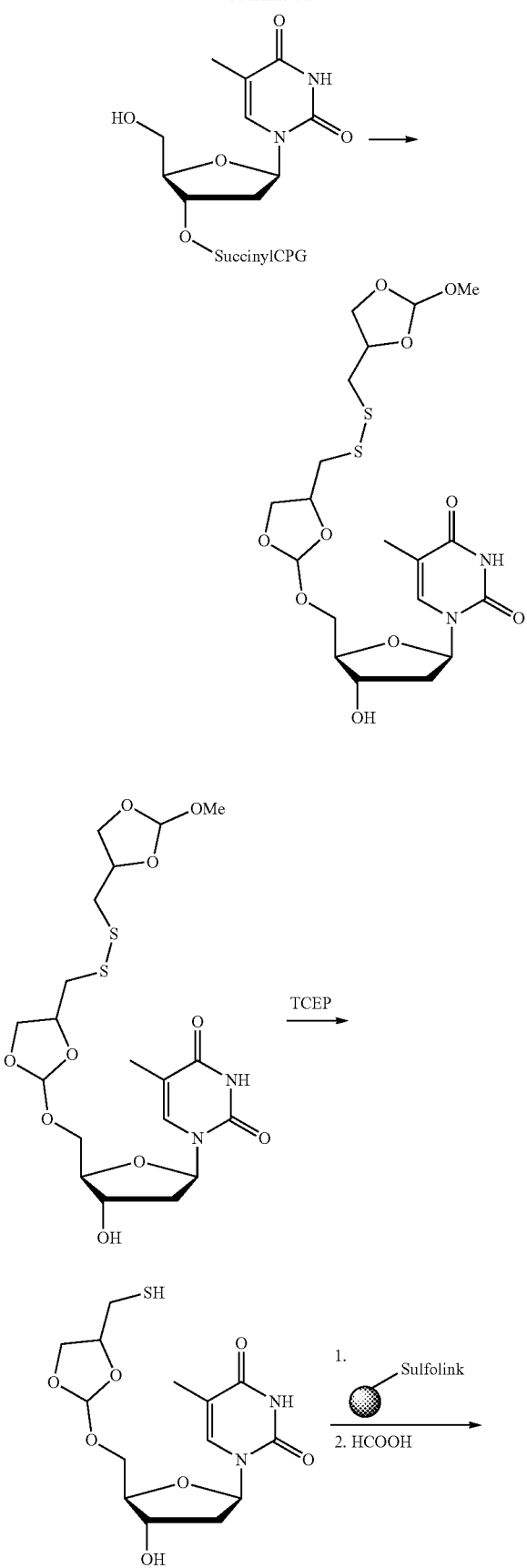

Example 23

1-((2-methoxy-1,3-dioxolan-4-yl)methyl)-1H-pyrrole: PTAD:RNA conjugate. 10 mg of 20mer RNA-CPG was treated with 100 µL 3% trichloroacetic acid in dichloromethane (Glen Research) twice for 1 min, followed by 5 mL acetonitrile, and was dried with a stream of nitrogen. 45 µL of 1-((2-methoxy-1,3-dioxolan-4-yl)methyl)-1H-pyrrole and 5 µL of 3% trichloroacetic acid in dichloromethane (Glen Research) were added to the 20mer RNA CPG, and the mixture was heated at 70° C. for 2 hours. After removal of residual liquid, the CPG was washed with 8 mL acetonitrile, followed by drying with a stream of nitrogen. The dried CPG was treated with 100 µL 0.2 M 4-phenyl-1,2,4-triazole-3,5-dione (PTAD)(Aldrich) in acetonitrile for 30 seconds. The PTAD solution was removed and the CPG was washed with 8 mL dry ACN and dried under a stream of nitrogen. The 20mer RNA-CPG-orthoester-PTAD conjugate was treated with neat ethylenediamine at 23° C. for 2 hours, followed by rinsing of the CPG with 3 mL dry acetonitrile. The cleaved 20mer RNA:orthoester:PTAD conjugate was eluted with 0.3 mL 0.1 M ammonium acetate buffer (pH=6.9), and analyzed by deconvoluted ESI/TOF mass spectrometry (M=6763.86 m/z), showing addition of one pyrrolo orthoester and two PTAD molecules.

77
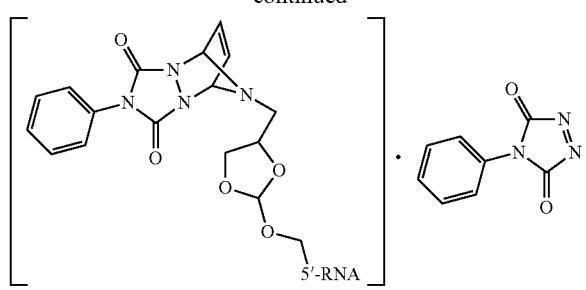
Example 24
General Procedures for the Attachment of 1,3-Dioxalane and 1,4-Dioxalane Orthoester Linkers to Nascently Synthesized Oligonucleotides on Solid Support.
78
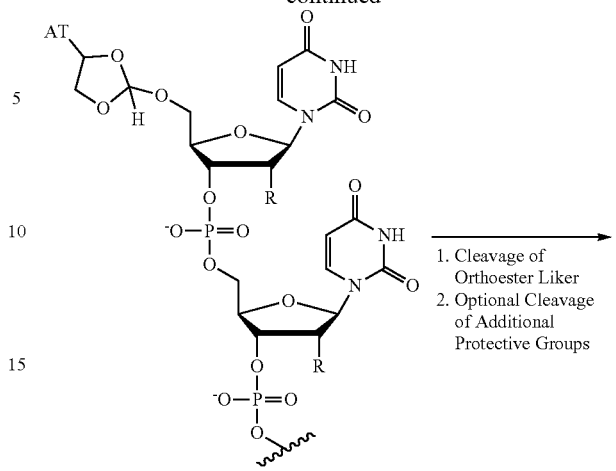
1. Cleavage of Orthoester Liker
2. Optional Cleavage of Additional Protective Groups
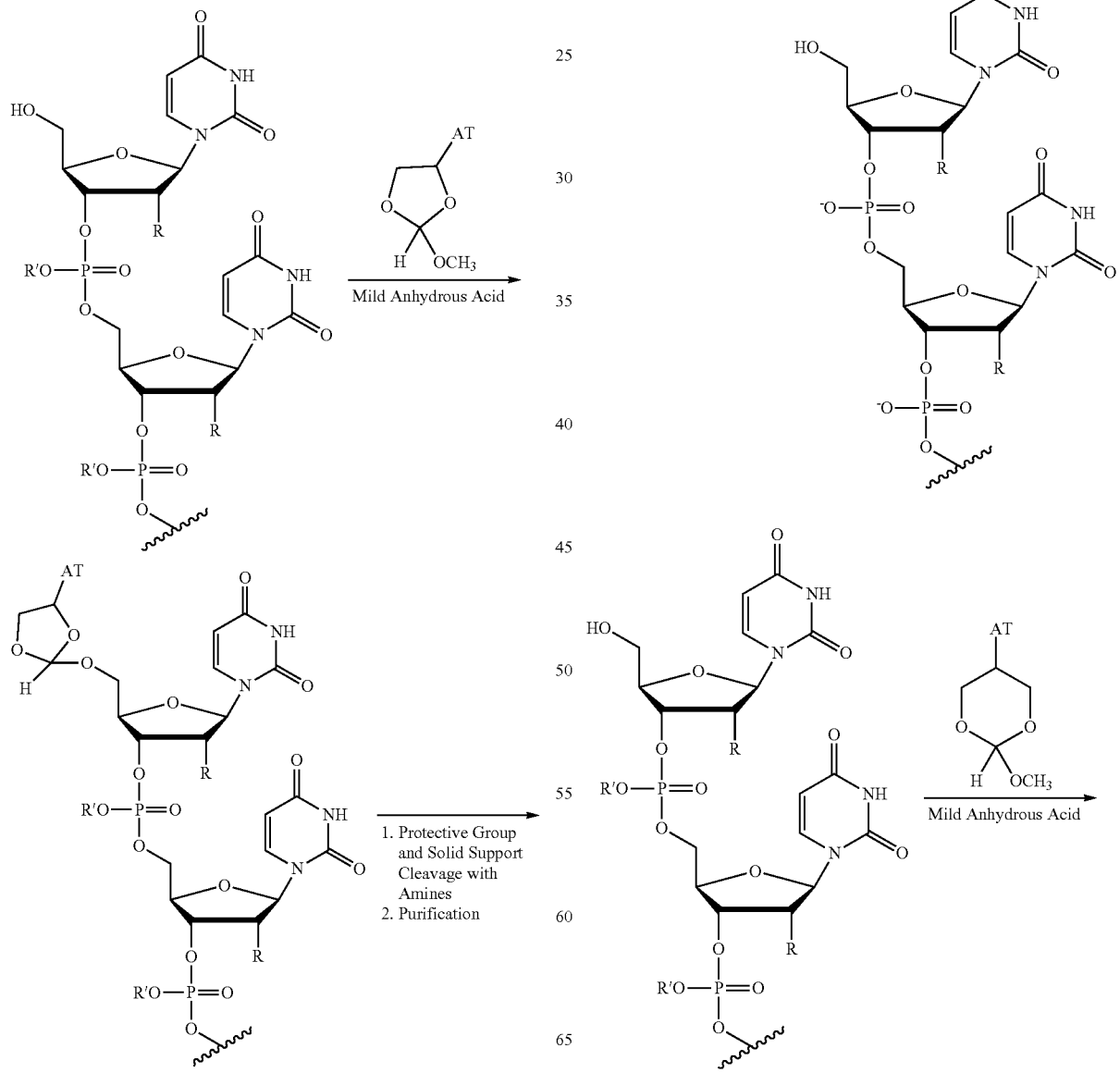

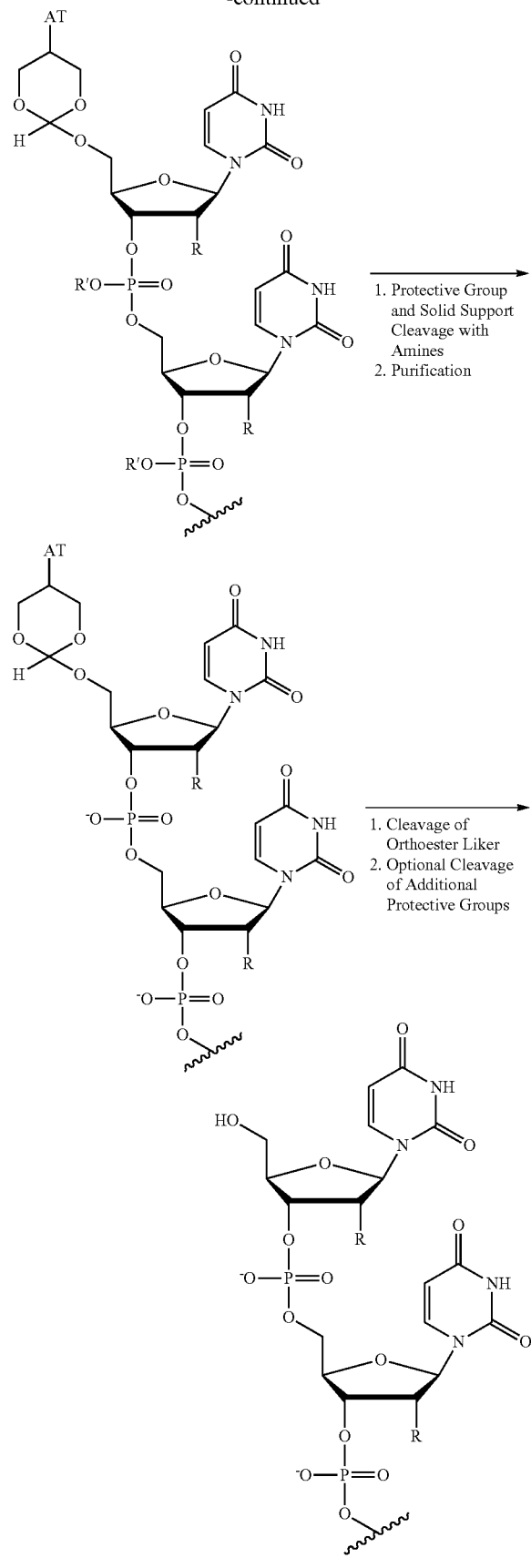

Nascently synthesized oligonucleotides, DNA, RNA or modified oligonucleotides are synthesized on solid support. The resulting full-length product is prepared for attaching an orthoester linker by removing the final protective group in a de-blocking step. That protective group can be various groups well known in the literature; most typically DMT, Pixyl, or BZH. The synthesis of oligonucleotides can occur in the 3' to 5' direction where the final protective group is removed from the 5'-hydroxyl of the resulting oligonucleotide, or the synthesis can occur in the 5' to 3' direction in which the final protective group is removed from the 3'-hydroxyl of the resulting oligonucleotide. At this point the phosphorus protective group can be optionally removed from the nascently synthesized oligonucleotide. A 1,3-dioxalane or 1,4-dioxalane orthoester linker attached to an Affinity Tag (AT), is reacted with the hydroxy group liberated in the final deblocking step using mild acid as a trans-orthoesterification catalyst. The resulting affinity tag containing orthoester linker-oligonucleotide conjugate can now be treated with various basic amines to optionally removed various protective groups such as TC, or PivOM, and possibly cleave the solid support attachment. The liberated oligonucleotide can then be purified using a chromatographic separation or a solid-phase extraction aided by the affinity tag. The orthoester linker can then be removed using mild acid along with any additional acid labile protective groups, such as ACE, and the purified oligonucleotide can then be optionally further deprotected with various reagents such as fluoride ion, such as TOM or TBDMS.

Example 25

Attachment of 2-methoxy-4-(((3,3,4,4,5,5,6,6,7,7,8,8,8-tridecafluorooctyl)oxy)methyl)-1,3-dioxolane to a 21 Nucleotide RNA made using TC phosphoramidites.

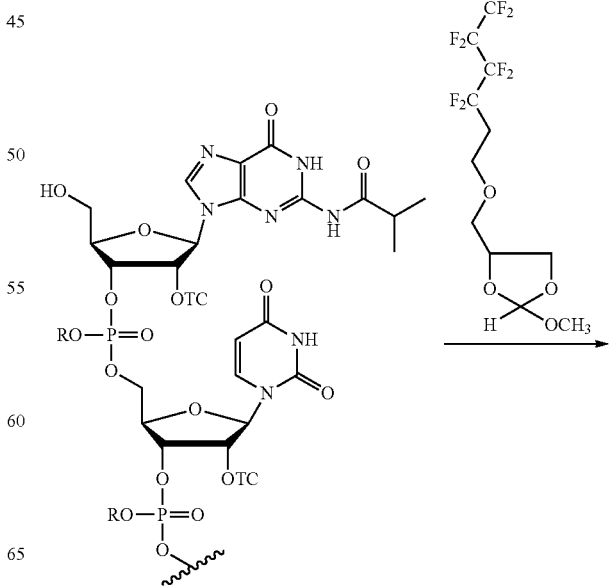

-continued

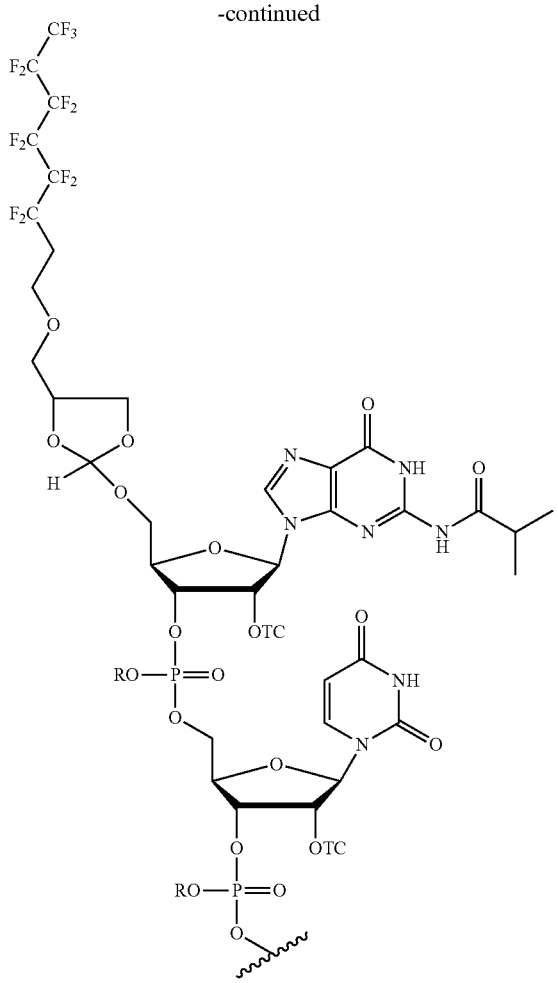

A 21-nucleotide, oligoribonucleotide was synthesized using TC phosphoramidites on deoxy-thymidine containing controlled pore glass (CPG; Prime Synthesis Aston, Pa.), using an ATKA 100 DNA/RNA synthesizer (General Electric) and a 12 ml column, yielding 6.5 g of CPG containing the desired crude oligoribonucleotide (5'-GUGUCAGUA-CAGAUGAGGCCT-3', SEQ ID NO. 1). Approximately, 1 micromole of the crude oligonucleotide, based upon the CPG loading, 30 mg, was placed in a high-throughput DNA/RNA synthesis column (Biosearch Technologies, Inc., Novato, Calif.). 100 microliters of the 2-methoxy-4-(((3,3, 4,4,5,5,6,6,7,7,8,8,8-tridecafluorooctyl)-oxy)methyl)-1,3-dioxolane (orthoester) was mixed with 80 microliters of anhydrous acetonitrile and 20 microliters of a 3% wt/wt solution of dichloroacetic acid in anhydrous dichloromethane (Glen Research). The orthoester solution was added to the column and heated to 60° C., for 1 hour. The column was rinsed with anhydrous acetonitrile (1 ml), and then 200 microliters of neat, anhydrous, ethylene diamine was added to the column and allowed to react for 2 hours. The ethylene diamine was rinsed from the column using acetonitrile (1 ml) and then RNA was removed from the column using 300 microliters of a 0.1 M ammonium acetate buffer in water (pH 7.0). The yield of the orthoester linker conversion was determined by HPLC analysis using a reverse-phase C-18 column and an Agilent Technologies 1260 Infinity LC (using a gradient from 0% B to 50% B in 20 minutes; A: 0.1 M triethyl ammonium acetate in water, pH 7.0, B: 0.1 M triethyl ammonium acetate in 30/70, vol/vol, water/acetonitrile). The reaction demonstrated 55% conversion of the full-length product to product containing the orthoester linker.

Example 26

Attachment of 2-methoxy-4-(((3,3,4,4,5,5,6,6,7,7,8,8,8-tridecafluorooctyl)oxy)methyl)-1,3-dioxolane to a 100 Nucleotide RNA made using TC phosphoramidites

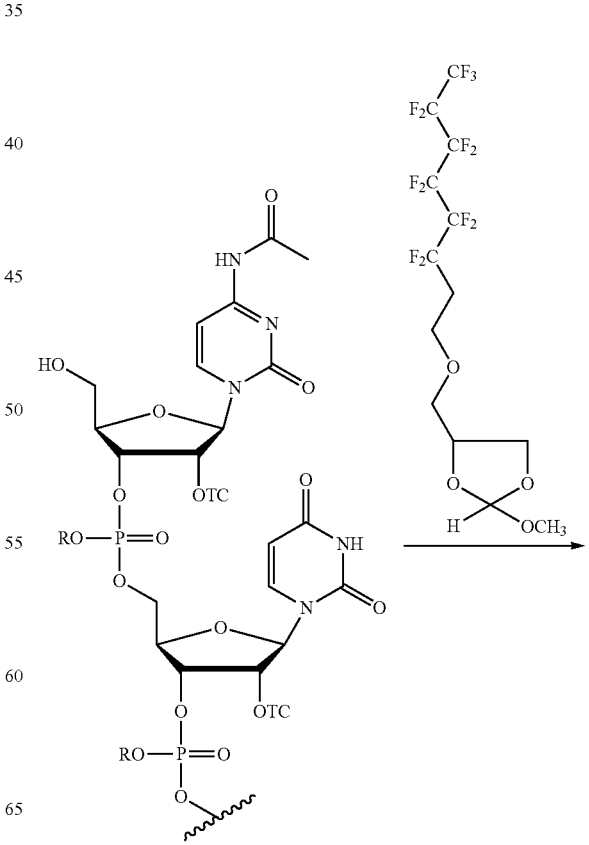

-continued

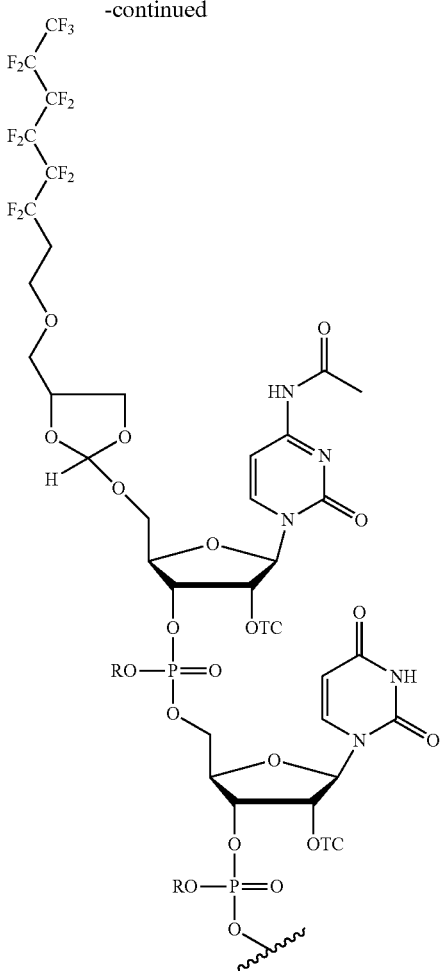

A 100-nucleotide, oligoribonucleotide was synthesized using TC phosphoramidites on CPG containing a protected uridine-2'-OTC (Prime Synthesis Aston, Pa.), using an ATKA 100 DNA/RNA synthesizer (General Electric) and a 12 ml column, yielding 6.8 g of CPG containing the desired crude oligoribonucleotide (5'-CUU GCC CCA CAG GGC AGU AAG UUU UAG AGC UAG AAA UAG CAA GUU AAA AUA AGG CUA GUC CGU UAU CAA CUU GAA AAA GUG GCA CCG AGU CGG UGC UUUU-3', SEQ ID NO. 2). Approximately, 1 micromole of the crude oligonucleotide, based upon the CPG loading, 40 mg, was placed in a high-throughput DNA/RNA synthesis column (Biosearch Technologies, Inc., Novato, Calif.). 100 microliters of the 2-methoxy-4-(((3,3,4,4,5,5,6,6,7,7,8,8,8-tridecafluorooctyl)-oxy)methyl)-1,3-dioxolane (orthoester) was mixed with 80 microliters of anhydrous acetonitrile and 20 microliters of a 3% wt/wt solution of dichloroacetic acid in anhydrous dichloromethane (Glen Research). The orthoester solution was added to the column and heated to 60° C., for 1 hour. The column was rinsed with anhydrous acetonitrile (1 ml), and then 200 microliters of neat, anhydrous, ethylene diamine was added to the column and allowed to react for 2 hours. The ethylene diamine was rinsed from the column using acetonitrile (1 ml) and then RNA was removed from the column using 300 microliters of a 0.1 M ammonium acetate buffer in water (pH 7.0). The yield of the orthoester linker conversion was determined by HPLC analysis using a reverse-phase C-18 column and an Agilent Technologies 1260 Infinity LC (using a gradient from 0% B to 50% B in 20 minutes; A: 0.1 M triethyl ammonium acetate in water, pH 7.0, B: 0.1 M triethyl ammonium acetate in 30/70, vol/vol, water/acetonitrile). The reaction demonstrated 25% conversion of the full-length product to product containing the orthoester linker.

Example 27

Attachment of 4-(((3,3,4,4,5,5,6,6,7,7,8,8,8-tridecafluorooctyl)oxy)methyl)-2-(2,2,2-trifluoroethoxy)-1,3-dioxolane to a 100 Nucleotide RNA made using TC phosphoramidites.

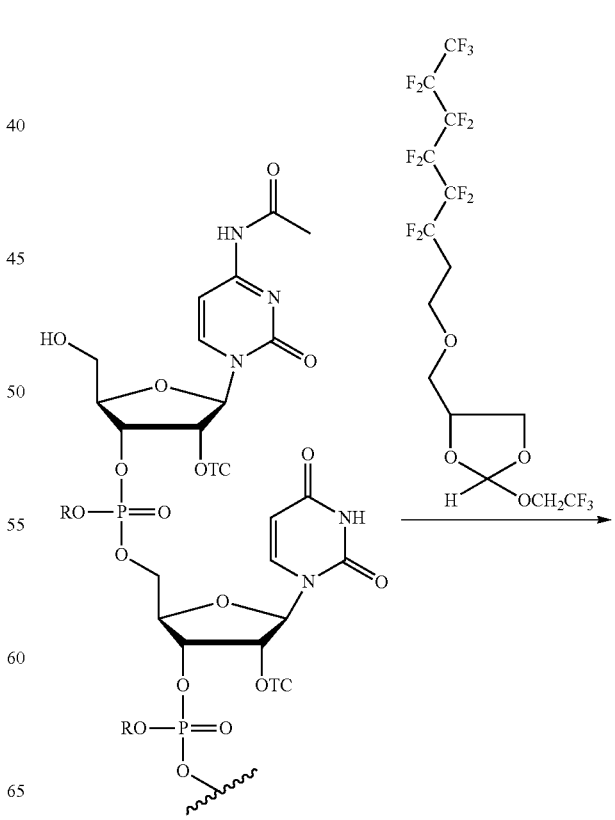

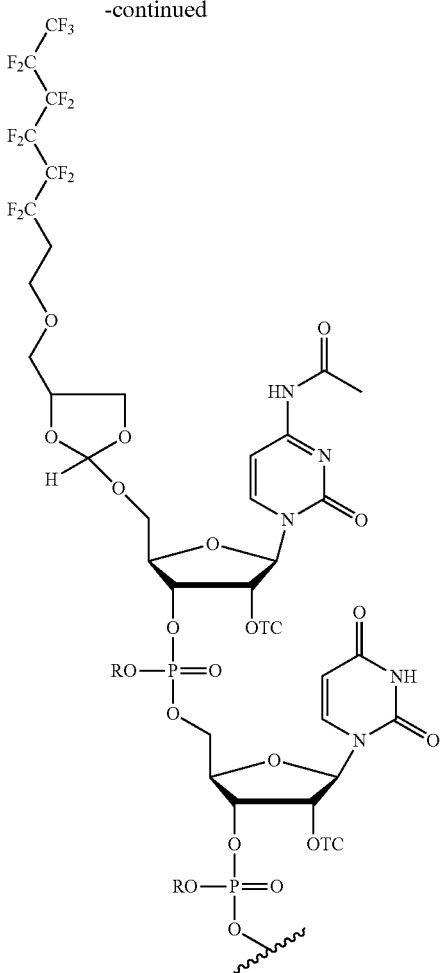

A 100-nucleotide, oligoribonucleotide was synthesized using TC phosphoramidites on CPG containing a protected uridine-2'-OTC (Prime Synthesis Aston, Pa.), using an ATKA 100 DNA/RNA synthesizer (General Electric) and a 12 ml column, yielding 6.8 g of CPG containing the desired crude oligoribonucleotide (5'-CUU GCC CCA CAG GGC AGU AAG UUU UAG AGC UAG AAA UAG CAA GUU AAA AUA AGG CUA GUC CGU UAU CAA CUU GAA AAA GUG GCA CCG AGU CGG UGC UUUU-3', SEQ ID NO. 2). Approximately, 1 micromole of the crude oligonucleotide, based upon the CPG loading, 40 mg, was placed in a high-throughput DNA/RNA synthesis column (Biosearch Technologies, Inc., Novato, Calif.). 100 microliters of the 4-(((3,3,4,4,5,5,6,6,7,7,8,8,8-tridecafluorooctyl)oxy)methyl)-2-(2,2,2-trifluoroethoxy)-1,3-dioxolane (orthoester) was mixed with 80 microliters of anhydrous acetonitrile and 20 microliters of a 3% wt/wt solution of dichloroacetic acid in anhydrous dichloromethane (Glen Research). The orthoester solution was added to the column and heated to 60° C., for 1 hour. The column was rinsed with anhydrous acetonitrile (1 ml), and then 200 microliters of neat, anhydrous, ethylene diamine was added to the column and allowed to react for 2 hours. The ethylene diamine was rinsed from the column using acetonitrile (1 ml) and then RNA was removed from the column using 300 microliters of a 0.1 M ammonium acetate buffer in water (pH 7.0). The yield of the orthoester linker conversion was determined by HPLC analysis using a reverse-phase C-18 column and an Agilent Technologies 1260 Infinity LC (using a gradient from 0% B to 50% B in 20 minutes; A: 0.1 M triethyl ammonium acetate in water, pH 7.0, B: 0.1 M triethyl ammonium acetate in 30/70, vol/vol, water/acetonitrile). The reaction demonstrated 52% conversion of the full-length product to product containing the orthoester linker.

Example 28

2-Step Attachment of Fluorous Affinity Tag to Orthoester Linker 30 mg of 3'-RNA-CPG is treated with 100 μL 3% dichloroacetic acid in dichloromethane (Glen Research) twice for 1 min, followed by 8 mL acetonitrile, and dried with a stream of nitrogen. 45 μL of 1,2-bis((2-methoxy-1,3-dioxolan-4-yl)methyl)disulfane orthoester, 45 μL acetonitrile (Aldrich), and 10 μL 3% dichloroacetic acid in dichloromethane (Glen Research) are added to the 3'-RNA-CPG with a free 5'-hydroxyl group, and the mixture is heated at 60° C. for 1 hr. After removal of residual liquid, the CPG is washed with 8 mL acetonitrile, followed by drying with a stream of nitrogen. The RNA-CPG: orthoester conjugate is treated with 200 μL 50 mM TCEP (Aldrich) solution, prepared in 200 mM ammonium bicarbonate, pH 8.0, for 1 hour at 23° C. The reduced thiol containing RNA conjugate on CPG is then incubated with a solution of 1H,1H,2H,2H-Perfluorooctyl iodide (Aldrich) at a concentration of 10 mM in acetonitrile. The conjugate is then deprotected and released from the CPG by treatment with 100 uL neat ethylenediamine for 5 hours at 23° C., followed by washing with 8 mL of acetonitrile. The fluorinated-RNA conjugate is eluted from the CPG resin with 0.3 mL 0.1 M ammonium acetate buffer (pH=6.9), and analyzed by deconvoluted ESI/TOF mass spectrometry.

Example 29

Cartridge Purification or Solid-Phase Extraction Purification of Oligonucleotides with Fluorous Affinity Tag 30 mg of 100mer RNA-CPG was treated with 100 uL 3% trichloroacetic acid in dichloromethane (Glen Research) twice for 1 min, followed by 8 mL acetonitrile (Aldrich), and dried with a stream of nitrogen. 80 μL of 4-(((3,3,4,4,5,5,6,6,7,7,8,8,8-tridecafluorooctyl)oxy)methyl)-2-(2,2,2-trifluoroethoxy)-1,3-dioxolane, 80 μL acetonitrile, and 40 μL of 3% dichloroacetic acid in dichloromethane (Glen Research) were added to the 100mer RNA CPG, and the mixture was heated at 75° C. for 15 minutes. After removal of residual liquid, the CPG was washed with 8 mL acetonitrile, followed by drying with a stream of nitrogen. The CPG was next treated with 0.5 mL neat ethylenediamine (Aldrich) at 40° C. for 1 hour. After removal of residual liquid, the CPG was washed with 8 mL acetonitrile, followed by drying with a stream of nitrogen. The fluorous orthoester: RNA conjugate was eluted from the CPG with 1 mL of 10% w/v sodium chloride containing 5% v/v dimethylformamide (Aldrich).

A "Fluoro-pak II" cartridge (Berry & Associates) was conditioned by the addition of 1 mL acetonitrile, followed by 1 mL 0.1 M triethylammonium acetate, pH 7.0 (Glen Research), and 1 mL of 10% w/v sodium chloride containing 5% v/v dimethylformamide (Aldrich). The eluted fluorous orthoester: RNA conjugate was added to the top of this cartridge by syringe and using a syringe of air pushed through the resin at a rate of approximately 2 seconds per drop until the buffer reached the top of the resin. The resin was washed twice with 2 mL portions of 10% acetonitrile (v/v) in 100 mM triethylammonium acetate, pH 7.0, followed by two 2 mL portions of 12.5% acetonitrile (v/v) in 100 mM triethylammonium acetate, pH 7.0. The fluorous orthoester: RNA conjugate was eluted from the resin with 1 mL of 80% MeOH (v/v) in 0.1 M triethylammonium acetate, pH 5.5. The eluted fraction was concentrated to dryness on a Savant speedvac, dissolved in 212 µL 0.1 M triethylammonium acetate, pH 5.5, and allowed to incubate at 23° C. After 1 hour, 38 µL acetonitrile was added to the reaction solution and passed through another conditioned Fluoro-pak II cartridge, followed by 1 mL of 12.5% acetonitrile (v/v) in 100 mM triethylammonium acetate, pH 7.0. The two fractions were combined and evaporated to dryness on a Savant speedvac to produce 0.7 mg affinity purified 100mer RNA.

The procedure extends to microtiter formats of 6, 12, 24, 48, 96, 384 or 1536 wells using plates containing frits and bulk fluorous resin. A vacuum manifold can be used to pull all solutions through the resin to be collected or sent to waste. This process has been shown to be automatable onto a laboratory robot; Agilent Bravo Workstation.

In view of this disclosure it is noted that the methods can be implemented in keeping with the present teachings. Further, the various components, materials, structures and parameters are included by way of illustration and example only and not in any limiting sense. In view of this disclosure, the present teachings can be implemented in other applications and components, materials, structures and equipment to implement these applications can be determined, while remaining within the scope of the appended claims.

---

---

We claim:

1. An oligonucleotide orthoester linker conjugate comprising an oligonucleotide which comprises at its 5' or 3' end a moiety of formula (IV),

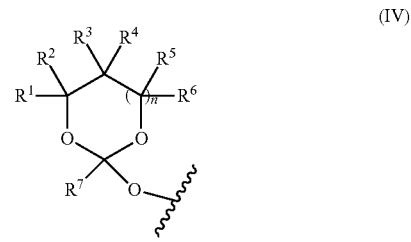

wherein the oxygen linked to the squiggly line is the oxygen of the 5'end or the 3'end of the oligonucleotide; wherein at least one of $R^1$, $R^2$, $R^3$, $R^4$, $R^5$, $R^6$ and $R^7$ is $C_1$-$C_{24}$ alkyl, $C_1$-$C_{24}$ heteroalkyl, $C_2$-$C_{24}$ alkenyl, $C_2$-$C_{24}$ heteroalkenyl, $C_2$-$C_{24}$ alkynyl, $C_2$-$C_{24}$ heteroalkynyl, halogen, aryl, heteroaryl, heterocyclyl, carbocyclyl, any substituted equivalent or a combination thereof and the remaining $R^1$, $R^2$, $R^3$, $R^4$, $R^5$, $R^6$ and $R^7$ are H, $C_1$-$C_6$ alkyl, $C_2$-$C_6$ alkenyl, $C_2$-$C_6$ alkynyl, $C_6$-$C_{12}$ arylalkyl, carbocyclyl, heterocyclyl, any substituted equivalent or combination thereof, and n is 0, 1, or 2, wherein at least one of $R^1$, $R^2$, $R^3$, $R^4$, $R^5$, $R^6$ or $R^7$ comprises an affinity tag; and with the proviso that said moiety is not

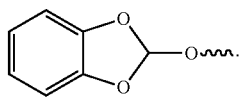

2. The oligonucleotide orthoester linker conjugate of claim 1, wherein n=0 and the affinity tag is a fluorous or a hydrophobic tag with a cLog P value of at least 3, wherein the cLog P value is calculated from solubility in octanol and water.

3. The oligonucleotide orthoester linker conjugate of claim 1, wherein the oligonucleotide comprises an oligoribonucleic acid (RNA).

4. The oligonucleotide orthoester linker conjugate of claim 1, wherein at least one of $R^1$, $R^2$, $R^3$, $R^4$, $R^5$ or $R^6$ is a fluorosubstituted alkyl, a fluorosubstituted alkenyl, a fluorosubstituted alkynyl, a fluorosubstituted aryl, a fluorosubstituted heteroalkyl, a fluorosubstituted heteroalkenyl, a fluorosubstituted heteroalkynyl, or a fluorosubstituted heterocyclyl.

5. The oligonucleotide orthoester linker conjugate of claim 1, wherein at least one of $R^1$, $R^2$, $R^3$, $R^4$, $R^5$ or $R^6$ is a fluorous tag and the remaining R groups including $R^7$ are H.

6. The oligonucleotide of claim 1, wherein at least two of $R^1$, $R^2$, $R^3$, $R^4$, $R^5$ or $R^6$ are a fluorous tag.

7. The oligonucleotide orthoester linker conjugate of claim 1, wherein said moiety is selected from the group consisting of:

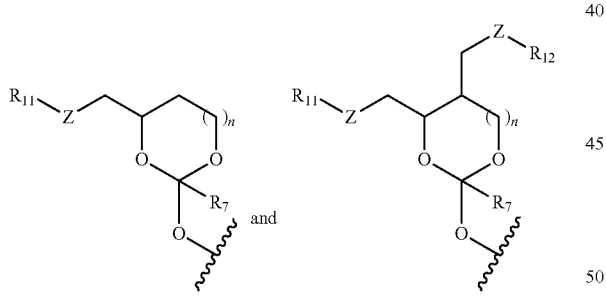

wherein $R^{11}$ and $R^{12}$ are each independently H, $C_1$-$C_{23}$ alkyl, $C_1$-$C_{23}$ heteroalkyl, $C_1$-$C_{23}$ substituted alkyl, $C_2$-$C_{23}$ alkenyl, $C_2$-$C_{23}$ heteroalkenyl, $C_2$-$C_{23}$ substituted alkenyl, $C_2$-$C_{23}$ alkynyl, $C_2$-$C_{23}$ heteroalkynyl, $C_2$-$C_{23}$ substituted alkynyl, aryl, substituted aryl, heteroaryl, substituted heteroaryl, heterocyclyl or substituted heterocyclyl provided that at least one of $R^{11}$ and $R^{12}$ comprises an affinity tag; $R^7$ is H, methyl, ethyl, n-propyl, phenyl or benzyl; Z are each independently $CR^aR^b$, O, S or $NR^a$ wherein $R^a$ and $R^b$ are each independently H, $C_1$-$C_6$ alkyl, or $R^a$ and $R^{11}$ or $R^a$ and $R^{12}$ together form a heterocycle with N; n is 0, 1, or 2.

8. The oligonucleotide orthoester linker conjugate of claim 1, wherein said moiety is:

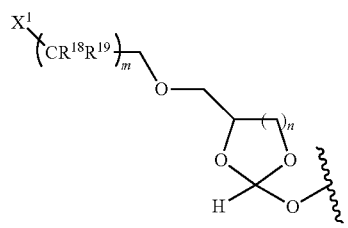

wherein $X^1$ is H, F, an azido, a protected sulfhydryl, a protected poly-sulfhydryl, a poly-histidine, a protected amino group, a protected hydrazide group, a protected oxyamine group, a maleimide, a cyclooctyne, a conjugated diene, a $C_2$ alkenyl group, a $C_2$ substituted alkenyl group, a $C_2$ alkynyl group or a $C_2$ substituted alkynyl group; $R^{18}$ and $R^{19}$ are each independently H, F, $C_{1-3}$ heteroalkyl or $C_{1-3}$ substituted alkyl; n is 1 or 2; and m is an integer ranging from 0 to 12.

9. The oligonucleotide orthoester linker conjugate of claim 1, wherein said moiety is selected from the group consisting of:

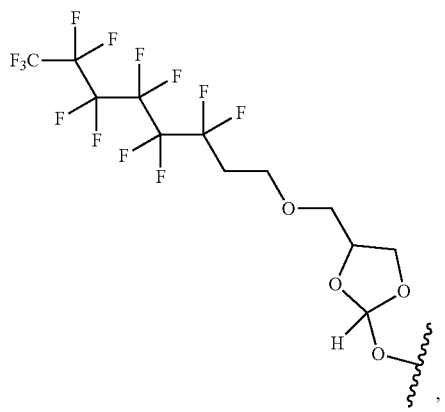

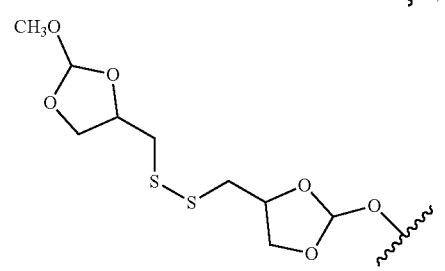

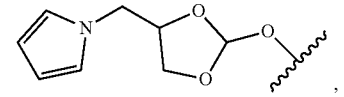

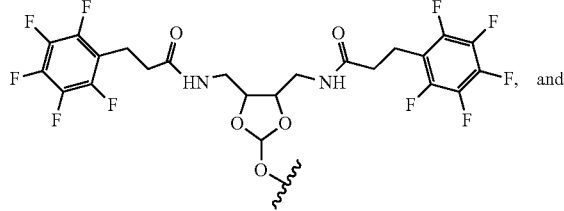

-continued
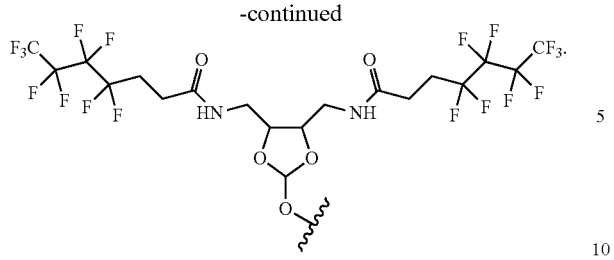
* * * * *

UNITED STATES PATENT AND TRADEMARK OFFICE
CERTIFICATE OF CORRECTION

PATENT NO. : 11,548,876 B2
APPLICATION NO. : 16/793808
DATED : January 10, 2023
INVENTOR(S) : Douglas J. Dellinger et al.

It is certified that error appears in the above-identified patent and that said Letters Patent is hereby corrected as shown below:

On the Title Page

Item (56), in Column 2, under "Other Publications", Line 25, delete "H3P04" and insert -- H3PO4 --.

Item (56), in Column 2, under "Other Publications", Line 26, delete "H2P04-/HP04=" and insert -- H2PO4-/HPO4= --.

In the Drawings

On sheet 5 of 9, in Figure 5, Line 1, delete " 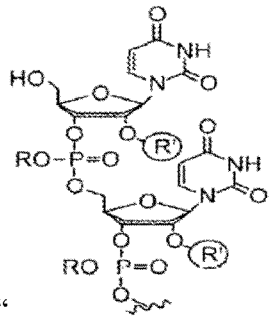 " and insert 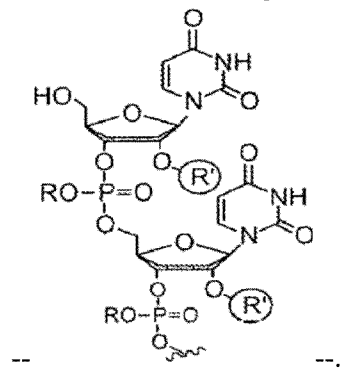 --.

Signed and Sealed this
Twenty-first Day of May, 2024

*Katherine Kelly Vidal*
*Director of the United States Patent and Trademark Office*

CERTIFICATE OF CORRECTION (continued)
U.S. Pat. No. 11,548,876 B2

On sheet 5 of 9, in Figure 5, Line 1, delete "  " and insert -- 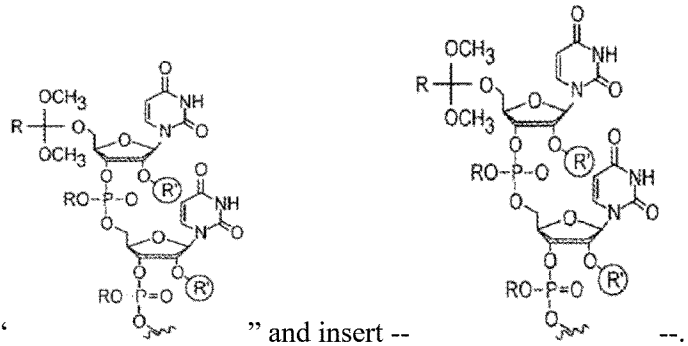 --.

In the Specification

In Column 5, Line 30, delete "cLog P" and insert -- cLogP --.

In Column 6, Line 41, delete "cLog P" and insert -- cLogP --.

In Column 10, Line 10, delete "cLog P" and insert -- cLogP --.

In Column 13, Line 49, delete "support," and insert -- support. --.

In Column 13, Line 54, delete "trityl/Cis" and insert -- trityl/$C_{18}$ --.

In Column 14, Line 21, delete "(log P)." and insert -- (logP). --.

In Column 14, Line 22, delete "(log P)" and insert -- (logP) --.

In Column 14, Line 25, delete "cLog P." and insert -- cLogP. --.

In Column 14, Line 25, delete "cLog P" and insert -- cLogP --.

In Column 14, Line 27, delete "cLog P" and insert -- cLogP --.

In Column 15, Line 45, delete "cycloakenyl," and insert -- cycloalkenyl, --.

In Column 22, Line 52, delete "(La)" and insert -- (Ia) --.

In Column 23, Line 20, delete "cLog P" and insert -- cLogP --.

In Column 24, Line 38, delete "Wherein" and insert -- wherein --.

In Column 26, Line 6, delete "preferrably," and insert -- preferably, --.

In Column 27, Line 63, delete "S-tranferase" and insert -- S-transferase --.

In Column 27, Line 65, delete "gluthathione" and insert -- glutathione --.

CERTIFICATE OF CORRECTION (continued)

In Column 30, Line 55, delete "phoshitetriester" and insert -- phosphitetriester --.

In Column 31, Line 56, delete "7.4)" and insert -- 7.4). --.

In Column 33, Line 34, delete "7-member 7-member" and insert -- 7-member --.

In Column 35, Line 33, delete "cLog P" and insert -- cLogP --.

In Column 43, Line 56, delete "$R_6$" and insert -- $R^6$ --.

In Column 46, Line 48, delete "cLog P" and insert -- cLogP --.

In Column 48, Line 58, delete "equivalent," and insert -- equivalent. --.

In Column 58, Line 58, delete "35.1" and insert -- 351.1 --.

In Column 59, Line 14, delete "trifluoroethy)" and insert -- trifluoroethyl) --.

In Column 59, Line 29, delete "m/z)" and insert -- m/z). --.

In Column 59, Lines 33-37, delete " 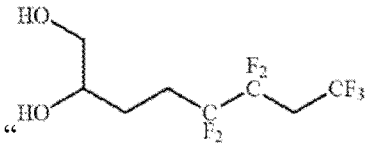 " and insert 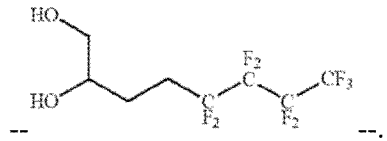 -- --.

In Column 67, Line 33, delete "3-(Pentafluoro" and insert -- 3-(Pentafluorophenyl)propionic --.

In Column 68, Lines 38-43, delete " 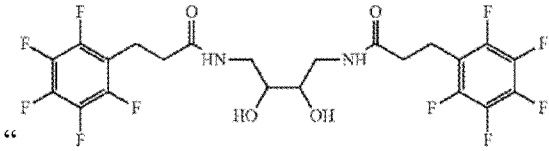 " and insert -- 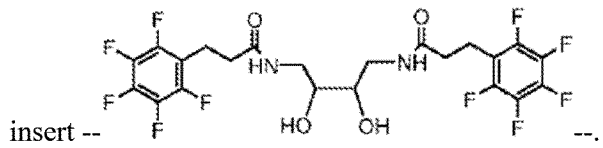 --.

In Column 71, Line 66, delete "NaI" and insert -- NaI --.

In Column 73, Line 20, delete "m/z." and insert -- m/z). --.

CERTIFICATE OF CORRECTION (continued)
U.S. Pat. No. 11,548,876 B2

In Column 73, Line 53, delete "500p" and insert -- 500 µL --.

In Column 74, Line 48, delete "(ThermoFisher)" and insert -- (Thermo Fisher) --.

In Column 77, Line 18, delete "Dioxalane" and insert -- Dioxolane --.

In Column 77, Line 19, delete "Dioxalane" and insert -- Dioxolane --.

In Column 80, Lines 16-17, delete "dioxalane" and insert -- dioxolane --.

In Column 80, Line 17, delete "dioxalane" and insert -- dioxolane --.

In Column 82, Line 29, delete "phosphoramidites" and insert -- phosphoramidites. --.

In Column 83, Line 52, delete "UUUU-3'," and insert -- UUU U -3', --.

In Column 85, Line 50, delete "UUUU-3'," and insert -- UUU U -3', --.

In the Claims

In Column 88, Line 64, in Claim 1, delete "thereof," and insert -- thereof; --.

In Column 89, Line 10, in Claim 2, delete "cLog P" and insert -- cLogP --.

In Column 89, Line 11, in Claim 2, delete "cLog P" and insert -- cLogP --.

In Column 90, Lines 44-54, in Claim 9, after " 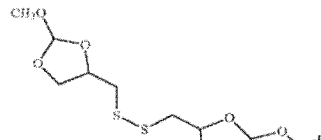 " insert -- , --.

SEQUENCE LISTING

```
<160> NUMBER OF SEQ ID NOS: 2

<210> SEQ ID NO 1
<211> LENGTH: 21
<212> TYPE: DNA
<213> ORGANISM: Artificial Sequence
<220> FEATURE:
<223> OTHER INFORMATION: Synthesized in laboratory

<400> SEQUENCE: 1
gugucaguac agaugaggcc t                                              21

<210> SEQ ID NO 2
<211> LENGTH: 100
<212> TYPE: RNA
<213> ORGANISM: Artificial Sequence
<220> FEATURE:
<223> OTHER INFORMATION: Synthesized in laboratory

<400> SEQUENCE: 2
cuugccccac agggcaguaa guuuuagagc uagaaauagc aaguuaaaau aaggcuaguc    60
cguuaucaac uugaaaaagu ggcaccgagu cggugcuuuu                         100
```